US006096321A

United States Patent [19]

Girardeau et al.

[11] Patent Number: 6,096,321

[45] Date of Patent: Aug. 1, 2000

[54] CLPG SUBUNIT OF CS31A PROTEIN CAPSULE CONTAINING HETEROLOGOUS PEPTIDES

[75] Inventors: Jean-Pierre Girardeau, Saint Genes Champanelle; Christine Martin, La Roche Blanche; Marie-Claire Mechin, Beaumont; Maurice Der Vartanian, Saint Genes Champanelle; François Bousquet, Ceyrat, all of France

[73] Assignee: Institut National de la Recherche Agronomique-INRA, Paris, France

[21] Appl. No.: 08/491,954

[22] PCT Filed: Dec. 21, 1993

[86] PCT No.: PCT/FR93/01281

§ 371 Date: Feb. 16, 1996

§ 102(e) Date: Feb. 16, 1996

[87] PCT Pub. No.: WO94/14967

PCT Pub. Date: Jul. 7, 1994

[30] Foreign Application Priority Data

Dec. 22, 1992 [FR] France .................................. 92 15464

[51] Int. Cl.[7] ........................ A61K 39/108; A61K 39/00; A61K 39/02; A61K 39/295

[52] U.S. Cl. .................................... 424/257.1; 424/184.1; 424/185.1; 424/190.1; 424/192.1; 424/196.11; 424/197.11; 424/200.1; 424/201.1; 424/234.1; 424/242.1

[58] Field of Search ............................. 424/184.1, 185.1, 424/190.1, 192.1, 196.11, 197.11, 200.1, 201.1, 234.1, 242.1, 257.1

[56] References Cited

PUBLICATIONS

Hedegaard et al, J. Cell Biochem Suppl 12 B, p. 41 (1988).

Girardeau et al. Journal of Bacteriology 173(23):7673–7683, 1991.

Martin et al. Microbial Pathogenesis 10:429–442, 1991.

Bakker et al. Microbial Pathogenesis 8:343–352, 1990.

Kohli et al. Journal of General Virology 73:907–914, 1992.

Delmas et al. Journal of General Virology 71:1313–1323, 1990.

*Primary Examiner*—Christopher L. Chin

*Assistant Examiner*—V. Ryan

*Attorney, Agent, or Firm*—Schnader Harrison Segal & Lewis LLP

[57] ABSTRACT

A CS31A protein capsule subunit having an aminoacid sequence modified by at least one heterologous peptide, the CS31A protein capsule comprising said subunit, and micro-organisms having the CS31A protein capsule with its subunit aminoacid sequence modified by at least one heterologous peptide, are disclosed. Methods for preparing said subunits, CS31A protein capsules comprising same, and micro-organisms having CS31A protein capsules, as well as the use thereof for preparing vaccines, producing peptides and preparing immunoassays, are also disclosed.

29 Claims, 53 Drawing Sheets ctcagtgccagacagcagggtgagatgtggtga 33 taagcgtgccgaggcaaagaaacaggttgagttaa 68 gaacgatgcaccggcagagctgaagtcccggtca 102 gttaccgggaaatcttgcagatagcactgcaggtg 137 gaagactgagaatttatctccgacaacagatgcaa 172

P1(-35)

tacatccctgactccggaatgggtcatattggtaa 207

P1(-10)

agggatttaccgtattttaaaagggaataacgca 242 aaactattctgaattaaacactgtgtttaattaaa 277

P2(-10)

gcggctatttaaataagtccacaggggatagttttg 313 cggtaattccggaaaaataaggattgccgatatcg 348 rbs atttattatttgtgaaatataaaggaatttatttt 383

| | | | | | | | | | |
|---|---|---|---|---|---|---|---|---|---|
| ATG | AAA | AAG | ACT | CTG | ATT | GCA | CTG | GCT | 390 |
| M | K | K | T | L | I | A | L | A | 9 |
| GTG | GCT | GTT | TCG | GCA | GTA | TCA | GGT | GCC | 408 |
| V | A | V | S | A | V | S | G | A | 18 |
| GCG | CAT | GCG | TGG | ACC | ACT | GGT | GAT | TTT | 420 |
| A | H | A | W | T | T | G | D | E | |

FIG. 9a

| | | | | | | | | | |
|---|---|---|---|---|---|---|---|---|---|
| AAT<br>N | GGT<br>G | TCA<br>S | TTT<br>F | GAT<br>D | ATG<br>M<br>+1 | AAT<br>N | GGC<br>G | ACA<br>T | 448<br>36 |
| ATT<br>I | ACT<br>T | GCT<br>A | GAT<br>D | GCG<br>A | TAT<br>Y | AAA<br>K | GAC<br>D | AAA<br>K | 466<br>45 |
| TGG<br>W | GAA<br>E | TGG<br>W | ATG<br>M | GTT<br>V | GGG<br>G | GGC<br>G | GCT<br>A | CTC<br>L | 484<br>54 |
| TCC<br>S | TTC<br>F | AAC<br>N | AAC<br>N | ACT<br>T | ATC<br>I | AAG<br>K | GAA<br>E | ATG<br>M | 502<br>63 |
| ACA<br>T | GGT<br>G | GAC<br>D | AGT<br>S | AAG<br>K | CTG<br>L | CTG<br>L | ACC<br>T | ATC<br>I | 520<br>72 |
| ACT<br>T | CAG<br>Q | TCT<br>S | GAA<br>E | CCA<br>P | GCT<br>A | CCT<br>P | ATT<br>I | CTT<br>L | 538<br>81 |
| TTA<br>L | GGG<br>G | CGC<br>R | ACA<br>T | AAA<br>K | GAG<br>E | GCG<br>A | TTT<br>F | GCA<br>A | 556<br>90 |
| GCA<br>A | TCG<br>S | ATT<br>I | GTT<br>V | GGT<br>G | GTT<br>V | GGT<br>G | GCA<br>A | ATT<br>I | 574<br>99 |
| CCT<br>P | TTA<br>L | ATT<br>I | GCG<br>A | TTC<br>F | AGT<br>S | GAT<br>D | TAT<br>Y | GAA<br>E | 592<br>108 |
| GGG<br>G | AAC<br>N | GGA<br>G | GTT<br>V | GCC<br>A | TTA<br>L | CAG<br>Q | AGT<br>S | TCT<br>S | 601<br>117 |
| GGG<br>G | GAT<br>D | AAC<br>N | GGT<br>G | AAG<br>K | GGG<br>G | TTC<br>F | TTT<br>F | GAA<br>E | 628<br>126 |

FIG. 9b

| | | | | | | | | | |
|---|---|---|---|---|---|---|---|---|---|
| TTG | CCC | ATG | AAA | GAT | GAT | AGT | GGA | AAT | 646 |
| L | P | M | K | D | D | S | G | N | 135 |
| AAT | CTC | GGT | AGC | GTA | AAA | GTT | AAT | GTT | 664 |
| N | L | G | S | V | K | V | N | V | 144 |
| ACT | TCT | GCT | GGC | CTG | TTT | TCC | TAT | AGT | 682 |
| T | S | A | G | L | F | S | Y | S | 153 |
| GAA | ATA | TCA | ACA | GGT | TTA | GTT | GGT | ATA | 700 |
| E | I | S | T | G | L | V | G | I | 162 |
| ACT | TCT | GTT | GCC | AGT | GGC | GAT | AAT | ACA | 716 |
| T | S | V | A | S | G | D | N | T | 171 |
| AGT | ATT | TAT | TAT | GGT | GGT | CTG | GTG | TCG | 736 |
| S | I | Y | Y | G | G | L | V | S | 180 |
| CCA | GCA | ATT | AGG | GCG | GGT | AAA | GAC | GCA | 754 |
| P | A | I | R | A | G | K | D | A | 189 |
| GCA | TCA | GCT | GTG | TCG | AAA | TTT | GGC | AAC | 772 |
| A | S | A | V | S | K | F | G | N | 198 |
| TAT | AAT | CAT | ACA | CAA | TTG | CTG | GGC | CAG | 790 |
| Y | N | H | T | Q | L | L | G | Q | 207 |
| CTT | CAA | GCA | GTA | AAC | CCT | AAC | GCG | GGC | 808 |
| L | Q | A | V | N | P | N | A | G | 216 |
| AAT | AGA | GGA | CAA | GTA | AAT | AAA | AAT | AGT | 826 |
| N | R | G | Q | V | N | K | N | S | 225 |

FIG. 9c

| | | | | | | | | | |
|---|---|---|---|---|---|---|---|---|---|
| GCG | GTC | TCA | CAA | AAT | ATG | GTG | ATG | ACT | 848 |
| A | V | S | Q | N | M | V | M | T | 234 |
| ACT | GGT | GAT | GTA | ATT | GCA | TCC | TCT | TAC | 862 |
| T | G | D | V | I | A | S | S | Y | 243 |
| GCA | CTT | GGT | ATT | GAC | CAG | GGA | CAG | ACT | 880 |
| A | L | G | I | D | Q | G | Q | T | 252 |
| ATT | GAA | GCA | ACC | TTT | ACT | AAT | CCT | GTG | 898 |
| I | E | A | T | F | T | N | P | V | 261 |
| GTT | AGC | ACC | ACC | CAG | TGG | AGT | GCT | CCG | 916 |
| V | S | T | T | Q | W | S | A | P | 270 |
| CTG | AAC | GTG | GCA | GTA | ACT | TAT | AAC | taa | 934 |
| L | N | V | A | V | T | Y | N | | 278 |

ttggcttgacaatttgtcagcctgtagttaactga 970 tataaagcaatccggctgcgatgtgagtatatttt 1006 attatataaatatattttgtatcgcatg 1036

FIG. 9d 10 18 45 57

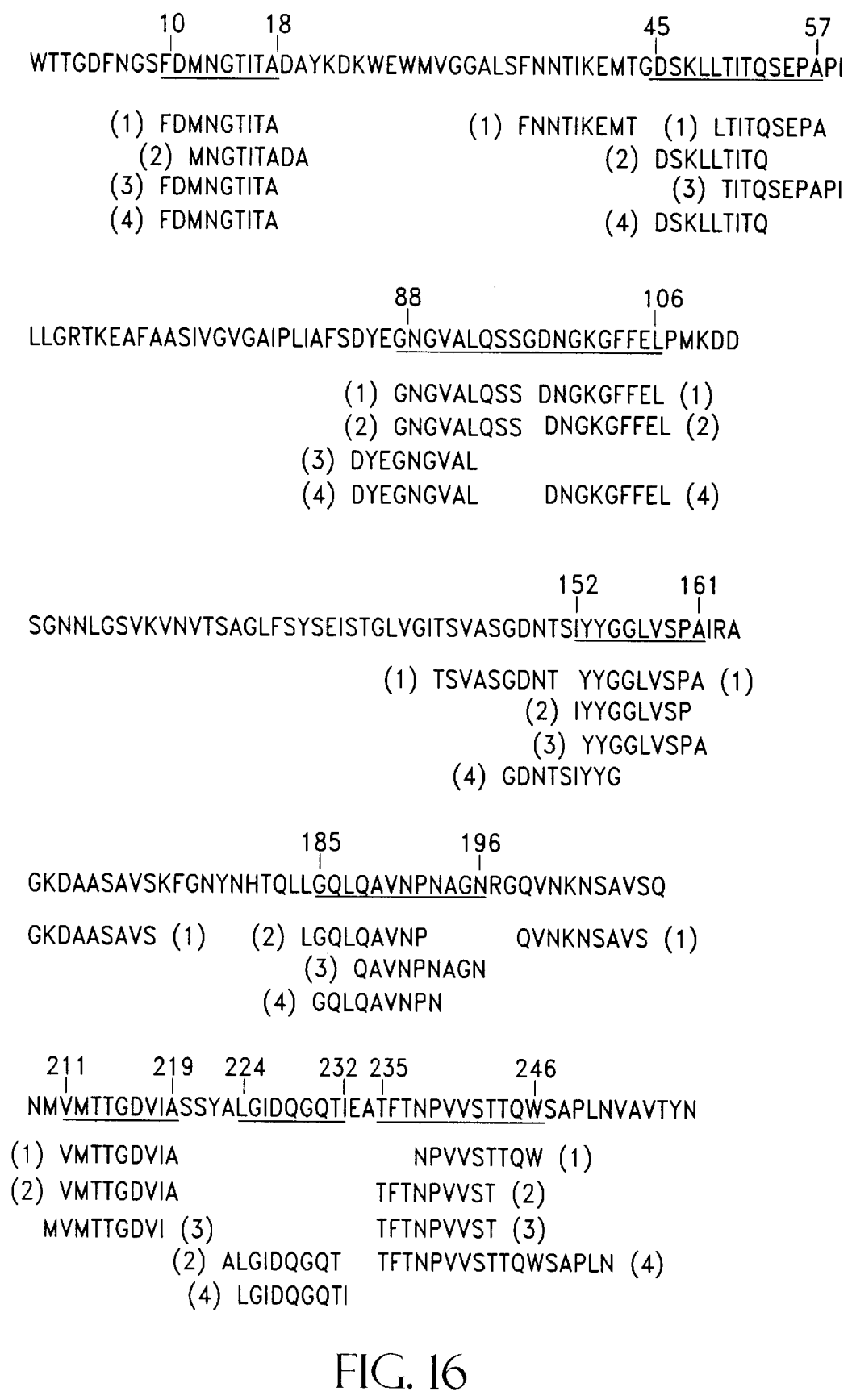

WTTGDFNGSFDMNGTITADAYKDKWEWMVGGALSFNNTIKEMTGDSKLLTITQSEPAPI (1) FDMNGTITA
(2) MNGTITADA
(3) FDMNGTITA
(4) FDMNGTITA (1) FNNTIKEMT
(1) LTITQSEPA
(2) DSKLLTITQ
(3) TITQSEPAPI
(4) DSKLLTITQ 88 106

LLGRTKEAFAASIVGVGAIPLIAFSDYEGNGVALQSSGDNGKGFFELPMKDD (1) GNGVALQSS DNGKGFFEL (1)
(2) GNGVALQSS DNGKGFFEL (2)
(3) DYEGNGVAL
(4) DYEGNGVAL DNGKGFFEL (4)

152 161

SGNNLGSVKVNVTSAGLFSYSEISTGLVGITSVASGDNTSIYYGGLVSPAIRA (1) TSVASGDNT YYGGLVSPA (1)
(2) IYYGGLVSP
(3) YYGGLVSPA
(4) GDNTSIYYG 185 196

GKDAASAVSKFGNYNHTQLLGQLQAVNPNAGNRGQVNKNSAVSQ

GKDAASAVS (1)
(2) LGQLQAVNP
QVNKNSAVS (1)
(3) QAVNPNAGN
(4) GQLQAVNPN 211 219 224 232 235 246

NMVMTTGDVIASSYALGIDQGQTIEATFTNPVVSTTQWSAPLNVAVTYN (1) VMTTGDVIA
(2) VMTTGDVIA
MVMTTGDVI (3)
(2) ALGIDQGQT
(4) LGIDQGQTI

NPVVSTTQW (1)
TFTNPVVST (2)
TFTNPVVST (3)
TFTNPVVSTTQWSAPLN (4)

FIG. 16

WTTGDFNGSFDMNGTITADAYKDKWEWMVGGALSFNNTIKEMTGDSKLLTITQSEPAPI 83 91

LLGRTKEAFAASIVGVGAIPLIAFSDYEGNGVALQSSGDNGKGFFELPMKDD

FSDYEGNGV (S1)

145 153 156 164

SGNNLGSVKVNVTSAGLFSYSEISTGLVGITSVASGDNTSIYYGGLVSPAIRA (N2) ASGDNTSIY GLVSPAIRA (S1)

176 196

GKDAASAVSKFGNYNHTQLLGQLQAVNPNAGNRGQVNKNSAVSQ (S1) GNYNHTQLL QAVNPNAGN (N1)

(N1) TQLLGQLQA

QAVNPNAGN (N2)

235 243

NMVMTTGDVIASSYALGIDQGQTIEATFTNPVVSTTQWSAPLNVAVTYN

TFTNPVVST (N1)

FIG. 17

```
1         10        20        30        40   Y    50        60
|         |         |         |         |        |         |
WTTGDFNGSFDMNGTITADAYKDKWEWMVGGALSFNNTIKEMT GDSKLLTITQSEPA PIL
                                           PEPTIDE Y-15-A

         70        80        90   Y   100       110       120
         |         |         |        |         |         |
LGRTKEAFAASIVGVGAIPLIAFSDYEGNGVALQSS GDNGKGFFELPMKD DSGNNLGSVK
                                    PEPTIDE Y-15-D

        130       140       150       160       170       180
         |         |         |         |         |         |
VNVTSAGLFSYSEISTGLVGITSVASG DNTSIYYGGLVSPAI RAGKDAASAVSKFG NYNH
                           PEPTIDE D-15-I

              190       200       210       220       230
               |         |         |         |         |
TQLL GQLQAVNPNAGNRGQ VNKNSAVSQNMVMTTGDVIASSYALGIDQGQ
    PEPTIDE G-15-Q

         240       250
          |         |
TIEA TFTNPVVSTTQWSAP LNVAVTYN
    PEPTIDE T-15-P
```

FIG. 19

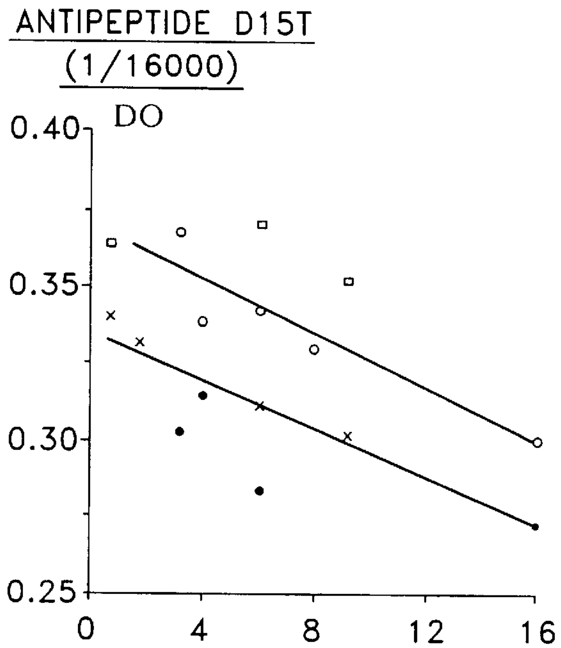
FIG. 20 A1
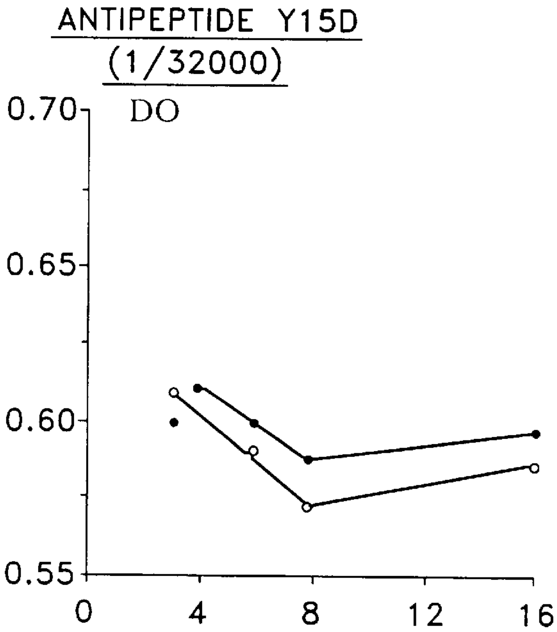
FIG. 20 A2
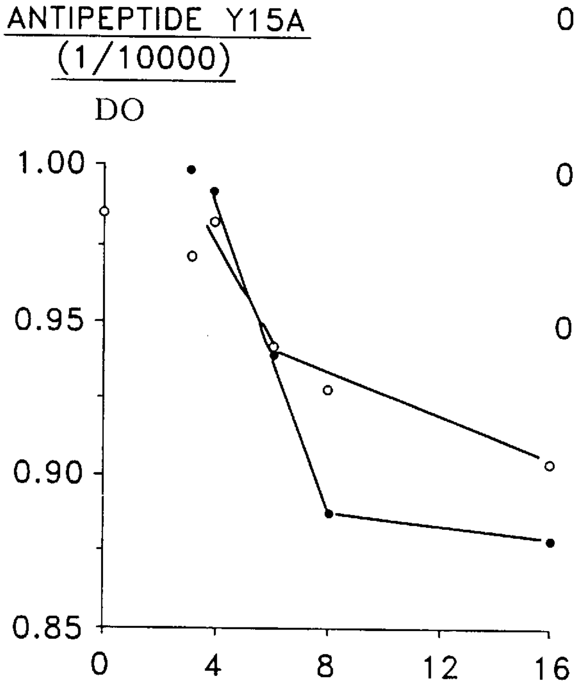
FIG. 20 A3

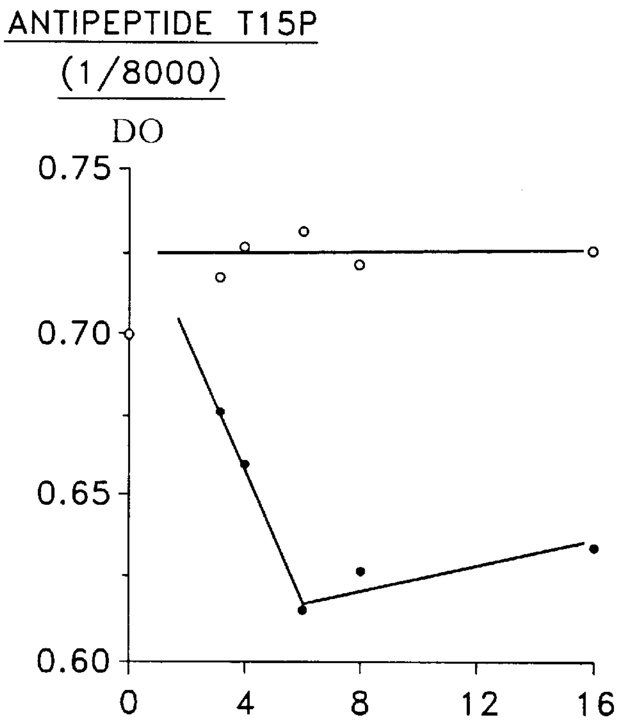
FIG. 20 B1
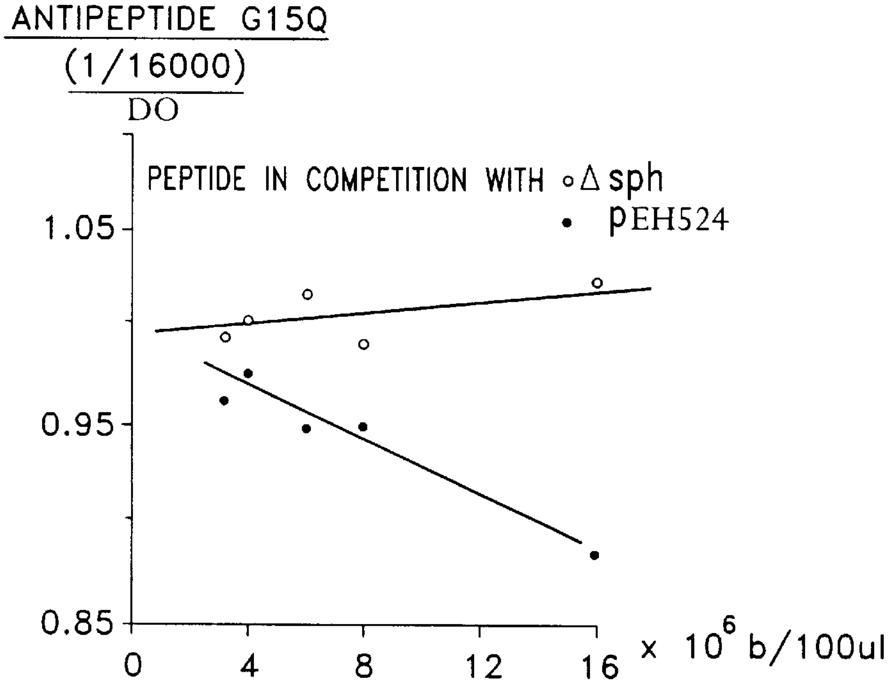
FIG. 20 B2

$Km^r$ CASSETTE WITH ITS MULTIPLE AND SYMMETRICAL RESTRICTION SITES (MCS)

Figure 25:
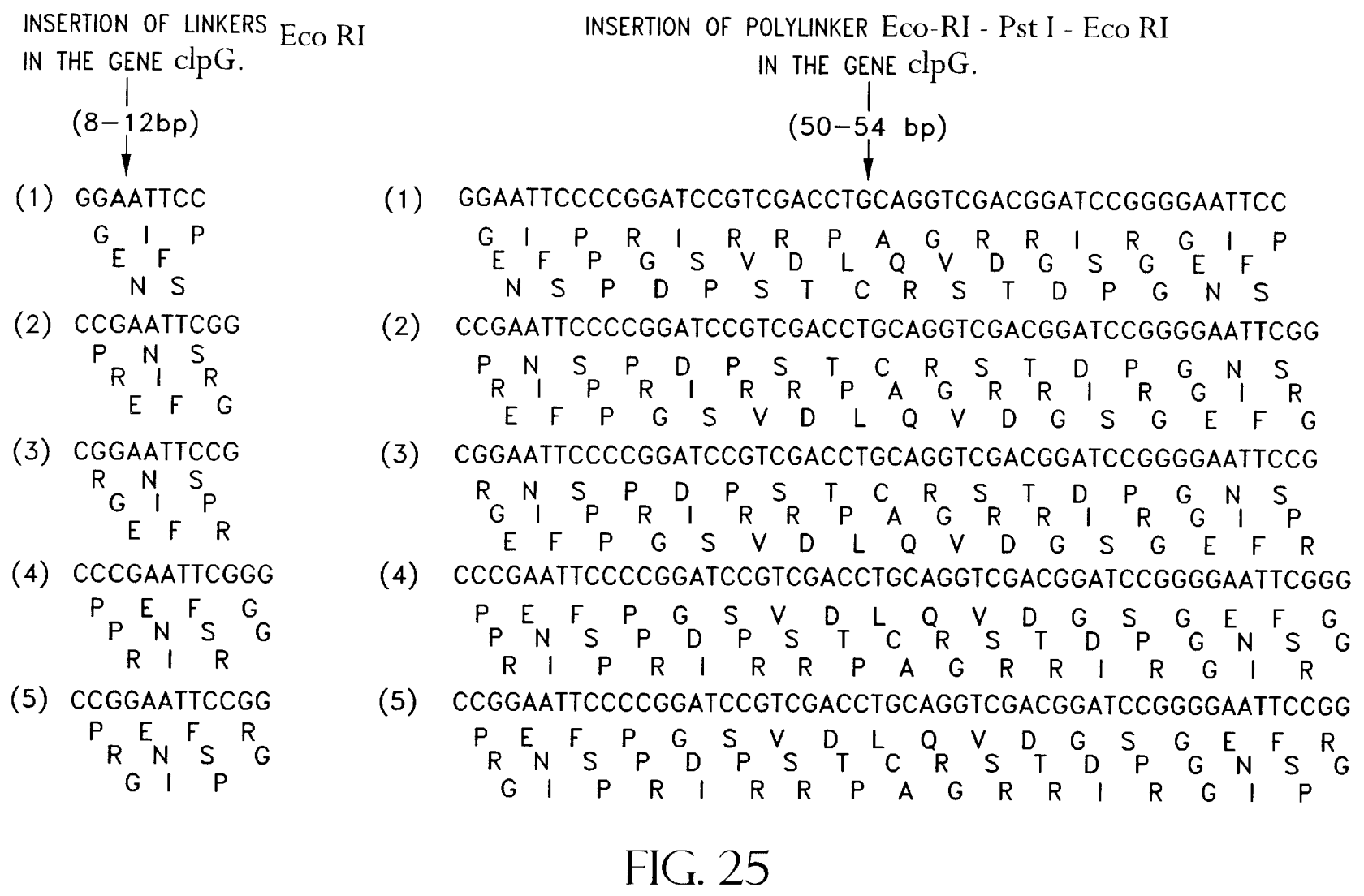

INSERTION OF LINKERS Eco RI IN THE GENE clpG.

(8–12bp)

(1) GGAATTCC

G I P
E F
N S (2) CCGAATTCGG

P N S
R I R
E F G (3) CGGAATTCCG

R N S
G I P
E F R (4) CCCGAATTCGGG

P E F G
P N S G
R I R (5) CCGGAATTCCGG

P E F R
R N S G
G I P

INSERTION OF POLYLINKER Eco-RI - Pst I - Eco RI IN THE GENE clpG.

(50–54 bp)

(1) GGAATTCCCCGGATCCGTCGACCTGCAGGTCGACGGATCCGGGGAATTCC

G I P R I R R P A G R R I R G I P
E F P G S V D L Q V D G S G E F
N S P D P S T C R S T D P G N S (2) CCGAATTCCCCGGATCCGTCGACCTGCAGGTCGACGGATCCGGGGAATTCGG

P N S P D P S T C R S T D P G N S
R I P R I R R P A G R R I R G I R
E F P G S V D L Q V D G S G E F G (3) CGGAATTCCCCGGATCCGTCGACCTGCAGGTCGACGGATCCGGGGAATTCCG

R N S P D P S T C R S T D P G N S
G I P R I R R P A G R R I R G I P
E F P G S V D L Q V D G S G E F R (4) CCCGAATTCCCCGGATCCGTCGACCTGCAGGTCGACGGATCCGGGGAATTCGGG

P E F P G S V D L Q V D G S G E F G
P N S P D P S T C R S T D P G N S G
R I P R I R R P A G R R I R G I R (5) CCGGAATTCCCCGGATCCGTCGACCTGCAGGTCGACGGATCCGGGGAATTCCGG

TGE/epitope C a)

```
N   V   T   S   A   S   S   F   F   S   Y   G   E   I   P   L   G   T   S   R   S
AAC.GTA.ACT.AGT.GCT.AGC.TCT.TTC.TTC.TCT.TAC.GGT.GAA.ATC.CCC.CTA.GGT.ACT.TCT.AGA.AGT.
TTG.CAT.TGA.TCA.CGA.TCG.AGA.AAG.AAG.AGA.ATG.CCA.CTT.TAG.GGG.GAT.CCA.TGA.AGA.TCT.TCA.
        Spe I                                               Avr II      Xba I
```

b)

Spe I-BglII

```
  S   S   S   F   F   S   Y   G   E   I   G
CT.AGT.AGT.TCA.TTC.TTT.AGT.TAT.GGT.GAA.ATT.GGA.
    A.TCA.AGT.AAG.AAA.TCA.ATA.CCA.CTT.TAA.CCT.CTA.G
Spe I                                       Bgl II
```

c)

Spe I-BglII

```
  S   S   S   F   F   S   Y   G   E   I   P
CT.AGT.AGT.TCA.TTC.TTT.AGT.TAT.GGT.GAA.ATT.CCA.
    A.TCA.AGT.AAG.AAA.TCA.ATA.CCA.CTT.TAA.GGT.CTA.G
Spe I                                       Bgl II
```

FIG. 27(a)

d)
Hpa I-Spc I

```
N   S   S   F   F   S   Y   G   E   I   P
AAC.AGT.TCA.TTC.TTT.AGT.TAT.GGT.GAA.ATT.CCT.A
TTG.TCA.AGT.AAG.AAA.TCA.ATA.CCA.CTT.TAA.GGA.TGA.TC
                                            Spe I
```

TGE/epitope A

Spe I-BglII

```
   S   M   K   R   S   G   Y   G   Q   P   I   A   G
CT.AGT.ATG.AAA.CGG.AGT.GGT.TAT.GGT.CAG.CCT.ATT.GCA.GGA.
     A.TAC.TTT.GCC.TCA.CCA.ATA.CCA.GTC.GGA.TAA.CGT.CCT.CTA.G
Spe I                                                 Bgl II
```

FIG. 27(b)

POLIO e)

Spe I-Bgl II

```
   S   D   N   P   A   S   T   T   N   K   D   K   G
CT.AGT.GAT.AAC.CCT.GCT.AGC.ACT.ACA.AAT.AAA.GAT.AAA.GGA.
     A.CTA.TTG.GGA.CGA.TCG.TGA.TGT.TTA.TTT.CTA.TTT.CCT.CTA.G
Spe I                                                Bgl II
```

f)

Hpa I-Spe I

```
  A   V   N   P   A   S   T   T   N   K   D   K   T   S   A
G.GCA.GTT.AAC.CCT.GCA.AGT.ACT.ACA.AAT.AAA.GAT.AAA.ACT.AGT.GCG.G
C.CGT.CAA.TTG.GGA.CGT.TCA.TGA.TGT.TTA.TTT.CTA.TTT.TGA.TCA.CGC.C
      Hpa I                                          Spe I
```

FIG. 27(c)

FMDV g)

Hpa I-Spe I

```
 N   Y   K   Q   K   I   I   A   P   A   Q   K
AAC.TAT.AAA.CAG.AAA.ATT.ATT.GCA.CCT.GCA.CAG.AAA.A
TTG.ATA.TTT.GTC.TTT.TAA.TAA.CGT.GGA.CGT.GTC.TTT.TGA.TC
                                                ______
                                                Spe I
```

ROTA

Spe I-Bgl II

```
    S   I   R   N   W   N   F   D   F   G   L   L   G
CT.AGT.ATT.AGA.AAT.TGG.AAC.TTT.GAT.TTT.GGT.CTG.TTA.GGA.
 A.TCA.TAA.TCT.TTA.ACC.TTG.AAA.CTA.AAA.CCA.GAC.AAT.CCT.CTA.G
_____                                                ______
Spe I                                                Bgl II
```

FIG. 27(d)

```
         110
F E L P M K D D S G N N L G S V K
TTT GAA TTG CCC ATG AAA GAT GAT AGT GGA AAT AAT CTC GGT AGC GTA AAA
```

| 123 | VARIABLE REGION 2 | 151 |
|---|---|---|

```
              130                      140               150
V  N  VTSAGLF S    Y SEIST  G    L  V  GI T    S  VAS GDNTS
GTT.AAT        TAT.AGT       GGT.TTA.GTT    ACT.TCT
```

```
 V   N*
GTT.AAC                                                        MUTANT 1
 ‾‾‾‾‾
 Hpa I
```

```
 V   N  —10aa—  *T  S
         *       * *
GTT.AAC         ACT.AGT                                        MUTANT 2
 ‾‾‾‾‾           ‾‾‾‾‾
 Hpa I           Spe I
```

```
 V   N ——16aa——          G   L  V
         *                * *
GTT.AAC                 GGA.CTA.GTT                            MUTANT 3
 ‾‾‾‾‾                   ‾‾‾‾‾‾‾
 Hpa I                    Spe I
```

```
 V   N ————21aa————————————  T   S
         *                    * *
GTT.AAC                     ACT.AGT                            MUTANT 4
 ‾‾‾‾‾                       ‾‾‾‾‾
 Hpa I                        Spe I
```

```
 V  N* —10aa— *T  S ——9aa—— T   S
         *     * *           * *
GTT.AAC       ACT.AGT       ACT.AGT                            MUTANT 5
 ‾‾‾‾‾         ‾‾‾‾‾         ‾‾‾‾‾
 Hpa I         Spe I         Spe I
                       △
```

```
 V   N —10aa— *T  S
         *     * *
GTT.AAC       ACT.AGT                                          MUTANT 6
 ‾‾‾‾‾         ‾‾‾‾‾
 Hpa I         Spe I
```

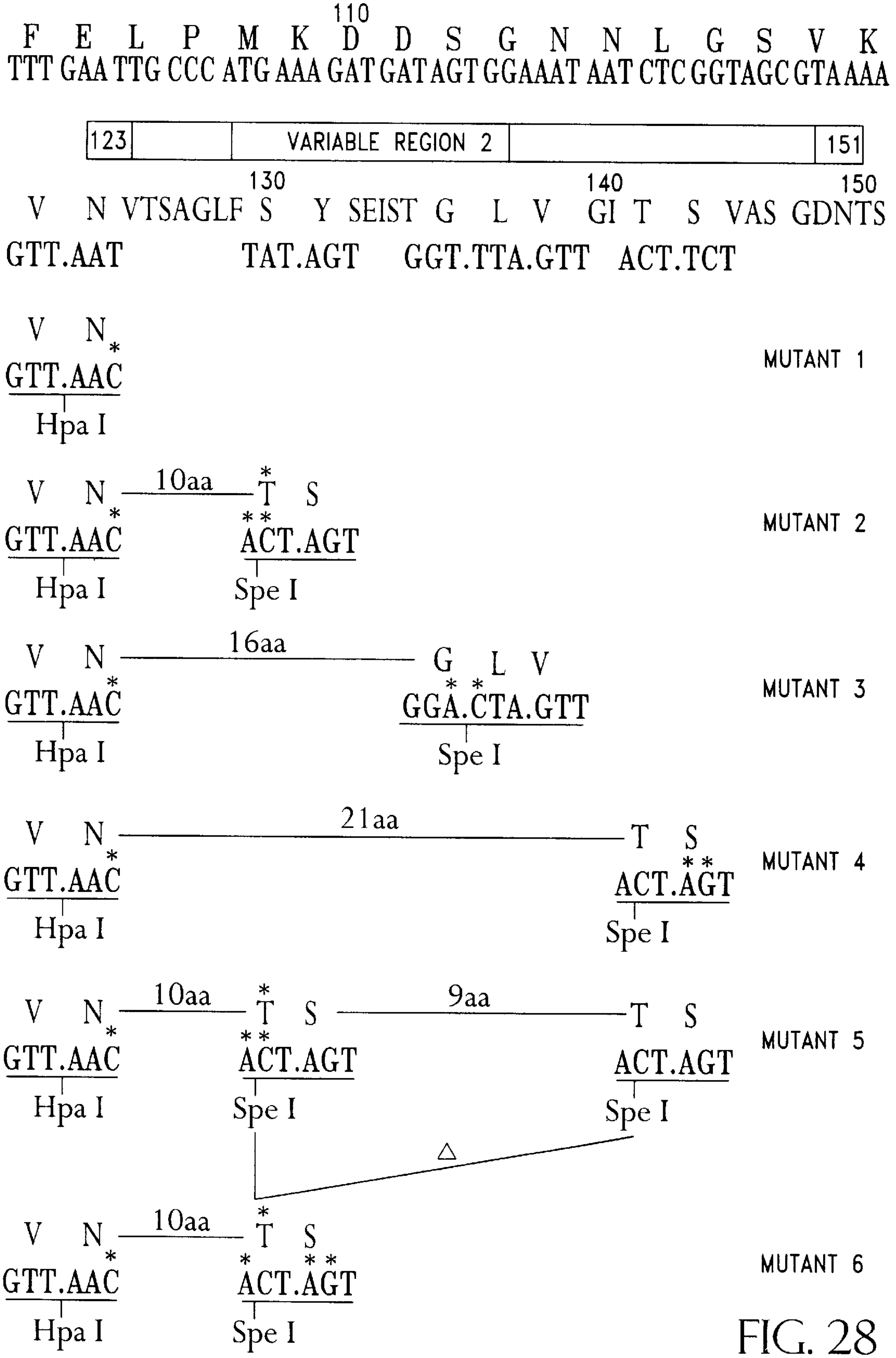

FIG. 28 a

VARIABLE REGION 2

MUTANT 2 — Hpa I ── Spe I
└── 9aa ──┘

| | | SYNTHESIS OF THE PROTEIN | PRODUCTION OF CAPSULE |
|---|---|---|---|
| TGE/C pGC 1 | ◁—16aa—▷ | + | − |
| FMDV pF 1 | ——12aa—— | + | − |

b

VARIABLE REGION 2

MUTANT 3 — Hpa I ── Spe I
└── 15aa ──┘

| | | SYNTHESIS OF THE PROTEIN | PRODUCTION OF CAPSULE |
|---|---|---|---|
| TGE/C pGC 32 | ——15aa—— | + | − |

a
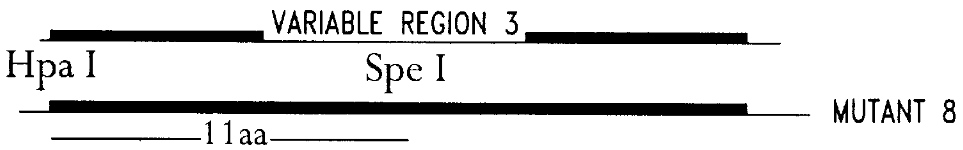
| | | SYNTHESIS OF THE PROTEIN | PRODUCTION OF CAPSULE | ACCESSIBILITY OF THE EPITOPE |
|---|---|---|---|---|
| TGE/C GP 684 | 10aa | +++ | +++ | ND |
| POLIO F688 | 10aa | ++ | ++ | +/− |
| FMDV F681 | 12aa | ++ | ++ | + |
b
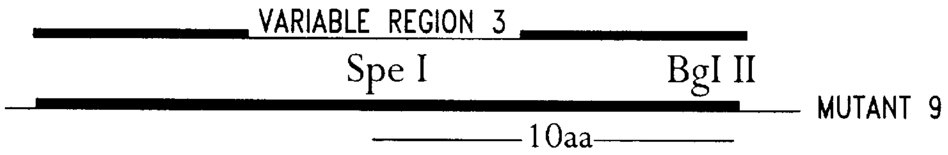
| | | SYNTHESIS OF THE PROTEIN | PRODUCTION OF CAPSULE | ACCESSIBILITY OF THE EPITOPE |
|---|---|---|---|---|
| TGE/C GP 105 | 10aa | +++ | +++ | ND |
| GP 103 | 10aa | +++ | +++ | + |
| POLIO P 101 | 12aa | +++ | +++ | +/− |
FIG. 34

LOG2 OF THE INVERSE OF THE DILUTION OF ANTIBODIES YIELDING AN OD>0.3
INVERSE OF THE DILUTION OF ANTIBODIES YIELDING AN OD>0.3

PROTEIN CS31A
m*=17.4 ±1.3
:400
m=15,3±0,6
X8
m=12,3±0,6
m=11,7±2
m=11,6±1,8
=

VIRUS TGE
m=10.8±1
m=11±0.6
m=12.1±0.6
X10
x100
:50
m=7.5±1,4
m=5.4±0.5

PEPTIDE A
m=2.6±3.7
m=3±4.1
0

PEPTIDE C
m=7.8±1.5
m=8.4±0.9
X100
:80
m=2.6±3.5
0 21 35 45 150 157 DAYS
IMMUNIZATION
RECOMBINANT PROTEIN IN NATIVE FORM [20 μg WITH Al (OH) 3]
VIRUS TGE (PERDUE STRAIN)

LOG2 OF THE INVERSE OF THE DILUTION OF ANTIBODIES YIELDING AN OD>0.3
INVERSE OF THE DILUTION OF ANTIBODIES YIELDING AN OD>0.3

PROTEIN CS31A
m=11,3±,1
m*=17±0
m=15,6±0,6

VIRUS TGE
m=10.9±1.4
:100
m=8.6±4.8
x20
m=4.1±5.6

PEPTIDE A
m=7.6±1.9
:20
m=8.5±2.2
x37
m=3.2±4.4

PEPTIDE C
m=8.9±1.4
:8
m=8.5±3.5
x8
m=5.8±3.5
0 21 35 45 150 157 167 DAYS
IMMUNIZATION
RECOMBINANT PROTEIN IN DENATURED FORM
[20 μg WITH AIF]

a: PROTE IN CS31A b: VIRUS c: PEPTIDE d: PEPTIDE C

LOG2 OF THE INVERSE OF THE DILUTION OF ANTIBODIES YIELDING AN OD>0.3
INVERSE OF THE DILUTION OF ANTIBODIES YIELDING AN OD>0.3

PROTEIN CS31A
m*=11.8+0.4

VIRUS
m=10.4±0.5

PEPTIDE
0
0

PEPTIDE C
m=5.2±1.8
m=8±1
0 21 35 45 203 209
IMMUNIZATION
RECOMBINANT BACTERIA IN SALINE SOLUTION

SEQUENCE LISTING

```
(1) GENERAL INFORMATION:

   (iii) NUMBER OF SEQUENCES: 115


(2) INFORMATION FOR SEQ ID NO:1:

     (i) SEQUENCE CHARACTERISTICS:
          (A) LENGTH: 1318 base pairs
          (B) TYPE: nucleic acid
          (C) STRANDEDNESS: single
          (D) TOPOLOGY: linear

    (ii) MOLECULE TYPE: cDNA

    (ix) FEATURE:
          (A) NAME/KEY: CDS
          (B) LOCATION: 384..1217

    (ix) FEATURE:
          (A) NAME/KEY: mat_peptide
          (B) LOCATION: 447..1217

    (xi) SEQUENCE DESCRIPTION: SEQ ID NO:1:

CTCAGTGCCA GACAGCAGGG TGAGATGTGG TGATAAGCGT GCCGAGGCAA AGAAACAGGT      60

TGAGTTAAGA ACGATGCACC GGCAGAGCTG AAGTCCCGGT CAGTTACCGG GAAATCTTGC     120

AGATAGCACT GCAGGTGGAA GACTGAGAAT TTATCTCCGA CAACAGATGC AATACATCCC     180

TGACTCCGGA ATGGGTCATA TTGGTAAAGG GATTTACCGT ATTTTTAAAA GGGAATAACG     240

CAAAACTATT CTGAATTAAA CACTGTGTTT AATTAAAGCG GCTATTTAAA TAAGTCCACA     300

GGGGATAGTT TTGCGGTAAT TCCGGAAAAA TAAGGATTGC CGATATCGAT TTATTATTTG     360

TGAAATATAA AGGAATTTAT TTT ATG AAA AAG ACT CTG ATT GCA CTG GCT        410
                          Met Lys Lys Thr Leu Ile Ala Leu Ala
                          -21 -20                 -15

GTG GCT GTT TCG GCA GTA TCA GGT GCG GCG CAT GCG TGG ACC ACT GGT        458
Val Ala Val Ser Ala Val Ser Gly Ala Ala His Ala Trp Thr Thr Gly
        -10                 -5                  1

GAT TTT AAT GGT TCA TTT GAT ATG AAT GGC ACA ATT ACT GCT GAT GCG        506
Asp Phe Asn Gly Ser Phe Asp Met Asn Gly Thr Ile Thr Ala Asp Ala
  5                  10                  15                  20

TAT AAA GAC AAA TGG GAA TGG ATG GTT GGG GGC GCT CTC TCC TTC AAC        554
Tyr Lys Asp Lys Trp Glu Trp Met Val Gly Gly Ala Leu Ser Phe Asn
                 25                  30                  35

AAC ACT ATC AAG GAA ATG ACA GGT GAC AGT AAG CTG CTG ACC ATC ACT        602
```

-continued

```
Asn Thr Ile Lys Glu Met Thr Gly Asp Ser Lys Leu Leu Thr Ile Thr
            40                  45                  50

CAG TCT GAA CCA GCT CCT ATT CTT TTA GGG CGC ACA AAA GAG GCG TTT      650
Gln Ser Glu Pro Ala Pro Ile Leu Leu Gly Arg Thr Lys Glu Ala Phe
        55                  60                  65

GCA GCA TCG ATT GTT GGT GTT GGT GCA ATT CCT TTA ATT GCG TTC AGT      698
Ala Ala Ser Ile Val Gly Val Gly Ala Ile Pro Leu Ile Ala Phe Ser
    70                  75                  80

GAT TAT GAA GGG AAC GGA GTT GCC TTA CAG AGT TCT GGG GAT AAC GGT      746
Asp Tyr Glu Gly Asn Gly Val Ala Leu Gln Ser Ser Gly Asp Asn Gly
 85                 90                  95                 100

AAG GGG TTC TTT GAA TTG CCC ATG AAA GAT GAT AGT GGA AAT AAT CTC      794
Lys Gly Phe Phe Glu Leu Pro Met Lys Asp Asp Ser Gly Asn Asn Leu
                105                 110                 115

GGT AGC GTA AAA GTT AAT GTT ACT TCT GCT GGC CTG TTT TCC TAT AGT      842
Gly Ser Val Lys Val Asn Val Thr Ser Ala Gly Leu Phe Ser Tyr Ser
            120                 125                 130

GAA ATA TCA ACA GGT TTA GTT GGT ATA ACT TCT GTT GCC AGT GGC GAT      890
Glu Ile Ser Thr Gly Leu Val Gly Ile Thr Ser Val Ala Ser Gly Asp
        135                 140                 145

AAT ACA AGT ATT TAT TAT GGT GGT CTG GTG TCG CCA GCA ATT AGG GCG      938
Asn Thr Ser Ile Tyr Tyr Gly Gly Leu Val Ser Pro Ala Ile Arg Ala
    150                 155                 160

GGT AAA GAC GCA GCA TCA GCT GTG TCG AAA TTT GGC AAC TAT AAT CAT      986
Gly Lys Asp Ala Ala Ser Ala Val Ser Lys Phe Gly Asn Tyr Asn His
165                 170                 175                 180

ACA CAA TTG CTG GGC CAG CTT CAA GCA GTA AAC CCT AAC GCG GGC AAT     1034
Thr Gln Leu Leu Gly Gln Leu Gln Ala Val Asn Pro Asn Ala Gly Asn
                185                 190                 195

AGA GGA CAA GTA AAT AAA AAT AGT GCG GTC TCA CAA AAT ATG GTG ATG     1082
Arg Gly Gln Val Asn Lys Asn Ser Ala Val Ser Gln Asn Met Val Met
            200                 205                 210

ACT ACT GGT GAT GTA ATT GCA TCC TCT TAC GCA CTT GGT ATT GAC CAG     1130
Thr Thr Gly Asp Val Ile Ala Ser Ser Tyr Ala Leu Gly Ile Asp Gln
        215                 220                 225

GGA CAG ACT ATT GAA GCA ACC TTT ACT AAT CCT GTG GTT AGC ACC ACC     1178
Gly Gln Thr Ile Glu Ala Thr Phe Thr Asn Pro Val Val Ser Thr Thr
    230                 235                 240

CAG TGG AGT GCT CCG CTG AAC GTG GCA GTA ACT TAT AAC TAATTGGCTT      1227
Gln Trp Ser Ala Pro Leu Asn Val Ala Val Thr Tyr Asn
245                 250                 255

GACAATTTGT CAGCCTGTAG TTAACTGATA TAAAGCAATC CGGCTGCGAT GTGAGTATAT   1287

TTTATTATAT AAATATATTT TGTATCGCAT G                                  1318
```

(2) INFORMATION FOR SEQ ID NO:2:

(i) SEQUENCE CHARACTERISTICS:
(A) LENGTH: 278 amino acids
(B) TYPE: amino acid
(D) TOPOLOGY: linear (ii) MOLECULE TYPE: protein (xi) SEQUENCE DESCRIPTION: SEQ ID NO:2:

```
Met Lys Lys Thr Leu Ile Ala Leu Ala Val Ala Val Ser Ala Val Ser
-21 -20               -15                 -10

Gly Ala Ala His Ala Trp Thr Thr Gly Asp Phe Asn Gly Ser Phe Asp
 -5                   1               5                  10

Met Asn Gly Thr Ile Thr Ala Asp Ala Tyr Lys Asp Lys Trp Glu Trp
            15                  20                  25
```

-continued

```
Met Val Gly Gly Ala Leu Ser Phe Asn Asn Thr Ile Lys Glu Met Thr
        30                  35                  40

Gly Asp Ser Lys Leu Leu Thr Ile Thr Gln Ser Glu Pro Ala Pro Ile
    45                  50                  55

Leu Leu Gly Arg Thr Lys Glu Ala Phe Ala Ala Ser Ile Val Gly Val
 60                  65                  70                  75

Gly Ala Ile Pro Leu Ile Ala Phe Ser Asp Tyr Glu Gly Asn Gly Val
                80                  85                  90

Ala Leu Gln Ser Ser Gly Asp Asn Gly Lys Gly Phe Phe Glu Leu Pro
            95                 100                 105

Met Lys Asp Asp Ser Gly Asn Asn Leu Gly Ser Val Lys Val Asn Val
       110                 115                 120

Thr Ser Ala Gly Leu Phe Ser Tyr Ser Glu Ile Ser Thr Gly Leu Val
    125                 130                 135

Gly Ile Thr Ser Val Ala Ser Gly Asp Asn Thr Ser Ile Tyr Tyr Gly
140                 145                 150                 155

Gly Leu Val Ser Pro Ala Ile Arg Ala Gly Lys Asp Ala Ala Ser Ala
                160                 165                 170

Val Ser Lys Phe Gly Asn Tyr Asn His Thr Gln Leu Leu Gly Gln Leu
            175                 180                 185

Gln Ala Val Asn Pro Asn Ala Gly Asn Arg Gly Gln Val Asn Lys Asn
        190                 195                 200

Ser Ala Val Ser Gln Asn Met Val Met Thr Thr Gly Asp Val Ile Ala
    205                 210                 215

Ser Ser Tyr Ala Leu Gly Ile Asp Gln Gly Gln Thr Ile Glu Ala Thr
220                 225                 230                 235

Phe Thr Asn Pro Val Val Ser Thr Thr Gln Trp Ser Ala Pro Leu Asn
                240                 245                 250

Val Ala Val Thr Tyr Asn
            255
```

(2) INFORMATION FOR SEQ ID NO:3:

(i) SEQUENCE CHARACTERISTICS:
(A) LENGTH: 284 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:3:

```
Met Lys Lys Thr Leu Ile Ala Leu Ala Ile Ala Val Ser Ala Ala Ser
1               5                   10                  15

Gly Met Ala His Ala Trp Met Thr Gly Asp Phe Asn Gly Ser Val Asp
            20                  25                  30

Ile Gly Gly Ser Ile Thr Ala Asp Asp Tyr Arg Gln Lys Trp Glu Trp
        35                  40                  45

Lys Val Gly Thr Gly Leu Asn Gly Phe Gly Ser Val Leu Asn Asp Leu
    50                  55                  60

Thr Asn Gly Gly Thr Lys Leu Thr Ile Thr Val Thr Gly Asn Lys Pro
65                  70                  75                  80

Ile Leu Leu Gly Arg Thr Lys Glu Ala Phe Ala Thr Pro Val Thr Ser
                85                  90                  95

Gly Val Asp Gly Ile Pro His Ile Ala Phe Thr Asp Tyr Glu Gly Ala
            100                 105                 110
```

-continued

```
Ser Val Glu Leu Arg Asn Pro Asp Gly Glu Thr Glu Lys Gly Leu Ala
        115                 120                 125

Tyr Phe Val Leu Pro Met Lys Asn Ala Glu Gly Thr Lys Val Gly Ser
    130                 135                 140

Val Lys Val Asn Ala Ser Tyr Ala Gly Ala Leu Gly Arg Gly Gly Val
145                 150                 155                 160

Thr Ser Ala Asp Gly Glu Leu Met Ser Leu Phe Ala Glu Gly Ser His
                165                 170                 175

Ala Ile Phe Tyr Gly Gly Leu Pro Thr Asn Val Lys Asn Ser Glu Leu
            180                 185                 190

Lys Gly Gly Ser Ala Ala Ala Ala Arg Thr Glu Leu Phe Gly Ser Leu
        195                 200                 205

Ser Lys Asn Asp Ile Leu Gly Gln Ile Gln Arg Val Asn Ala Asn Thr
    210                 215                 220

Ser Leu Val Asn Val Pro Gly Ser Phe Asn Glu Asn Met Ala Tyr Thr
225                 230                 235                 240

Asp Gly Val Val Val Ser Val Ala Tyr Ala Leu Gly Ile Ala Asn Gly
                245                 250                 255

Gln Thr Ile Glu Ala Thr Phe Asn Gln Ala Val Thr Thr Ser Thr Gln
            260                 265                 270

Trp Ser Ala Pro Leu Asn Val Ala Ile Thr Tyr Tyr
        275                 280
```

(2) INFORMATION FOR SEQ ID NO:4:

(i) SEQUENCE CHARACTERISTICS:
(A) LENGTH: 274 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:4:

```
Met Lys Lys Thr Leu Ile Ala Leu Ala Val Ala Val Ser Ala Ala Val
1               5                   10                  15

Ser Gly Ser Val Met Ala Ala Asp Trp Thr Glu Gly Gln Pro Gly Asp
            20                  25                  30

Ile Ile Ile Gly Gly Glu Ile Thr Ser Pro Ser Val Lys Trp Leu Trp
        35                  40                  45

Lys Thr Gly Glu Gly Leu Ser Ser Phe Ser Asn Thr Thr Asn Glu Ile
    50                  55                  60

Val Lys Arg Lys Leu Asn Ile Ser Val Pro Thr Asp Glu Leu Phe Leu
65                  70                  75                  80

Ala Ala Lys Met Ser Asp Gly Ile Lys Gly Val Phe Val Gly Asn Thr
                85                  90                  95

Leu Ile Pro Lys Ile Glu Met Ala Ser Tyr Asp Gly Ser Val Ile Thr
            100                 105                 110

Ser Phe Thr Ser Asn Thr Ala Met Asp Ile Ala Val Lys Val Lys Asn
        115                 120                 125

Ser Gly Asp Asn Thr Glu Leu Gly Thr Leu Ser Val Pro Leu Ser Phe
    130                 135                 140

Gly Ala Ala Val Thr Ile Phe Asp Gly Asn Thr Thr Asp Ser Ala Val
145                 150                 155                 160

Ala His Ile Thr Ser Gly Ser Ala Gly Thr Val Phe Glu Gly Leu Val
                165                 170                 175
```

-continued

```
Asn Pro Gly Arg Phe Thr Asp Gln Asn Ile Ala Tyr Lys Trp Asn Gly
            180                 185                 190

Leu Ser Lys Ala Glu Met Ala Gly Tyr Val Glu Lys Leu Met Pro Gly
        195                 200                 205

Lys Ser Ser Thr Ser Tyr Ser Gly Phe His Asn Trp Asp Asp Leu Ser
    210                 215                 220

His Pro Asn Tyr Thr Ser Ala Asp Lys Ala Ser Tyr Leu Ser Tyr Gly
225                 230                 235                 240

Ser Gly Val Ser Ala Gly Ser Thr Leu Val Met Asn Leu Asn Lys Asp
                245                 250                 255

Val Ala Gly Arg Leu Glu Trp Val Ala Pro Val Thr Ile Thr Val Ile
            260                 265                 270

Tyr Ser
```

(2) INFORMATION FOR SEQ ID NO:5:

(i) SEQUENCE CHARACTERISTICS:
(A) LENGTH: 14 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:5:

```
Gly Asp Ser Lys Leu Leu Thr Ile Thr Gln Ser Glu Pro Ala
1               5                   10
```

(2) INFORMATION FOR SEQ ID NO:6:

(i) SEQUENCE CHARACTERISTICS:
(A) LENGTH: 14 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:6:

```
Gly Asp Asn Gly Lys Gly Phe Phe Glu Leu Pro Met Lys Asp
1               5                   10
```

(2) INFORMATION FOR SEQ ID NO:7:

(i) SEQUENCE CHARACTERISTICS:
(A) LENGTH: 15 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:7:

```
Asp Asn Thr Ser Ile Tyr Tyr Gly Gly Leu Val Ser Pro Ala Ile
1               5                   10                  15
```

(2) INFORMATION FOR SEQ ID NO:8:

(i) SEQUENCE CHARACTERISTICS:
(A) LENGTH: 15 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:8:

```
Gly Gln Leu Gln Ala Val Asn Pro Asn Ala Gly Asn Arg Gly Gln
1               5                   10                  15
```

(2) INFORMATION FOR SEQ ID NO:9:

(i) SEQUENCE CHARACTERISTICS:
(A) LENGTH: 15 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:9:

```
Thr Phe Thr Asn Pro Val Val Ser Thr Thr Gln Trp Ser Ala Pro
1               5                   10                  15
```

(2) INFORMATION FOR SEQ ID NO:10:

(i) SEQUENCE CHARACTERISTICS:
(A) LENGTH: 9 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:10:

```
Gly Asp Ser Lys Leu Leu Thr Ile Thr
1               5
```

(2) INFORMATION FOR SEQ ID NO:11:

(i) SEQUENCE CHARACTERISTICS:
(A) LENGTH: 9 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:11:

```
Phe Glu Leu Pro Met Lys Asp Asp Ser
1               5
```

(2) INFORMATION FOR SEQ ID NO:12:

(i) SEQUENCE CHARACTERISTICS:
(A) LENGTH: 10 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:12:

```
Ile Tyr Tyr Gly Gly Leu Val Ser Pro Ala
1               5                   10
```

(2) INFORMATION FOR SEQ ID NO:13:

(i) SEQUENCE CHARACTERISTICS:
(A) LENGTH: 9 amino acids
(B) TYPE: amino acid
(C) STRANDEDNESS:
(D) TOPOLOGY: linear -continued (ii) MOLECULE TYPE: peptide (xi) SEQUENCE DESCRIPTION: SEQ ID NO:13:

Gln Leu Gln Ala Val Asn Pro Asn Ala
1 5

(2) INFORMATION FOR SEQ ID NO:14:

(i) SEQUENCE CHARACTERISTICS:
(A) LENGTH: 9 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:14:

Ser Thr Thr Gln Trp Ser Ala Pro Leu
1 5

(2) INFORMATION FOR SEQ ID NO:15:

(i) SEQUENCE CHARACTERISTICS:
(A) LENGTH: 9 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:15:

Phe Asp Met Asn Gly Thr Ile Thr Ala
1 5

(2) INFORMATION FOR SEQ ID NO:16:

(i) SEQUENCE CHARACTERISTICS:
(A) LENGTH: 9 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:16:

Met Asn Gly Thr Ile Thr Ala Asp Ala
1 5

(2) INFORMATION FOR SEQ ID NO:17:

(i) SEQUENCE CHARACTERISTICS:
(A) LENGTH: 9 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:17:

Phe Asn Asn Thr Ile Lys Glu Met Thr
1 5

(2) INFORMATION FOR SEQ ID NO:18:

(i) SEQUENCE CHARACTERISTICS:
(A) LENGTH: 9 amino acids
(B) TYPE: amino acid
(C) STRANDEDNESS:
(D) TOPOLOGY: linear -continued (ii) MOLECULE TYPE: peptide (xi) SEQUENCE DESCRIPTION: SEQ ID NO:18:

Leu Thr Ile Thr Gln Ser Glu Pro Ala
1 5

(2) INFORMATION FOR SEQ ID NO:19:

(i) SEQUENCE CHARACTERISTICS:
(A) LENGTH: 10 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:19:

Asp Ser Lys Leu Leu Thr Ile Thr Thr Gln
1 5 10

(2) INFORMATION FOR SEQ ID NO:20:

(i) SEQUENCE CHARACTERISTICS:
(A) LENGTH: 9 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:20:

Val Gly Val Gly Ala Ile Pro Leu Ile
1 5

(2) INFORMATION FOR SEQ ID NO:21:

(i) SEQUENCE CHARACTERISTICS:
(A) LENGTH: 9 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:21:

Gly Asn Gly Val Ala Leu Gln Ser Ser
1 5

(2) INFORMATION FOR SEQ ID NO:22:

(i) SEQUENCE CHARACTERISTICS:
(A) LENGTH: 9 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:22:

Asp Asn Gly Lys Gly Phe Phe Glu Leu
1 5

(2) INFORMATION FOR SEQ ID NO:23:

(i) SEQUENCE CHARACTERISTICS:
(A) LENGTH: 8 amino acids
(B) TYPE: amino acid
(C) STRANDEDNESS:

-continued (D) TOPOLOGY: linear (ii) MOLECULE TYPE: peptide (xi) SEQUENCE DESCRIPTION: SEQ ID NO:23:

Thr Ser Val Ala Ser Gly Asn Thr
1 5

(2) INFORMATION FOR SEQ ID NO:24:

(i) SEQUENCE CHARACTERISTICS:
(A) LENGTH: 9 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:24:

Tyr Tyr Gly Gly Leu Val Ser Pro Ala
1 5

(2) INFORMATION FOR SEQ ID NO:25:

(i) SEQUENCE CHARACTERISTICS:
(A) LENGTH: 9 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:25:

Ile Tyr Tyr Gly Gly Leu Val Ser Pro
1 5

(2) INFORMATION FOR SEQ ID NO:26:

(i) SEQUENCE CHARACTERISTICS:
(A) LENGTH: 9 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:26:

Gly Lys Asp Ala Ala Ser Ala Val Ser
1 5

(2) INFORMATION FOR SEQ ID NO:27:

(i) SEQUENCE CHARACTERISTICS:
(A) LENGTH: 9 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:27:

Leu Gly Gln Leu Gln Ala Val Asn Pro
1 5

(2) INFORMATION FOR SEQ ID NO:28:

(i) SEQUENCE CHARACTERISTICS:
(A) LENGTH: 9 amino acids
(B) TYPE: amino acid

-continued (C) STRANDEDNESS:
(D) TOPOLOGY: linear (ii) MOLECULE TYPE: peptide (xi) SEQUENCE DESCRIPTION: SEQ ID NO:28:

Gln Val Asn Lys Asn Ser Ala Val Ser
1 5

(2) INFORMATION FOR SEQ ID NO:29:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "linker"

(xi) SEQUENCE DESCRIPTION: SEQ ID NO:29:

GCGAATTCGG 10

(2) INFORMATION FOR SEQ ID NO:30:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "linker"

(xi) SEQUENCE DESCRIPTION: SEQ ID NO:30:

CGGAATTCCG 10

(2) INFORMATION FOR SEQ ID NO:31:

(i) SEQUENCE CHARACTERISTICS:
(A) LENGTH: 12 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "linker"

(xi) SEQUENCE DESCRIPTION: SEQ ID NO:31:

CCCGAATTCG GG 12

(2) INFORMATION FOR SEQ ID NO:32:

(i) SEQUENCE CHARACTERISTICS:
(A) LENGTH: 12 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "linker"

(xi) SEQUENCE DESCRIPTION: SEQ ID NO:32:

CCGGAATTCC GG 12

(2) INFORMATION FOR SEQ ID NO:33:

(i) SEQUENCE CHARACTERISTICS:
(A) LENGTH: 12 amino acids

-continued (B) TYPE: amino acid
(C) STRANDEDNESS:
(D) TOPOLOGY: linear (ii) MOLECULE TYPE: peptide (xi) SEQUENCE DESCRIPTION: SEQ ID NO:33:

```
Ser Asp Ser Ser Phe Phe Ser Tyr Gly Glu Ile Pro
1               5                   10
```

(2) INFORMATION FOR SEQ ID NO:34:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic DNA"

(ix) FEATURE:
(A) NAME/KEY: CDS
(B) LOCATION: 1..42

(xi) SEQUENCE DESCRIPTION: SEQ ID NO:34:

```
ACT AGC GAC TCG AGC TTC TTT TCG TAC GGT GAG ATT CCT AGT                 42
Thr Ser Asp Ser Ser Phe Phe Ser Tyr Gly Glu Ile Pro Ser
  1               5                  10
```

(2) INFORMATION FOR SEQ ID NO:35:

(i) SEQUENCE CHARACTERISTICS:
(A) LENGTH: 14 amino acids
(B) TYPE: amino acid
(D) TOPOLOGY: linear (ii) MOLECULE TYPE: protein (xi) SEQUENCE DESCRIPTION: SEQ ID NO:35:

```
Thr Ser Asp Ser Ser Phe Phe Ser Tyr Gly Glu Ile Pro Ser
  1               5                  10
```

(2) INFORMATION FOR SEQ ID NO:36:

(i) SEQUENCE CHARACTERISTICS:
(A) LENGTH: 34 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:36:

```
Met Lys Lys Thr Leu Ile Ala Leu Ala Gly Ile Pro Glu Phe His His
1               5                   10                  15

Arg Lys Arg Lys Asn Tyr His Ile Pro Ala Leu Ala Val Ala Val Ser
            20                  25                  30

Ala Val
```

(2) INFORMATION FOR SEQ ID NO:37:

(i) SEQUENCE CHARACTERISTICS:
(A) LENGTH: 38 amino acids
(B) TYPE: amino acid
(C) STRANDEDNESS:
(D) TOPOLOGY: linear (ii) MOLECULE TYPE: peptide -continued (xi) SEQUENCE DESCRIPTION: SEQ ID NO:37:

```
Met Lys Lys Thr Leu Ile Ala Leu Ala Val Ala Val Ser Ala Val Glu
1               5                   10                  15

Phe Arg Asn Phe Thr Ile Gly His Glu Arg Thr Ile Thr Glu Phe Arg
            20                  25                  30

Ala Gly Ser Phe Asp Met
        35
```

(2) INFORMATION FOR SEQ ID NO:38:

(i) SEQUENCE CHARACTERISTICS:
(A) LENGTH: 41 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:38:

```
Met Lys Lys Thr Leu Ile Ala Leu Ala Val Ala Val Ser Ala Val Ser
1               5                   10                  15

Gly Ala Ala Ala His Ala Glu Phe Arg Asn Phe Thr Ile Gly His Glu
            20                  25                  30

Arg Thr Ile Thr Glu Phe Arg Ala Trp
        35                  40
```

(2) INFORMATION FOR SEQ ID NO:39:

(i) SEQUENCE CHARACTERISTICS:
(A) LENGTH: 35 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:39:

```
Met Lys Lys Thr Leu Ile Ala Leu Ala Val Ala Val Ser Ala Val Ser
1               5                   10                  15

Arg Asn Ser Gly Ile Ser Pro Glu Lys Lys Glu Leu Ser Ile Asn Ser
            20                  25                  30

Gly Ala Trp
        35
```

(2) INFORMATION FOR SEQ ID NO:40:

(i) SEQUENCE CHARACTERISTICS:
(A) LENGTH: 9 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:40:

```
Ser Ser Phe Phe Ser Tyr Gly Glu Ile
1               5
```

(2) INFORMATION FOR SEQ ID NO:41:

(i) SEQUENCE CHARACTERISTICS:
(A) LENGTH: 5 amino acids
(B) TYPE: amino acid
(C) STRANDEDNESS:

-continued (D) TOPOLOGY: linear (ii) MOLECULE TYPE: peptide (xi) SEQUENCE DESCRIPTION: SEQ ID NO:41:

Ala His Ala Trp Thr
1 5

(2) INFORMATION FOR SEQ ID NO:42:

(i) SEQUENCE CHARACTERISTICS:
(A) LENGTH: 5 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:42:

Ala His Ala Ala Asp
1 5

(2) INFORMATION FOR SEQ ID NO:43:

(i) SEQUENCE CHARACTERISTICS:
(A) LENGTH: 14 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:43:

Ala Asp Ser Ser Phe Phe Ser Tyr Gly Glu Ile Met His Ala
1 5 10

(2) INFORMATION FOR SEQ ID NO:44:

(i) SEQUENCE CHARACTERISTICS:
(A) LENGTH: 36 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "oligonucleotide"

(xi) SEQUENCE DESCRIPTION: SEQ ID NO:44:

TCGATGAAGA GATCTGGCTA TGGTCAGCCT ATTGCG 36

(2) INFORMATION FOR SEQ ID NO:45:

(i) SEQUENCE CHARACTERISTICS:
(A) LENGTH: 36 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "oligonucleotide"

(iv) ANTI-SENSE: YES (xi) SEQUENCE DESCRIPTION: SEQ ID NO:45:

TCGACGCAAT AGGCTGACCA TAGCCAGATC TCTTCA 36

(2) INFORMATION FOR SEQ ID NO:46:

(i) SEQUENCE CHARACTERISTICS:

-continued (A) LENGTH: 12 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:46:

```
Ser Met Lys Arg Ser Gly Tyr Gly Gln Pro Ile Ala
1               5                   10
```

(2) INFORMATION FOR SEQ ID NO:47:

(i) SEQUENCE CHARACTERISTICS:
(A) LENGTH: 30 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:47:

```
Ala His Ala Ala Asp Ser Met Lys Arg Ser Gly Tyr Gly Gln Pro Ile
1               5                   10                  15

Ala Ser Ser Phe Phe Ser Tyr Gly Glu Ile Met His Ala Trp
            20                  25                  30
```

(2) INFORMATION FOR SEQ ID NO:48:

(i) SEQUENCE CHARACTERISTICS:
(A) LENGTH: 36 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "oligonucleotide"

(xi) SEQUENCE DESCRIPTION: SEQ ID NO:48:

GAAAAGATCT GGTTATGGAC AGCCGATTGC AGTGCA 36

(2) INFORMATION FOR SEQ ID NO:49:

(i) SEQUENCE CHARACTERISTICS:
(A) LENGTH: 36 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "oligonucleotide"

(iv) ANTI-SENSE: YES (xi) SEQUENCE DESCRIPTION: SEQ ID NO:49:

CTGCAATCGG CTGTCCATAA CCAGATCTTT TCTGCA 36

(2) INFORMATION FOR SEQ ID NO:50:

(i) SEQUENCE CHARACTERISTICS:
(A) LENGTH: 12 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:50:

Lys Arg Ser Gly Tyr Gly Gln Pro Ile Ala Val His

-continued 1 5 10

(2) INFORMATION FOR SEQ ID NO:51:

(i) SEQUENCE CHARACTERISTICS:
(A) LENGTH: 30 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:51:

```
Ala His Ala Ala Asp Ser Ser Phe Phe Ser Tyr Gly Glu Ile Met Xaa
1               5                   10                  15

Lys Arg Ser Gly Tyr Gly Gln Pro Ile Ala Val His Ala Trp
            20                  25                  30
```

(2) INFORMATION FOR SEQ ID NO:52:

(i) SEQUENCE CHARACTERISTICS:
(A) LENGTH: 36 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "oligonucleotide"

(xi) SEQUENCE DESCRIPTION: SEQ ID NO:52:

CTAGCGACTC GAGCTTCTTT TCGTACGGTG ACATTC 36

(2) INFORMATION FOR SEQ ID NO:53:

(i) SEQUENCE CHARACTERISTICS:
(A) LENGTH: 36 base pairs
(B) TYPE: nucleic acid
(C) STRANDEDNESS: double
(D) TOPOLOGY: linear (ii) MOLECULE TYPE: other nucleic acid
(A) DESCRIPTION: /desc = "oligonucleotide"

(iv) ANTI-SENSE: YES (xi) SEQUENCE DESCRIPTION: SEQ ID NO:53:

CTAGGAATCT CACCGTACGA AAAGAAGCTC GAGTCG 36

(2) INFORMATION FOR SEQ ID NO:54:

(i) SEQUENCE CHARACTERISTICS:
(A) LENGTH: 30 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:54:

```
Asn Lys Thr Ser Asp Ser Ser Phe Phe Ser Tyr Gly Glu Ile Pro Ser
1               5                   10                  15

Met Lys Arg Ser Gly Tyr Gly Gln Pro Ile Ala Gly Asp Leu
            20                  25                  30
```

(2) INFORMATION FOR SEQ ID NO:55:

(i) SEQUENCE CHARACTERISTICS:
(A) LENGTH: 36 base pairs

-continued (B) TYPE: nucleic acid
(C) STRANDEDNESS: single
(D) TOPOLOGY: linear (ii) MOLECULE TYPE: other nucleic acid
(A) DESCRIPTION: /desc = "oligonucleotide"

(xi) SEQUENCE DESCRIPTION: SEQ ID NO:55:

TCGATGAAGA GATCTGGCTA TGGTCAGCCT ATTGCG 36

(2) INFORMATION FOR SEQ ID NO:56:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "oligonucleotide"

(iv) ANTI-SENSE: YES (xi) SEQUENCE DESCRIPTION: SEQ ID NO:56:

TGCACGCAAT AGGCTGACCA TAGCCAGATC TCTTCA 36

(2) INFORMATION FOR SEQ ID NO:57:

(i) SEQUENCE CHARACTERISTICS:
(A) LENGTH: 25 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:57:

```
Thr Ser Asp Ser Met Lys Arg Ser Gly Tyr Gly Gln Pro Ile Ala Ser
1               5                   10                  15

Phe Phe Ser Tyr Gly Glu Ile Pro Ser
            20                  25
```

(2) INFORMATION FOR SEQ ID NO:58:

(i) SEQUENCE CHARACTERISTICS:
(A) LENGTH: 12 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:58:

```
Asp Asn Pro Ala Ser Thr Thr Asn Lys Asp Lys Gly
1               5                   10
```

(2) INFORMATION FOR SEQ ID NO:59:

(i) SEQUENCE CHARACTERISTICS:
(A) LENGTH: 28 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:59:

```
Ala Ala Asp Ser Ser Phe Phe Ser Tyr Gly Glu Ile Met Gln Lys Arg
1               5                   10                  15
```

-continued

Ser Gly Tyr Gly Gln Pro Ile Ala Val His Ala Trp
20 25

(2) INFORMATION FOR SEQ ID NO:60:

(i) SEQUENCE CHARACTERISTICS:
(A) LENGTH: 15 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:60:

Thr Val Ser Asp Ser Ser Phe Phe Ser Tyr Gly Glu Ile Pro Phe
1 5 10 15

(2) INFORMATION FOR SEQ ID NO:61:

(i) SEQUENCE CHARACTERISTICS:
(A) LENGTH: 13 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:61:

Ser Met Lys Arg Ser Gly Tyr Gly Gln Pro Ile Ala Gly
1 5 10

(2) INFORMATION FOR SEQ ID NO:62:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:62:

AATTCCCCGG ATCCGTCGAC CTGCAG 26

(2) INFORMATION FOR SEQ ID NO:63:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:63:

CTGCAGGTCG ACGGATCCGG GG 22

(2) INFORMATION FOR SEQ ID NO:64:

(i) SEQUENCE CHARACTERISTICS:
(A) LENGTH: 51 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS -continued (B) LOCATION: 1..51

(xi) SEQUENCE DESCRIPTION: SEQ ID NO:64:

```
GGA ATT CCC CGG ATC CGT CGA CCT GCA GGT CGA CGG ATC CGG GGA ATT        48
Gly Ile Pro Arg Ile Arg Arg Pro Ala Gly Arg Arg Ile Arg Gly Ile
  1               5                  10                  15

CCN                                                                    51
Pro
```

(2) INFORMATION FOR SEQ ID NO:65:

(i) SEQUENCE CHARACTERISTICS:
(A) LENGTH: 17 amino acids
(B) TYPE: amino acid
(D) TOPOLOGY: linear (ii) MOLECULE TYPE: protein (xi) SEQUENCE DESCRIPTION: SEQ ID NO:65:

```
Gly Ile Pro Arg Ile Arg Arg Pro Ala Gly Arg Arg Ile Arg Gly Ile
  1               5                  10                  15

Pro
```

(2) INFORMATION FOR SEQ ID NO:66:

(i) SEQUENCE CHARACTERISTICS:
(A) LENGTH: 16 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:66:

```
Glu Phe Pro Gly Ser Val Asp Leu Gln Val Asp Gly Ser Gly Glu Phe
1               5                  10                  15
```

(2) INFORMATION FOR SEQ ID NO:67:

(i) SEQUENCE CHARACTERISTICS:
(A) LENGTH: 16 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:67:

```
Asn Ser Pro Asp Pro Ser Thr Cys Arg Ser Thr Asp Pro Gly Asn Ser
1               5                  10                  15
```

(2) INFORMATION FOR SEQ ID NO:68:

(i) SEQUENCE CHARACTERISTICS:
(A) LENGTH: 52 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1..51

(xi) SEQUENCE DESCRIPTION: SEQ ID NO:68:

```
CCG AAT TCC CCG GAT CCG TCG ACC TGC AGG TCG ACG GAT CCG GGG AAT        48
Pro Asn Ser Pro Asp Pro Ser Thr Cys Arg Ser Thr Asp Pro Gly Asn
```

-continued

```
  1               5                   10                  15

TCG G                                                                 52
Ser
```

(2) INFORMATION FOR SEQ ID NO:69:

(i) SEQUENCE CHARACTERISTICS:
(A) LENGTH: 17 amino acids
(B) TYPE: amino acid
(D) TOPOLOGY: linear (ii) MOLECULE TYPE: protein (xi) SEQUENCE DESCRIPTION: SEQ ID NO:69:

```
Pro Asn Ser Pro Asp Pro Ser Thr Cys Arg Ser Thr Asp Pro Gly Asn
  1               5                   10                  15

Ser
```

(2) INFORMATION FOR SEQ ID NO:70:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:70:

```
Arg Ile Pro Arg Ile Arg Arg Pro Ala Gly Arg Arg Ile Arg Gly Ile
1               5                   10                  15

Arg
```

(2) INFORMATION FOR SEQ ID NO:71:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:71:

```
Glu Phe Pro Gly Ser Val Asp Leu Gln Val Asp Gly Ser Gly Glu Phe
1               5                   10                  15

Gly
```

(2) INFORMATION FOR SEQ ID NO:72:

(i) SEQUENCE CHARACTERISTICS:
(A) LENGTH: 52 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1..51

(xi) SEQUENCE DESCRIPTION: SEQ ID NO:72:

```
CGG AAT TCC CCG GAT CCG TCG ACC TGC AGG TCG ACG GAT CCG GGG AAT       48
Arg Asn Ser Pro Asp Pro Ser Thr Cys Arg Ser Thr Asp Pro Gly Asn
  1               5                   10                  15
```

-continued

```
TCC G                                                                  52
Ser


(2) INFORMATION FOR SEQ ID NO:73:

     (i) SEQUENCE CHARACTERISTICS:
          (A) LENGTH: 17 amino acids
          (B) TYPE: amino acid
          (D) TOPOLOGY: linear

    (ii) MOLECULE TYPE: protein

    (xi) SEQUENCE DESCRIPTION: SEQ ID NO:73:

Arg Asn Ser Pro Asp Pro Ser Thr Cys Arg Ser Thr Asp Pro Gly Asn
  1               5                  10                  15

Ser


(2) INFORMATION FOR SEQ ID NO:74:

     (i) SEQUENCE CHARACTERISTICS:
          (A) LENGTH: 17 amino acids
          (B) TYPE: amino acid
          (C) STRANDEDNESS:
          (D) TOPOLOGY: linear

    (ii) MOLECULE TYPE: peptide

    (xi) SEQUENCE DESCRIPTION: SEQ ID NO:74:

Gly Ile Pro Arg Ile Arg Arg Pro Ala Gly Arg Arg Ile Arg Gly Ile
1               5                   10                  15

Pro


(2) INFORMATION FOR SEQ ID NO:75:

     (i) SEQUENCE CHARACTERISTICS:
          (A) LENGTH: 17 amino acids
          (B) TYPE: amino acid
          (C) STRANDEDNESS:
          (D) TOPOLOGY: linear

    (ii) MOLECULE TYPE: peptide

    (xi) SEQUENCE DESCRIPTION: SEQ ID NO:75:

Glu Phe Pro Gly Ser Val Asp Leu Gln Val Asp Gly Ser Gly Glu Phe
1               5                   10                  15

Arg


(2) INFORMATION FOR SEQ ID NO:76:

     (i) SEQUENCE CHARACTERISTICS:
          (A) LENGTH: 54 base pairs
          (B) TYPE: nucleic acid
          (C) STRANDEDNESS: single
          (D) TOPOLOGY: linear

    (ii) MOLECULE TYPE: cDNA

    (ix) FEATURE:
          (A) NAME/KEY: CDS
          (B) LOCATION: 1..54

    (xi) SEQUENCE DESCRIPTION: SEQ ID NO:76:

CCC GAA TTC CCC GGA TCC GTC GAC CTG CAG GTC GAC GGA TCC GGG GAA        48
Pro Glu Phe Pro Gly Ser Val Asp Leu Gln Val Asp Gly Ser Gly Glu
  1               5                  10                  15

TTC GGG                                                                54
Phe Gly
```

-continued (2) INFORMATION FOR SEQ ID NO:77:

(i) SEQUENCE CHARACTERISTICS:
(A) LENGTH: 18 amino acids
(B) TYPE: amino acid
(D) TOPOLOGY: linear (ii) MOLECULE TYPE: protein (xi) SEQUENCE DESCRIPTION: SEQ ID NO:77:

```
Pro Glu Phe Pro Gly Ser Val Asp Leu Gln Val Asp Gly Ser Gly Glu
  1               5                  10                  15

Phe Gly
```

(2) INFORMATION FOR SEQ ID NO:78:

(i) SEQUENCE CHARACTERISTICS:
(A) LENGTH: 18 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:78:

```
Pro Asn Ser Pro Asp Pro Ser Thr Cys Arg Ser Thr Asp Pro Gly Asn
1               5                   10                  15

Ser Gly
```

(2) INFORMATION FOR SEQ ID NO:79:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:79:

```
Arg Ile Pro Arg Ile Arg Arg Pro Ala Gly Arg Arg Ile Arg Gly Ile
1               5                   10                  15

Arg
```

(2) INFORMATION FOR SEQ ID NO:80:

(i) SEQUENCE CHARACTERISTICS:
(A) LENGTH: 54 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1..54

(xi) SEQUENCE DESCRIPTION: SEQ ID NO:80:

```
CCG GAA TTC CCC GGA TCC GTC GAC CTG CAG GTC GAC GGA TCC GGG GAA       48
Pro Glu Phe Pro Gly Ser Val Asp Leu Gln Val Asp Gly Ser Gly Glu
  1               5                  10                  15

TTC CGG                                                               54
Phe Arg
```

-continued (2) INFORMATION FOR SEQ ID NO:81:

(i) SEQUENCE CHARACTERISTICS:
(A) LENGTH: 18 amino acids
(B) TYPE: amino acid
(D) TOPOLOGY: linear (ii) MOLECULE TYPE: protein (xi) SEQUENCE DESCRIPTION: SEQ ID NO:81:

```
Pro Glu Phe Pro Gly Ser Val Asp Leu Gln Val Asp Gly Ser Gly Glu
  1               5                  10                  15

Phe Arg
```

(2) INFORMATION FOR SEQ ID NO:82:

(i) SEQUENCE CHARACTERISTICS:
(A) LENGTH: 18 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:82:

```
Arg Asn Ser Pro Asp Pro Ser Thr Cys Arg Ser Thr Asp Pro Gly Asn
1               5                   10                  15

Ser Gly
```

(2) INFORMATION FOR SEQ ID NO:83:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:83:

```
Gly Ile Pro Arg Ile Arg Arg Pro Ala Gly Arg Arg Ile Arg Gly Ile
1               5                   10                  15

Pro
```

(2) INFORMATION FOR SEQ ID NO:84:

(i) SEQUENCE CHARACTERISTICS:
(A) LENGTH: 63 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 1..63

(xi) SEQUENCE DESCRIPTION: SEQ ID NO:84:

```
AAC GTA ACT AGT GCT AGC TCT TTC TTC TCT TAC GGT GAA ATC CCC CTA        48
Asn Val Thr Ser Ala Ser Ser Phe Phe Ser Tyr Gly Glu Ile Pro Leu
  1               5                  10                  15

GGT ACT TCT AGA AGT                                                    63
Gly Thr Ser Arg Ser
             20
```

(2) INFORMATION FOR SEQ ID NO:85:

-continued (i) SEQUENCE CHARACTERISTICS:
(A) LENGTH: 21 amino acids
(B) TYPE: amino acid
(D) TOPOLOGY: linear (ii) MOLECULE TYPE: protein (xi) SEQUENCE DESCRIPTION: SEQ ID NO:85:

```
Asn Val Thr Ser Ala Ser Ser Phe Phe Ser Tyr Gly Glu Ile Pro Leu
  1               5                  10                  15

Gly Thr Ser Arg Ser
             20
```

(2) INFORMATION FOR SEQ ID NO:86:

(i) SEQUENCE CHARACTERISTICS:
(A) LENGTH: 35 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 3..35

(xi) SEQUENCE DESCRIPTION: SEQ ID NO:86:

```
CT AGT AGT TCA TTC TTT AGT TAT GGT GAA ATT GGA                       35
   Ser Ser Ser Phe Phe Ser Tyr Gly Glu Ile Gly
     1               5                  10
```

(2) INFORMATION FOR SEQ ID NO:87:

(i) SEQUENCE CHARACTERISTICS:
(A) LENGTH: 11 amino acids
(B) TYPE: amino acid
(D) TOPOLOGY: linear (ii) MOLECULE TYPE: protein (xi) SEQUENCE DESCRIPTION: SEQ ID NO:87:

```
Ser Ser Ser Phe Phe Ser Tyr Gly Glu Ile Gly
  1               5                  10
```

(2) INFORMATION FOR SEQ ID NO:88:

(i) SEQUENCE CHARACTERISTICS:
(A) LENGTH: 35 base pairs
(B) TYPE: nucleic acid
(C) STRANDEDNESS: double
(D) TOPOLOGY: linear (ii) MOLECULE TYPE: DNA (genomic)

(iv) ANTI-SENSE: YES (xi) SEQUENCE DESCRIPTION: SEQ ID NO:88:

```
GATCTCCAAT TTCACCATAA CTAAAGAATG AACTA                               35
```

(2) INFORMATION FOR SEQ ID NO:89:

(i) SEQUENCE CHARACTERISTICS:
(A) LENGTH: 35 base pairs
(B) TYPE: nucleic acid
(C) STRANDEDNESS: double
(D) TOPOLOGY: linear (ii) MOLECULE TYPE: cDNA -continued (ix) FEATURE:
(A) NAME/KEY: CDS
(B) LOCATION: 3..35

(xi) SEQUENCE DESCRIPTION: SEQ ID NO:89:

```
CT AGT AGT TCA TTC TTT AGT TAT GGT GAA ATT CCA                       35
   Ser Ser Ser Phe Phe Ser Tyr Gly Glu Ile Pro
     1               5                  10
```

(2) INFORMATION FOR SEQ ID NO:90:

(i) SEQUENCE CHARACTERISTICS:
(A) LENGTH: 11 amino acids
(B) TYPE: amino acid
(D) TOPOLOGY: linear (ii) MOLECULE TYPE: protein (xi) SEQUENCE DESCRIPTION: SEQ ID NO:90:

```
Ser Ser Ser Phe Phe Ser Tyr Gly Glu Ile Pro
  1               5                  10
```

(2) INFORMATION FOR SEQ ID NO:91:

(i) SEQUENCE CHARACTERISTICS:
(A) LENGTH: 35 base pairs
(B) TYPE: nucleic acid
(C) STRANDEDNESS: double
(D) TOPOLOGY: linear (ii) MOLECULE TYPE: DNA (genomic)

(iv) ANTI-SENSE: YES (xi) SEQUENCE DESCRIPTION: SEQ ID NO:91:

```
GATCTGGAAT TTCACCATAA CTAAAGAATG AACTA                               35
```

(2) INFORMATION FOR SEQ ID NO:92:

(i) SEQUENCE CHARACTERISTICS:
(A) LENGTH: 34 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 1..33

(xi) SEQUENCE DESCRIPTION: SEQ ID NO:92:

```
AAC AGT TCA TTC TTT AGT TAT GGT GAA ATT CCT A                        34
Asn Ser Ser Phe Phe Ser Tyr Gly Glu Ile Pro
  1               5                  10
```

(2) INFORMATION FOR SEQ ID NO:93:

(i) SEQUENCE CHARACTERISTICS:
(A) LENGTH: 11 amino acids
(B) TYPE: amino acid
(D) TOPOLOGY: linear (ii) MOLECULE TYPE: protein (xi) SEQUENCE DESCRIPTION: SEQ ID NO:93:

```
Asn Ser Ser Phe Phe Ser Tyr Gly Glu Ile Pro
  1               5                  10
```

-continued (2) INFORMATION FOR SEQ ID NO:94:

(i) SEQUENCE CHARACTERISTICS:
(A) LENGTH: 38 base pairs
(B) TYPE: nucleic acid
(C) STRANDEDNESS: double
(D) TOPOLOGY: linear (ii) MOLECULE TYPE: DNA (genomic)

(iv) ANTI-SENSE: YES (xi) SEQUENCE DESCRIPTION: SEQ ID NO:94:

```
CTAGTAGGAA TTTCACCATA ACTAAAGAAT GAACTGTT                       38
```

(2) INFORMATION FOR SEQ ID NO:95:

(i) SEQUENCE CHARACTERISTICS:
(A) LENGTH: 41 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 3..41

(xi) SEQUENCE DESCRIPTION: SEQ ID NO:95:

```
CT AGT ATG AAA CGG AGT GGT TAT GGT CAG CCT ATT GCA GGA                 41
   Ser Met Lys Arg Ser Gly Tyr Gly Gln Pro Ile Ala Gly
     1               5                  10
```

(2) INFORMATION FOR SEQ ID NO:96:

(i) SEQUENCE CHARACTERISTICS:
(A) LENGTH: 13 amino acids
(B) TYPE: amino acid
(D) TOPOLOGY: linear (ii) MOLECULE TYPE: protein (xi) SEQUENCE DESCRIPTION: SEQ ID NO:96:

```
Ser Met Lys Arg Ser Gly Tyr Gly Gln Pro Ile Ala Gly
  1               5                  10
```

(2) INFORMATION FOR SEQ ID NO:97:

(i) SEQUENCE CHARACTERISTICS:
(A) LENGTH: 41 base pairs
(B) TYPE: nucleic acid
(C) STRANDEDNESS: double
(D) TOPOLOGY: linear (ii) MOLECULE TYPE: DNA (genomic)

(iv) ANTI-SENSE: YES (xi) SEQUENCE DESCRIPTION: SEQ ID NO:97:

```
GATGTCCTGC AATAGGCTGA CCATAACCAC TCCGTTTCAT A                   41
```

(2) INFORMATION FOR SEQ ID NO:98:

(i) SEQUENCE CHARACTERISTICS:
(A) LENGTH: 41 base pairs
(B) TYPE: nucleic acid
(C) STRANDEDNESS: double
(D) TOPOLOGY: linear -continued (ii) MOLECULE TYPE: cDNA (ix) FEATURE:
(A) NAME/KEY: CDS
(B) LOCATION: 3..41

(xi) SEQUENCE DESCRIPTION: SEQ ID NO:98:

```
CT AGT GAT AAC CCT GCT AGC ACT ACA AAT AAA GAT AAA GGA                 41
   Ser Asp Asn Pro Ala Ser Thr Thr Asn Lys Asp Lys Gly
     1               5                  10
```

(2) INFORMATION FOR SEQ ID NO:99:

(i) SEQUENCE CHARACTERISTICS:
(A) LENGTH: 13 amino acids
(B) TYPE: amino acid
(D) TOPOLOGY: linear (ii) MOLECULE TYPE: protein (xi) SEQUENCE DESCRIPTION: SEQ ID NO:99:

```
Ser Asp Asn Pro Ala Ser Thr Thr Asn Lys Asp Lys Gly
  1               5                  10
```

(2) INFORMATION FOR SEQ ID NO:100:

(i) SEQUENCE CHARACTERISTICS:
(A) LENGTH: 41 base pairs
(B) TYPE: nucleic acid
(C) STRANDEDNESS: double
(D) TOPOLOGY: linear (ii) MOLECULE TYPE: DNA (genomic)

(iv) ANTI-SENSE: YES (xi) SEQUENCE DESCRIPTION: SEQ ID NO:100:

```
GATCTCCTTT ATCTTTATTT GTAGTGCTAG CAGGGTTATC A                          41
```

(2) INFORMATION FOR SEQ ID NO:101:

(i) SEQUENCE CHARACTERISTICS:
(A) LENGTH: 47 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 2..46

(xi) SEQUENCE DESCRIPTION: SEQ ID NO:101:

```
G GCA GTT AAC CCT GCA AGT ACT ACA AAT AAA GAT AAA ACT AGT GCG          46
  Ala Val Asn Pro Ala Ser Thr Thr Asn Lys Asp Lys Thr Ser Ala
    1               5                  10                  15

G                                                                      47
```

(2) INFORMATION FOR SEQ ID NO:102:

(i) SEQUENCE CHARACTERISTICS:
(A) LENGTH: 15 amino acids
(B) TYPE: amino acid
(D) TOPOLOGY: linear (ii) MOLECULE TYPE: protein (xi) SEQUENCE DESCRIPTION: SEQ ID NO:102:

-continued

```
Ala Val Asn Pro Ala Ser Thr Thr Asn Lys Asp Lys Thr Ser Ala
  1               5                  10                  15
```

(2) INFORMATION FOR SEQ ID NO:103:

(i) SEQUENCE CHARACTERISTICS:
(A) LENGTH: 37 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 1..36

(xi) SEQUENCE DESCRIPTION: SEQ ID NO:103:

```
AAC TAT AAA CAG AAA ATT ATT GCA CCT GCA CAG AAA A                        37
Asn Tyr Lys Gln Lys Ile Ile Ala Pro Ala Gln Lys
  1               5                  10
```

(2) INFORMATION FOR SEQ ID NO:104:

(i) SEQUENCE CHARACTERISTICS:
(A) LENGTH: 12 amino acids
(B) TYPE: amino acid
(D) TOPOLOGY: linear (ii) MOLECULE TYPE: protein (xi) SEQUENCE DESCRIPTION: SEQ ID NO:104:

```
Asn Tyr Lys Gln Lys Ile Ile Ala Pro Ala Gln Lys
  1               5                  10
```

(2) INFORMATION FOR SEQ ID NO:105:

(i) SEQUENCE CHARACTERISTICS:
(A) LENGTH: 41 base pairs
(B) TYPE: nucleic acid
(C) STRANDEDNESS: double
(D) TOPOLOGY: linear (ii) MOLECULE TYPE: DNA (genomic)

(iv) ANTI-SENSE: YES (xi) SEQUENCE DESCRIPTION: SEQ ID NO:105:

```
CTAGTTTTCT GTGCAGGTGC AATAATTTTC TGTTTATAGT T                            41
```

(2) INFORMATION FOR SEQ ID NO:106:

(i) SEQUENCE CHARACTERISTICS:
(A) LENGTH: 41 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 3..41

(xi) SEQUENCE DESCRIPTION: SEQ ID NO:106:

```
CT AGT ATT AGA AAT TGG AAC TTT GAT TTT GGT CTG TTA GGA                   41
   Ser Ile Arg Asn Trp Asn Phe Asp Phe Gly Leu Leu Gly
     1               5                  10
```

(2) INFORMATION FOR SEQ ID NO:107:

-continued (i) SEQUENCE CHARACTERISTICS:
(A) LENGTH: 13 amino acids
(B) TYPE: amino acid
(D) TOPOLOGY: linear (ii) MOLECULE TYPE: protein (xi) SEQUENCE DESCRIPTION: SEQ ID NO:107:

```
Ser Ile Arg Asn Trp Asn Phe Asp Phe Gly Leu Leu Gly
  1               5                  10
```

(2) INFORMATION FOR SEQ ID NO:108:

(i) SEQUENCE CHARACTERISTICS:
(A) LENGTH: 44 base pairs
(B) TYPE: nucleic acid
(C) STRANDEDNESS: double
(D) TOPOLOGY: linear (ii) MOLECULE TYPE: DNA (genomic)

(iv) ANTI-SENSE: YES (xi) SEQUENCE DESCRIPTION: SEQ ID NO:108:

```
GATCTCCTAA CAGACCAAAA TCAAAGTTCC AATTTCTAAT ACTA                      44
```

(2) INFORMATION FOR SEQ ID NO:109:

(i) SEQUENCE CHARACTERISTICS:
(A) LENGTH: 42 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 1..42

(xi) SEQUENCE DESCRIPTION: SEQ ID NO:109:

```
GAA TTC AGT GAT AGT TCT TTC TTT TCC TAT GGT GAA ATT CCG                 42
Glu Phe Ser Asp Ser Ser Phe Phe Ser Tyr Gly Glu Ile Pro
  1               5                  10
```

(2) INFORMATION FOR SEQ ID NO:110:

(i) SEQUENCE CHARACTERISTICS:
(A) LENGTH: 14 amino acids
(B) TYPE: amino acid
(D) TOPOLOGY: linear (ii) MOLECULE TYPE: protein (xi) SEQUENCE DESCRIPTION: SEQ ID NO:110:

```
Glu Phe Ser Asp Ser Ser Phe Phe Ser Tyr Gly Glu Ile Pro
  1               5                  10
```

(2) INFORMATION FOR SEQ ID NO:111:

(i) SEQUENCE CHARACTERISTICS:
(A) LENGTH: 42 base pairs
(B) TYPE: nucleic acid
(C) STRANDEDNESS: double
(D) TOPOLOGY: linear (ii) MOLECULE TYPE: DNA (genomic)

(iv) ANTI-SENSE: YES

-continued (xi) SEQUENCE DESCRIPTION: SEQ ID NO:111:

```
AATTCCGGAA TTTCACCATA GGAAAAGAAA GAACTATCAC TG                          42
```

(2) INFORMATION FOR SEQ ID NO:112:

(i) SEQUENCE CHARACTERISTICS:
(A) LENGTH: 66 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 1..66

(xi) SEQUENCE DESCRIPTION: SEQ ID NO:112:

```
GCG CAT GCG GAA TTC AGT GAT AGT TCT TTC TTT TCC TAT GGT GAA ATT       48
Ala His Ala Glu Phe Ser Asp Ser Ser Phe Phe Ser Tyr Gly Glu Ile
  1               5                  10                  15

CCG GAA TTC CGT GCG TGG                                               66
Pro Glu Phe Arg Ala Trp
             20
```

(2) INFORMATION FOR SEQ ID NO:113:

(i) SEQUENCE CHARACTERISTICS:
(A) LENGTH: 22 amino acids
(B) TYPE: amino acid
(D) TOPOLOGY: linear (ii) MOLECULE TYPE: protein (xi) SEQUENCE DESCRIPTION: SEQ ID NO:113:

```
Ala His Ala Glu Phe Ser Asp Ser Ser Phe Phe Ser Tyr Gly Glu Ile
  1               5                  10                  15

Pro Glu Phe Arg Ala Trp
             20
```

(2) INFORMATION FOR SEQ ID NO:114:

(i) SEQUENCE CHARACTERISTICS:
(A) LENGTH: 54 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 1..54

(xi) SEQUENCE DESCRIPTION: SEQ ID NO:114:

```
GCG CAT GCT GCA GAC TCG AGC TTT TTC AGT TAC GGT GAA ATT ATG CAT       48
Ala His Ala Ala Asp Ser Ser Phe Phe Ser Tyr Gly Glu Ile Met His
  1               5                  10                  15

GCG TGG                                                               54
Ala Trp
```

(2) INFORMATION FOR SEQ ID NO:115:

(i) SEQUENCE CHARACTERISTICS:
(A) LENGTH: 18 amino acids
(B) TYPE: amino acid
(D) TOPOLOGY: linear -continued

```
    (ii) MOLECULE TYPE: protein

    (xi) SEQUENCE DESCRIPTION: SEQ ID NO:115:

Ala His Ala Ala Asp Ser Ser Phe Phe Ser Tyr Gly Glu Ile Met His
  1               5                  10                  15

Ala Trp
```

CLPG SUBUNIT OF CS31A PROTEIN CAPSULE CONTAINING HETEROLOGOUS PEPTIDES

This application claims priority to application 92/15464 filed on Dec. 22, 1992 and PCT/FR93/01281 filed Dec. 21, 1993.

FIELD OF THE INVENTION

The present invention relates to the sub-unit of the CS31A protein capsule, referred to as the "ClpG protein", whose amino-acid sequence is modified by at least one heterologous peptide.

The invention also relates to the CS31A protein capsule that includes such a sub-unit, as well as the microorganisms that carry a CS31A protein capsule for which amino-acid sequence in the sub-unit is modified by at least one heterologous peptide.

The invention also relates to the procedures for obtaining such sub-units, to the CS31A capsules that contain them, and to microorganisms that carry these CS31A protein capsules, as well as to the use of these capsules in the preparation of vaccines, the production of peptides, and the preparation of immunological tests.

BACKGROUND OF THE INVENTION

The outer membrane of microorganisms includes various protein structures, such as flagella, pili, fimbriae, or protein capsules, which in particular endow the said microorganisms with properties of motion or attachment.

These structures include highly antigenic molecules that have made it possible to prepare, starting with the protein structure isolated from these microorganisms or from the microorganisms themselves, vaccines that correspond to the various types of antigens isolated in the microorganisms. Thus, the French patent application published under No. 2 466 251 proposes an anti-colibacillus animal vaccine that contains at least one antigen obtained from various strains of *Escherichia coli.*

Furthermore, these molecules constitute a comparable number of carrier proteins into which foreign epitopes can be introduced that endow the said proteins with a new antigenic nature, whose immunogenicity allows the said proteins to be used as vaccines. Thus, the European patent application published under No. 264 150 describes microorganisms whose outer membrane carries pili whose composition has been modified by a change in the protein sequence of the sub-unit.

Membrane structures such as pili, fimbriae, or protein capsules appear to be more advantageous in the field of vaccination than outer-membrane proteins. In fact, for pili, all of the structural protein is located outside the cell; certain polypeptide regions are present only at the cell surface; and accessibility to these proteins risks being impeded by the lipopolysaccharide and the capsular envelopes. Furthermore, the sub-units of the fimbriae or of the protein capsules are present at the bacterial surface in much greater numbers than the outer-membrane proteins.

Furthermore, the purification of a membrane protein is more difficult than the purification of proteins that are entirely outside the microorganisms, such as pili or fimbriae.

The nature of the microorganisms involved in the invention depends solely on their ability to produce the CS31A protein capsule. Specifically, it involves bacteria in the family of Enterobacteriaceae that belong to the *Escherichia coli* and *Klebsiella pneumoniae* species.

Many studies have been made of the pili of *E. coli*, and, more specifically, the K88 and K99 fimbrial sub-units have been amply described.

More recent studies have revealed, in a wild strain of *E. coli* designated as "31A+" in the French patent application published under No. 2 466 251, a protein structure designated as "CS31A". The operon that governs the biogenesis of this structure has been cloned in a host organism, and the gene that codes for the CS31A sub-unit, referred to as "Clpg", has been located, characterized, and sequenced. (See C. Martin, C. Boeuf, and F. Bousquet, in *Microbial Pathogenesis*, Vol. 10 (1991), pp. 429–442; J. P. Girardeau, Y. Bertin, C. Martin, M. DerVartanian, and C. Boeuf, in *Journal of Bacteriology*, Vol. 173, No. 23 (December 1991), pp. 7673–7983; and M. J. Korth, R. A. Schneider, and S. L. Moseley, in *Infection and Immunity*, Vol. 59, No. 7 (July 1991), pp. 2333–2340).

The CS31A structure is a protein capsule that is less organized and more flexible than the flagella and fimbriae, which are more organized and rigid. Consequently, it appears that the size of the peptides that can being expressed in the fimbriae and flagella could only with difficulty exceed approximately fifteen amino acids, whereas use of the CS31A protein capsules makes it possible to introduce larger foreign sequences, containing up to about a hundred amino acids.

Nevertheless, the introduction of heterologous peptide sequences is possible in the protein only at certain permissive sites, whose size and position must be determined.

SUMMARY OF THE INVENTION

The goal of the present invention is specifically to determine the regions of the ClpG protein into which heterologous proteins can be introduced without disturbing the biogenesis of the CS31A protein capsule.

The techniques used in the cloning and sequencing of the gene that codes for the CS31A sub-unit, and to identify the regions of the said sub-unit that accept heterologous insertions and/or substitutions, will be described in the detailed description of the invention. In the following paragraphs, reference will be made more specifically to FIG. 9, which represents the nucleotide sequence of the gene that codes for the CS31A sub-unit and the polypeptide sequence deduced from this nucleotide sequence.

Identification of the potentially permissive regions consists first of all of determining the variable regions within a family of proteins related to CS31A, i.e., the K88 and F41 proteins, and then of determining the continuous epitopes of, on the one hand, the denatured sub-units and, on the other hand, the native protein, and then determining the accessibility of these continuous epitopes.

The continuous epitopes often correspond to the variable regions of these proteins. Moreover, because the regions in question are immunodominant regions of the protein, these zones appear to be particularly indicated for presentation to the immune system of the vaccinating epitopes introduced into recombinant proteins.

Immunostructural research has made it possible to determine, in variable regions, the exact location of the continuous epitopes, which are usually flexible, hydrophilic, and accessible to the antibodies in the native protein. Thus, provided they are permissive, the immunoreactive variable regions defined by the amino acids located at positions 10 to 19, positions 38 to 58, positions 88 to 106, positions 144 to 172, positions 184 to 220, and positions 223 to 245 in FIG. 9 are selected for modification by heterologous peptides.

In addition to the comparison of the CS31A, K88, and F41 sequences, and the immunostructural study of CS31A, a random insertional mutagenesis technique has rounded out the study of the zones of the CS31A protein that are capable of accepting additions or substitutions of heterologous peptides.

The implementation of these techniques has made it possible to identify, in a presumptive way, four regions that are likely to accept modifications by heterologous peptides without affecting the biogenesis of the CS31A, i.e.:

Region A, which covers the signal peptide and the N-terminal end of the mature protein defined by the amino acids located at positions −13 and +8 in FIG. 9;

Region B, defined by the amino acids located at positions 10 and 58 in FIG. 9;

Region C, defined by the amino acids located at positions 123 and 164 in FIG. 9;

Region D, defined by the amino acids located at positions 183 and 257 in FIG. 9.

Consequently, the invention relates to a sub-unit of a CS31A protein capsule whose amino-acid sequence is modified at least at one of the regions A, B, C, or D described above, by at least one heterologous peptide.

Region A accepts the introduction of from 4 to 20 heterologous amino acids by random insertional mutagenesis. More specifically, the invention relates to a sub-unit of the CS31A capsule whose amino-acid sequence is modified by at least one heterologous peptide, between the amino acids located at positions −1 and +1 in FIG. 9.

Region B contains a variable sequence, referred to as "V1", defined by the amino acids located at positions 10 and 58 in FIG. 9. Insertions of from 4 to 18 amino acids have been obtained by random insertional mutagenesis in Region B. Furthermore, Region B also includes two particularly immunogenic and antigenic peptides in the denatured form of the protein, with these peptides being delimited respectively by the amino acids located at positions 10 and 19 and positions 38 and 58 in FIG. 9. Thus, the invention relates more specifically to a sub-unit of the CS31A capsule whose amino-acid sequence is modified by the introduction of at least one heterologous peptide in relation to at least one of these two peptides.

Region C contains a variable sequence, referred to as "V2", defined by the amino acids located at positions 123 and 150 in FIG. 9. Insertions consisting of from 4 to 18 amino acids have been obtained by random insertional mutagenesis in Region C. Furthermore, Region C also includes, in its C-terminal portion, a continuous epitope defined by the amino acids located at positions 151 and 160 in FIG. 9. Thus, the invention relates more specifically to a sub-unit of the CS31A capsule whose amino-acid sequence is modified by the introduction of at least one heterologous peptide in relation to this epitope.

Region D contains a variable sequence, referred to as "V3", defined by the amino acids located at positions 183 and 221 in FIG. 9. This region contains the only continuous antigenic and immunogenic epitope in the native protein, as defined by the amino acids located at positions 188 and 196 in FIG. 9. Furthermore, the C-terminal portion of Region D includes three other immunogenic and antigenic peptides in the denatured form of the protein, with these peptides being defined respectively by the amino acids located at positions 211 and 219, positions 223 and 231, and positions 235 and 246 in FIG. 9. Thus, the invention relates more specifically to a sub-unit of the CS31A capsule whose amino-acid sequence is modified by the introduction of at least one heterologous peptide in relation to at least one of these four peptides.

Various epitopes, particularly vaccinating epitopes, obtained from bacteria, parasites, or viruses can also be introduced into the ClpG protein.

Therefore, the invention relates to the sub-unit of a CS31A protein capsule whose amino-acid sequence is modified by at least one heterologous peptide selected from among the C epitope or the A epitope of the transmissible pork gastroenteritis virus; an epitope of the VP6 protein of the bovine rotavirus; the C3 epitope of the polio virus; or an epitope of the VP1 protein of the aphthous fever virus.

One example that can be cited consists of the introduction of the C epitope or the A epitope of the transmissible pork gastroenteritis virus into at least one of the permissive regions of the ClpG protein that constitutes the CS31A sub-unit. The sub-unit, the protein capsule, or even the microorganism thus modified presents the C epitope and/or the A epitope, and is particularly useful in the preparation of a vaccine against the transmissible gastroenteritis virus in pigs.

Another example that can be cited consists of the introduction of an epitope of the VP6 protein of bovine rotavirus into at least one of the permissions regions of the ClpG\ protein that constitutes the CS31A sub-unit, followed by the use of either the sub-unit, the protein capsule, or a genetically modified microorganism in order to express in the CS31A protein capsule the epitope of the VP6 protein of bovine rotavirus, in the preparation of a vaccine against the diarrhea caused by the rotavirus in cattle.

The modifications of the protein sequence of the sub-unit are advantageously implemented by means of genetic engineering techniques, which consisting of modifying the wild DNA sequence that codes for the sub-unit in order to obtain a modified amino-acid sequence.

In addition to the modifications that consist of the substitution and/or removal and/or addition of one or more bases in, from, or to the coding DNA sequence, and that have no effect on the biogenesis of the sub-unit, the term "modification" refers most specifically to the introduction, into the wild DNA, of a fragment of foreign DNA whose sequence and reading phase in the recombinant gene determine the heterologous polypeptide sequence introduced into the amino-acid sequence of the sub-unit. It may then involve the replacement of a fragment of the wild DNA by a fragment of foreign DNA or the addition of a fragment of foreign DNA.

Thus, the invention also relates to procedures that make it possible to obtain a sub-unit of a CS31A capsule whose amino-acid sequence is modified by at least one heterologous peptide, consisting of the introduction, into at least one of the permissive regions A, B, C, or D of the wild gene that codes for the sub-unit, of at least one fragment of DNA that codes for a heterologous peptide. The heterologous sequences are introduced in any of the following ways:

By cloning after directed mutagenesis leading to the creation of restriction sites that allow insertions or substitutions;

By cloning in restriction sites such as EcoRI, introduced by random insertional mutagenesis;

By direct insertion through direct cloning of the heterologous sequence between the signal peptide and the mature peptide of the ClpG pre-protein.

The fragment of foreign DNA may be either natural or synthetic. It is selected or prepared in accordance with the peptide intended to be expressed in the CS31A sub-unit, which itself is determined in accordance with the intended application.

The invention also relates to CS31A protein capsules that include a ClpG sub-unit that has been modified in accordance with the invention, along with microorganisms whose outer membrane carries such capsules. The latter can be obtained, for example, through the culture of an *E. coli* bacterium that expresses the genes that govern the biogenesis of the CS31A capsule, modified by at least one fragment of DNA that codes for a heterologous peptide. This culture is advantageously prepared either on a gelose culture medium that allows the collection of the bacteria at the surface of the gelose, or in a fluid medium in a fermenter that allows the bacteria to be collected after centrifuging. A fraction enriched in modified CS31A capsules can be obtained from these microorganisms through the vigorous stirring of the bacterial suspensions resulting from the collection at the surface of the gelose or from the culture in the fermenter. After centrifuging at 5000 g, a supernatant is obtained that is rich in modified CS31A capsules. This supernatant can advantageously be purified starting with a fraction that is precipitated on 20 percent ammonium sulfate by means of a chromatography stage with hydrophobic interaction on phenyl Sepharose. Elution with water makes it possible to obtain a product that has a high molecular weight and that is more than 90 percent pure. Starting from this fraction, the modified CS31A sub-units can easily be purified by molecular filtration on a column of Sephacryl S-300 in the presence of 6M guanidium chloride.

The CS31A sub-unit is highly antigenic and immunogenic. The introduction of a heterologous peptide into this sub-unit, in the regions defined above, makes it possible to confer a new antigenic characteristic on the sub-unit and also on the microorganisms whose CS31A capsules carry such a sub-unit.

The CS31A protein capsule also constitutes a system that is particularly well adapted to the production of peptides that are intended particularly for use in the preparation of immunological tests. The hybrid proteins obtained through the introduction, into the gene that codes for the ClpG protein, of a DNA that codes for a predetermined heterologous peptide can advantageously be used either as an antigen for the detection of antibodies or as an immunogen for the reduction of antibodies against proteins, such as for example against pathogens that cannot be cultured.

Thus, the invention relates to the use of the CS31A sub-unit whose amino-acid sequence is modified by at least one heterologous peptide, with the C8 protein capsule that includes such a sub-unit, or alternatively the microorganisms whose outer membrane carries such CS31A protein capsules, as an active ingredient in the manufacture of immunogenic compounds.

These immunogenic compounds can advantageously be implemented in the preparation of human or animal vaccines, or in the preparation of immunological tests that can be used in human or animal health care.

Other characteristics of the invention will become clear from the following description, which refers to the cloning and sequencing of the gene that codes for the CS31A sub-unit, to the identification of the regions of the ClpG sub-unit that can accept heterologous peptides, to the introduction of such peptides into the determined regions, and, finally, to the immunogenicity of the heterologous peptides in the recombinant ClpG proteins produced by the bacteria.

BRIEF DESCRIPTION OF THE DRAWINGS

FIG. 9 shows the complete sequence of the ClpG gene (SEQ ID NO:1 and SEQ ID NO:2).

FIG. 16 shows the immunoreactive regions (SEQ ID NO:2) recognized by the antiserums, as produced in four rabbits.

FIG. 17 shows the immunoreactive regions (SEQ ID NO:2) recognized by the anti-CS31A antiserums produced in rabbits N1 and N2.

FIG. 19 shows locations of five peptides in the primary sequence (SEQ ID NO:2).

FIG. 20 shows ELISA competition for measuring the accessibility of the peptide in native CS31A.

FIG. 25 shows the nucleotide sequences (SEQ ID NO:64 to SEQ ID NO:83, in consecutive order) resulting from insertion of EcoRI linkers and EcoRI-PstI-EcoRI polylinkers into the ClpG gene.

FIG. 27 shows the oligonucleotide synthesis sequences utilized that code for TGE (SEQ ID NOs:85, 84, 87, 86, 88, 90, 89, 91, 93, 92, 94, 96, 95 and 97, in that order), rotavirus (SEQ ID NOs: 107, 106 and 108 in that order), polio (SEQ ID NOs: 99, 98, 100, 102 and 101 in that order), and FMDV (SEQ ID NOs: 104, 103 and 105 in that order) epitopes.

FIG. 28 shows changes made in the V2 region (SEQ ID NO:1 and SEQ ID NO:2).

FIG. 34 shows the synthesis (+) or non-synthesis (−) of protein, and production (+) or non-production (−) of CS31A capsule.

DETAILED DESCRIPTION OF THE INVENTION

A) MATERIALS AND METHODS

1) *E. coli* and Plasmid Strains

Figure 2:
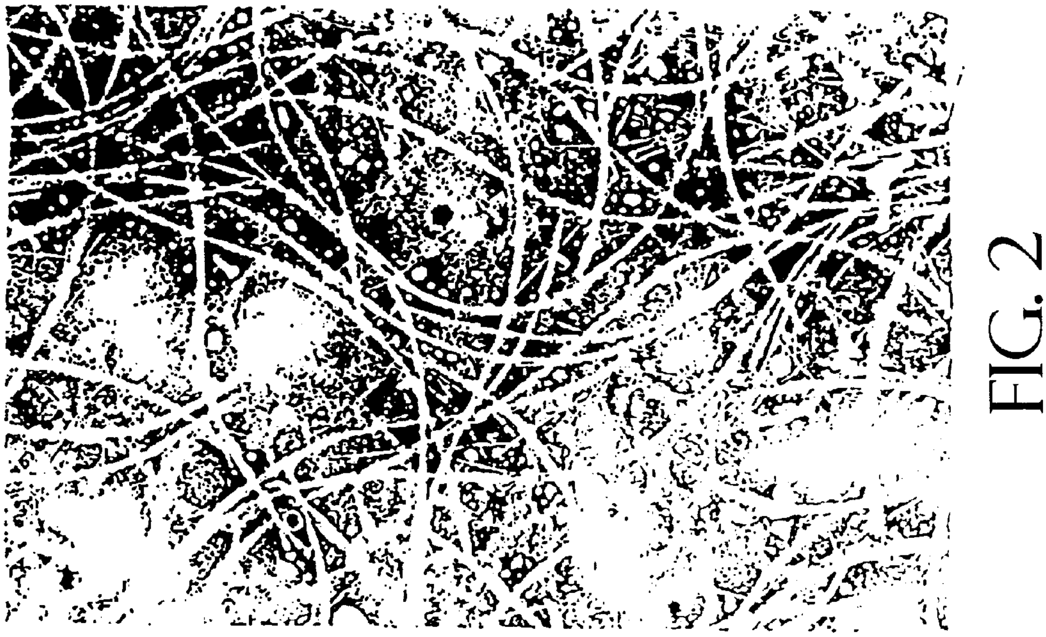
FIG. 2 shows flagella (fl) and 20K fimbriae (fim).

DB 6433: Δ(lacZYA), pro, met, Su III, λs, Nal r, Rif r. (See R. W. Davis, D. Botstein, and J. R. Roth, in *Advanced Bacterial Genetics* (New York, Cold Spring Harbor Laboratory, 1980).)

31A: The hosting wild strain of p31A, as deposited in the collection of the Pasteur Institute (25 Rue du Docteur Roux, Paris 15) at No. I-105.

Orne 6: The wild strain of the 017:K7:H18 serotype that produces CS31A, as used to purify the CS31A. This *E. coli* strain does not carry other surface proteins that can interfere with or complicate the purification of the CS31A.

The bacterial strains used to transfer the recombinant plasmids by transformation are:

DH5 α: F-φ80 dlac ZΔM15, end A1, rec A1, hsdR17 ($r^-k$, $m^+k$) sup E44, thi-1, gyr A, rel A1, Δ(lacZYA -arg F), U169, λ−(Bethesda Research Laboratories, Life Technologies, Inc.).

JM 109: F'traD36, lac Iq, Δ(lacZ)ΔM15, proAB, recA1, end A1, gyr A96, thi, hsd R17, supE 44E14−m, rel A1, Δ(lac-proAB). (See C. Yanisk-Perron, J. Viera, and J. Messing, in *Gene*, Vol. 33 (1985), pp. 103–119.)

The pDSPH524, pPSX83, and pDEV41155 plasmids used and constructed during this work are described in Section E below with regard to intergenic complementation.

The cultures were produced in a solid or fluid Luria-Bertani (LB) medium to which the appropriate antibiotics had been added, at concentrations of 100 μg/ml or 50 μg/ml for ampicillin, 25 μg/ml for chloramphenicol, and 10 μg/ml for tetracycline.

The production of beta-galactosidase was determined by the blue staining of the colonies on an LB medium containing 2 mM of isopropyl-beta-D-thio-galactoside (IPTG) and 40 μg/ml of 5-bromo-4-chloro-3-indolyl-beta-D-galactopyranoside (X-gal).

The restriction enzymes were used in accordance with the manufacturers' recommendations.

The conditions for digestion by Dnase I consisted of 1 ng/μg of circular DNA for 15 to 20 minutes at a temperature of 25° C. in a Dnase buffer (200 mM TRIS-HCl at a pH of 7.5; 15 mM of MnCl2; and 1 mg of BSA per ml).

T4-DNA polymerase was used at a ratio of 3.3 U/μg of DNA at a temperature of 22° C. for 30 minutes, and the Klenow fragment of the DNA polymerase of *E. coli* was used at a ratio of 2.5 U/μg of DNA at a temperature of 22° C. for 30 minutes in the presence of 1 mM of dNTP. The polymerase buffer consisted of 200 mM of TRIS-HCl at a pH of 7.5; 10 mM of MgCl2; and 1 mM of DTT.

T4-DNA ligase was used at a ratio of 0.2 U/μg of DNA at a temperature of 10° C. overnight for the ligation of the cohesive ends; at a ratio of 1 U/μg of DNA at a temperature of 4° C. overnight for the ligation of the free ends; and at a ratio of 10 U/μg of DNA at a temperature of 4° C. overnight for the ligation of the non-phosphorylated linkers. The buffer used for the ligation of these linkers consisted of 660 mM of TRIS-HCl at a pH of 7.5; 50 mM of MgCl2; 50 mM of DTT, 1 mg/ml of BSA; 10 mM of hexamine cobalt (III) chloride, 2 mM of ATP; and 5 mM of spermidine.

2) Preparation of the Linkers (Annealing)

In order for the ligation to take place, the linkers must be pre-hybridized. The concentration of non-phosphorylated EcoRI linkers is 1 μg/μl in TE (10 mM TRIS-HCl at a pH of 8.0, and 1 mM EDTA). The solution containing the oligonucleotides is incubated for one minute at a temperature of 80° C., then transferred into a 500 ml beaker containing water at 65° C. The beaker is then placed in ice. When the temperature reaches 4° C. the pre-hybridized linkers can be frozen to −20° C. before use.

3) Preparation of the DNA

The plasmids are extracted either by means of the alkaline lysate method or by means of the so-called "boiling" method for mini-preparations of DNA (see Maniatis et al., *Molecular Cloning: A Laboratory Manual,* Cold Spring Harbor Laboratory (1982)). Preparation of the plasmids with the aid of Quiagen extraction kits has also been implemented for purification of the DNA.

4) Transformation

The CaCl2 method is employed to transform *E. coli* DH5 α and *E. coli* JM 109 (see Maniatis et al. (1982)). From 1 to 10 μl of the ligation mixture are used to transform the strain. The transforming agents are selected on agar LB that contains the appropriate antibiotics.

5) Electrophoresis

For analysis of the DNA, electrophoresis operations on agarose gels are carried out on horizontally oriented equipment in a TRIS-borate buffer (TRIS 90 mM, boric acid 90 mM, and EDTA 2 mM, at a pH of 8.0) in the presence of ethidium bromide. The reference standard for size is either the 1 Kb DNA ladder (from Gibco-BRL), or the VIII DNA ladder (from Boehringer), or the 100 base-pair DNA ladder (from Pharmacia).

For analysis of the proteins, SDS-PAGE gels are implemented on vertically oriented equipment at a concentration of 10 to 15 percent polyacrylamide, in accordance with the conventional technique described by Laemmli in *Nature*, Vol. 227 (1970), pp. 680–685.

6) Sequencing

The sequencing is accomplished on double- or single-strand DNA, in accordance with the method described by Sanger et al. in *Proc. Natl. Acad. Sci. USA*, Vol. 74 (1977), pp. 5463–5467, with the modified -T7 polymerase sequenase, dATP ($\alpha^{-35}$ S), and a sequencing kit (from U.S. Biochemical Corp., or else the multi-well Amersham kit).

7) Genetic Constructions

The conventional genetic engineering techniques used for the various genetic constructions are the ones described by Maniatis et al. (1982) or by Sambrook et al. (1989).

8) Directed Mutagenesis

The method employed is the partially single-strand DNA (i.e., the gap-duplex-DNA) method. It uses the pMa5-8 and pMc5-8 vectors, and has been described by Stanssens et al., in NAR, Vol. 17 (1989), pp. 4441–4454.

9) Preparation of the CS31A Protein

The CS31A protein is purified in accordance with two methods, one of which allows a native purified form to be obtained, and the other of which allows a denatured purified form to be obtained.

Table 1 below indicates the purification procedures for the native and denatured forms of the CS31A protein.

a) Purification in Native (i.e., Polymer) Form

The purification of the native antigen with a high molecular weight is achieved in accordance with a simple method, described below, whose various stages make it possible to eliminate almost all contaminants, and particularly the ones associated with membranal debris (i.e., proteins and LPS). Table 1 above and Table 2 below make it possible to follow the stages in the purification process. (For the quantification of the KDO, see *Methods in Microbiology*, Vol. 6B, pp. 209–344.)

The bacteria collected in PBS starting from a culture of 10 vials of Rous in a gelose Minca medium, as decribed by Guinee (in *Infection and Immunity*, Vol. 13 (1976), pp. 1369–1377), are homogenized at maximum speed for 3×1 minute at room temperature, and then centrifuged for 15 minutes at 25,000 g. The supernatant fluid is then centrifuged at a temperature of 10° C. for 30 minutes at 55,000 g. The resulting supernatant is subjected to sequential precipitation on ammonium sulfate. The concentrated residue obtained, with 10 to 20% saturation, is returned to solution in PBS at a pH of 7.2 at a temperature of 4° C. overnight. Then 2M NaCl is added, and the solution is left at equilibrium for one hour at room temperature and then purified by means of hydrophobic-interaction chromatography (HIC) on phenyl Sepharose CL4B (from Pharmacia). A 5 percent solution of sodium taurodeoxycholate (DOC) is added to the native protein eluted by the water, and the resulting mixture is subjected to ultracentrifuging for 200 minutes at 110,000 g. The concentrated residue (i.e., UC in TDC), which consists essentially of the CS31A protein in its native form with a high molecular weight is made up with 10 mM TRIS buffer (at a pH of 7.8) and left in solution at a temperature of 4° C. (overnight, with no stirring).

Table 2 below indicates the control measurements for the purification of the CS31A through measurement of the residual KDO.

TABLE 1

```
                         Suspension in PBS
                                |
                      AMS precipitation 10 to 20%
                                |
     Addition of         ← HIC φ sepharose →      Lyophilization
  taurodeoxycholate       elution peak (water)          |
    from Na to 0.5%                              made up with TRTS 5 mM
          |                                         8.5 M Gnd HCl
Stirring for 2 hours at 20° C.                          |
          |                                      2 hours at 37° C.
   Ultracentrifuging                                    |
at 110,000 g for 200 minutes                     Addition of TRIS 5 mM
          |                                        final 6 M Gnd HCl
   Room temperature                                     |
          |                                   Sephacryl S-300, 6 M Gnd HCl
    Native CS31A                                        |
  concentrated residue                               peak 2
                                                        |
                                             Dialysis and lyophilization
                                                        |
                                                 Denatured C531A
```

TABLE 2

| | Native CS31A Orne 6 (UC in TDC) Proteins | | | |
|---|---|---|---|---|
| | Totals (in mg) | Percentage of total proteins | Percentage of bacteria (dry weight) | Total KDO (in $\mu$g) |
| Supernatant: 12,000 g | 54.60 | 100 | 4.23 | 0.110 |
| Supernatant: 50,000 g | 52.00 | 95 | 4.03 | 0.110 |
| Supernatant: 20% x | 29.45 | 54 | 2.22 | 0.065 |
| Concentrated residue: 20% | 5.40 | 9.9 | 0.42 | 0.009 |
| Eluted HIC: 2 M NaCl | 0.35 | 0.7 | 0.03 | 0 |
| Eluted HIC: water | 1.806 | 3.3 | 0.14 | 0 |
| UC in TDC: 110,000 g 200 nm [SIC] | 1.033 | 1.9 | 0.08 | 0 |

b) Purification in Denatured Form (i.e., the Sub-unit)

As indicated in Table 1 above, the antigen with a high molecular weight (i.e., the HIC lyophilisate) is dissociated into sub-units (30 kDa) through treatment with 8.5 M guanidium [hydro]chloride (Gnd HCl) for 2 hours at a temperature of 37° C. The concentration is brought to 6M Gnd HCl by the addition of TRIS (at a pH of 7.8), and the protein is purified by chromatography on a permeation gel on Sephacryl S-300 (from Pharmacia) in a dissociating buffer (TRIS at a pH of 7.8, and 6MGnd HCl). The product corresponding to the elution of a protein with 30 kiloDaltons of ammonium (5 mM at a pH of 7.8) [is] lyophilized and stored at a temperature of −80° C.

10) Preparation of the Specific Antibodies

The antibodies (either against the native protein or against the denatured protein) were prepared in rabbits by means of 4 intradermal injections of 250 $\mu$g of purified proteins at 15-day intervals in the presence of incomplete Freund's adjuvant. The IgGs were purified by means of affinity chromatography on Protein A Sepharose (from Pharmacia) and marked with biotin in accordance with the procedure described by Hantowich et al. in the *Journal of Nuclear Medicine,* Vol. 28 (1987), pp.1294–1302.

The antipeptides were obtained by means of three intradermal injections of synthetic peptides coupled with ovalbumin by means of glutaraldehyde or by means of Bisaminobenzidine on a tyrosine remainder (i.e., the presence of an NH2 in the peptide), in accordance with the procedures described by Van Regenmortel et al. in *Laboratory Techniques in Biochemistry and Molecular Biology:* "Synthetic polypeptides as antigens" (1988).

In order to prevent non-specific reactions, the antibodies used are absorbed against the different bacterial strains, either with whole cells or with ketone extracts obtained from ultrasonic cell preparations.

11) Immunological Techniques

The presence of the CS31A antigen on bacteria absorbed on a nitrocellulose filter is revealed by an immunological method through the use of specific polyclonal antibodies directed either against the protein prepared in either native or denatured form, or else against peptides coupled with ovalbumin. The fixation of unmarked antibodies is detected by anti-rabbit goat IgGs marked with peroxidase (from Nordic), and the fixation of biotinylated IgGs is detected by streptavidine coupled with peroxidase (from Pierce), with 4-chloronaphthol as a substrate. The proteins are separated by SDS-PAGE and transferred to the nitrocellulose membrane, which is then subjected to an immunological detection test with the various specific antibodies described above, in accordance with the so-called "Western blot" technique.

The antigens and the antibodies are quantified in accordance with an ELISA [i.e., Enzyme-Linked ImmunoSorbent Assay] method, through the capture of the antibodies (either directly or in accordance with the so-called "sandwich" method) for the quantification of the antibodies, and competitively for the quantification of the antigen. The specificity and titer of the antipeptides are measured by means of a method that involves the capture of the antibodies by the peptides fixed on Immulon II plates (from Dynatech).

The definition of the continuous epitopes is achieved through the measurement of the immunoreactivity of 257 peptides of 9 remainders that overlap with a prepared remainder, covering the entirety of the primary sequence of the protein.

The epitope scanning described by Geysen et al. in *Proc. Natl. Acad. Sci.,* Vol. 81 (1984), p. 3998, is accomplished through the use of a kit (from Cambridge Research Biochemicals, Northwich, U.K.) that provides a software program that allows the peptide synthesis to be driven and the results to be processed; the activated synthesis heads or starters; and the 20 derivatives of the amino acids necessary for the synthesis of the peptides. Detection of the antibodies fixed on the peptides is ensured by means of an ELISA procedure, and the reading of the plates (Dynatec MR-5000) and the definition of the epitopes are driven by the software provided by the supplier. The epitopes have been defined with the antibodies directed against the native protein or against the denatured protein.

The antigenicity of the epitopes defined in this way was measured:

Either by comparing the profile of the epitope scan obtained before and after competition with the antigen in its native form; or By measuring the reduction in the titer of antipeptides subjected to competition with the native protein; or By measuring the capture of the antibodies by the native protein (in accordance with the ELISA sandwich method or by means of a Dot-Blot on nitrocellulose).

12) Electron Microscope Observations

All of the observations were made with an EM-400 electron microscope (from Philips Electronic Instrument[s], Inc., of Mahwah, N.J.), with an acceleration current of 80 kV.

The bacteria and the purified extracts were observed (on a 300-meson grid covered with collodion) after negative staining with 1 percent phosphotungstic acid.

The whole bacterial cells were observed after marking with colloidal gold after the anti-CS31A antibodies obtained had been caused to act against the native protein, in accordance with the technique described by Levine et al. in *Infection and Immunity,* Vol. 44 (1984), pp. 409–420. The ferritin marking of the bacterial cutting was accomplished in accordance with the method described by Orskov et al. in *Infection and Immunity,* Vol. 47 (1985), pp. 191–200. The primary antibodies were diluted to one-eighth, and the anti-rabbit IgG goat serum marked with colloidal gold (from Jans[s]en Pharmaceutical, Piscataway, N.J.), and the anti-rabbit IgG goat serum marked with ferritin (from Miles-Yeda, Ltd., of Rehovot, Israel) were used in a ratio of 1/50.

B) MORPHOLOGICAL STUDY OF THE CS31A ANTIGEN UNDER ELECTRON MICROSCOPY

I. Observations after Negative Staining (with Phosphortungstic Acid)

1) On Whole Cells

Figure 1:
FIG. 1 is a photograph that represents a 110,000× negative stain of the wild reference strain of *E. coli* 31A.

FIG. 1 is a photograph that represents a 110,000× negative stain of the wild reference strain of *E. coli* 31A. At its surface this bacterium expresses flagella (fl), rigid fimbriae designated as "20K" (fim), and the CS31A antigen (clp).

The 20K fimbriae have a rigid filamentous structure 5 nm in diameter, and can reach a length of 1 μm. The CS31A antigen does not display this filamentous appearance, but instead forms a granulous capsular structure that envelops the entire surface of the bacterial cell.

2) On Whole Extracts

The pericellular structures were separated from the bacterial cells by means of a Vortex [device].

After negative staining (110,000×), the photograph in FIG. 2 clearly shows the flagella (fl) and the 20K fimbriae (fim). The CS31A (clp) antigen has the appearance of a granulous mass that adheres to the other structures. The estimated size of each granule is 50×100 angstroms. These granules may represent the constituent sub-unit of the CS31A antigen.

3) On Purified Extracts

Figure 3:
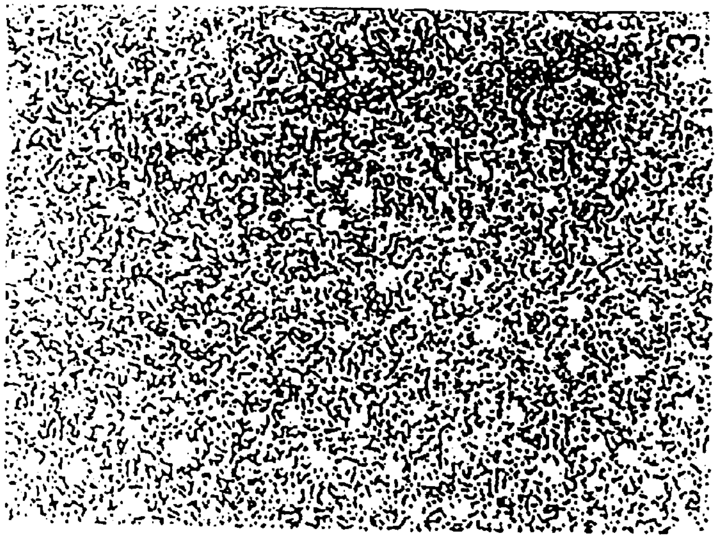
FIG. 3 shows purified CS31A antigen with high molecular weight after negative staining.

The photograph in FIG. 3 shows the purified CS31A antigen with a high molecular weight, after negative staining.

Figure 4:
FIG. 4 shows purified K88 antigen extract displaying a fibrillary appearance.

The purified fraction has a granular appearance similar to the one already observed for the other preparations. No fibrillary structure can be distinguished, and the "grains" appear disordered. In comparison, the purified K88 antigen extract clearly displays a fibrillary appearance (as indicated by the photograph in FIG. 4).

II. Observations after Marking by Specific Antibodies

1) Revelation with Colloidal Gold (10 nm) on Whole Cells

After having been deposited on the grids, the CS31A antigen was marked by a specific antibody (i.e., a rabbit antibody), and then revealed by an anti-rabbit [antibody] conjugated with the colloidal gold.

Figure 5:
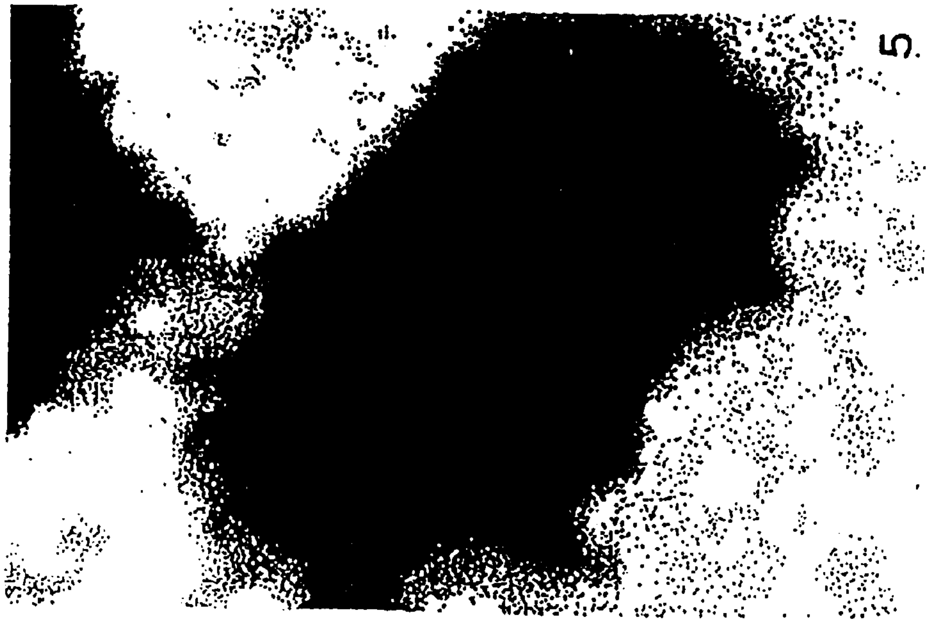
FIG. 5 shows grains of gold distributed uniformly around a bacterial cell.

In the photograph in FIG. 5, it can be seen that the grains of gold are distributed uniformly around the bacterial cell, and that there is no marking of the fibers, as is generally observed with fimbriae. The CS31A antigen appears to detach itself easily from the cell.

2) Revelation with Ferritin on a Section 50 nm Thick

The bacteria are marked by specific anti-CS31A antibodies obtained by immunizing rabbits and by anti-rabbit IgG antigens obtained from goats and conjugated with the ferritin. The cells are then embedded in a synthetic resin and then sectioned.

Figure 6:
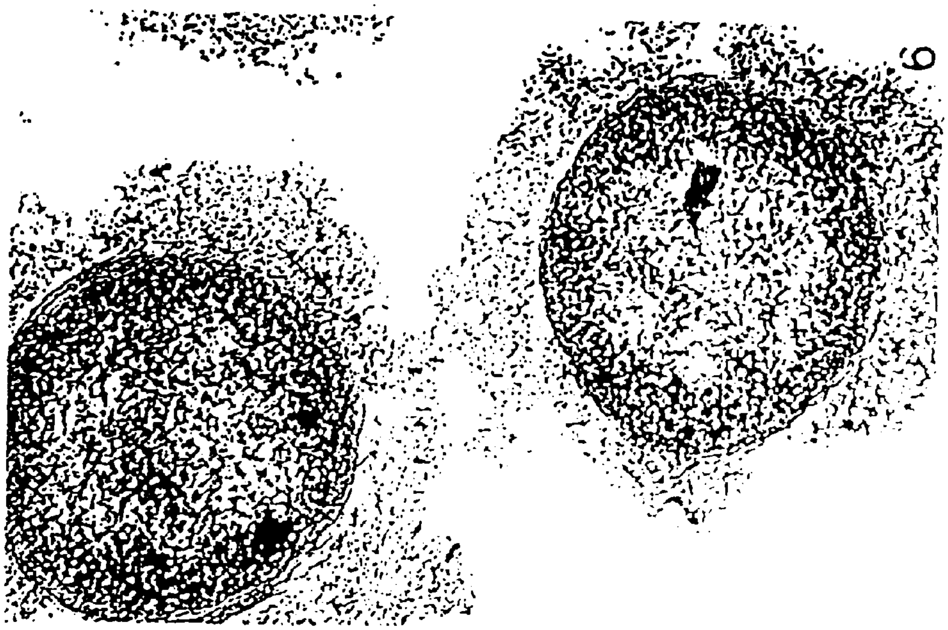
FIG. 6 shows grains fo ferritin aranged around a capsular structure that envelops a bacterial cell.

The photograph in FIG. 6 shows that the grains of ferritin are arranged all around a capsular structure that entirely envelops the bacterial cell. No fibrillary structure was marked by the ferritin.

III. Conclusions of the Structural Study of CS31A

In a fimbria, the polymerized (piliate) sub-units take on a more or less "taut" spiral structure. In the so-called "rigid" fimbriae (with a diameter of 5 to 7 nm) the sub-units are wound along the length of a spiral skeleton, with the sub-unit of one spiral forming interactions with the sub-units of other spirals. In the so-called "fimbrillae" or flexible fimbriae (with a diameter of 2 nm), the sub-units are also wound around a spiral skeleton, but the sub-units of a spiral no longer have direct interactions with the sub-units of the other spirals. On the other hand, the so-called "relaxed" spirals can form spindles consisting of associations of hundreds of individual fibers. The K88 and F41 antigens take on this type of structure, as shown in the photograph in FIG. 4.

In the case of CS31A, the protein sub-units are polymerized but do not appear to be wound around a spiral skeleton, and do not form fimbrillae. The sub-units are associated in a granulous mass that can resemble a capsule. This type of organization of the so-called "capsule-like antigen" was described in 1985 by Orskov et al. in "An adhesive capsule of *Escherichia coli,*" in *Infect. Immun.,* Vol. 47 (1985), pp. 191–200.

Previously published results (in *Infect. Immun.,* Vol. 56, pp. 2180–2188) indicate the presence of this type of capsular structure. However, because the term "capsule-like" was not adopted, the term "fimbriae", which appeared to be appropriate, was selected. Nevertheless, subsequent work performed on purified extracts confirmed the non-fibrillary nature of the CS31A antigen, as shown in the photograph in FIG. 3.

C) Cloning Of The Genes Necessary For The Biogenesis Of Cs31a

The genes necessary for the biogenesis of CS31A are carried by a conjugative plasmid, p31A, contained in the wild reference strain of *E. coli* 31A.

This 180 kb plasmid was transferred into the K12 DB 6433 *E. coli* strain, purified, and then partially restricted by means of the Sau3AI endonuclease.

The restrictive fragments consisting of from 9.5 to 11.5 kb were cloned in the pSUP202 vector (as described by R. Simon et al., 1983), restricted by BamHI, and treated with alkaline phosphatase. A total of 285 recombinant [plasmids] that were resistant to chloramphenicol and sensitive to tetracycline ($Cm^r$, $Tc^s$) were tested for the presence of CS31A, through the use of a polyclonal anti-CS31A antibody. Of these recombinant [plasmids], a total of 14 yielded a positive reaction. They contained a plasmid that included a restriction fragment with from 9 to 11 kb, depending on the case, oriented in either one direction or the other.

Therefore, the expression of the cloned genes does not appear to depend on an external promoter. A HindIII-EcoRI fragment consisting of 8.5 kb, which was common to all of the clones, was cloned, on the one hand, in the pBR322 vector plasmid cut by HindIII+EcoRI, thereby leading to the acquisition of the pAG315 plasmid (as described by C. Martin et al. in 1991), and, on the other hand, in the pHSG575 vector plasmid with a small number of copies, leading to the acquisition of the pEH524 plasmid (as described by C. Martin et al., in 1991).

Figure 7:
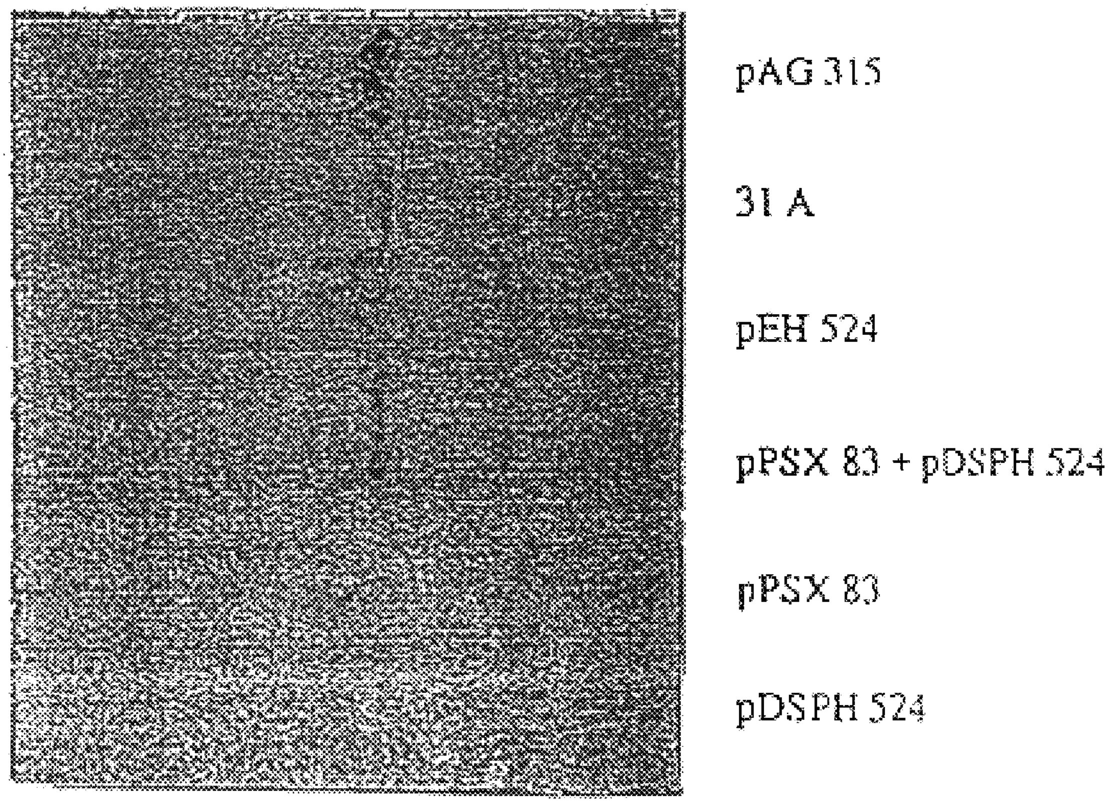
FIG. 7 shows the Western-blot analysis of extracts of bacteria that contain various recombinant plasmids.

FIG. 7 represents the Western-blot analysis of the extracts of bacteria that contain the various recombinant plasmids, and also of an anti-CS31A polyclonal antiserum. The extracts consist of the supernatant portion of a bacterial suspension that was heated for 20 minutes at 60° C.

The CS31A sub-units produced by a K12 strain of *E. coli* that contain pAG315 or pEH524 have the same apparent molecular weight as the sub-units produced by the 31A strain, and are recognized by the anti-C antibodies.

Figure 8:
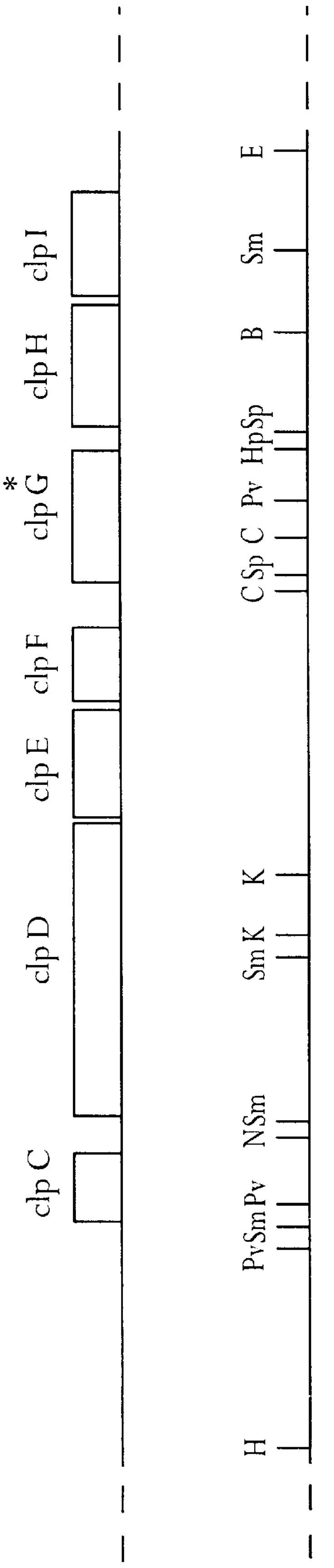
FIG. 8 shows a summary restriction map of pEH524.

FIG. 8 represents a summary restriction map for pEH524, and also the genetic map of the CS31A determinants. The latter map was created on the basis of results obtained by insertional mutagenesis of the Mini-Mu phages in pAG315 and a study of the proteins synthesized by the mutant plasmids in mini-cells, and also through the determination of the nucleotide sequence of certain genes (i.e., clpE, clpF, clpG, clpH, and clpI). The structure of the clpG gene is indicated by an asterisk. The letters represent restriction enzymes, as indicated in the following list:

| | | |
|---|---|---|
| B | = | BstXI |
| C | = | ClaI |
| E | = | EcoRI |
| H | = | HindIII |
| Hp | = | HpaI |
| K | = | KpnI |
| N | = | NruI |
| P | = | PvuII |
| S | = | SmaI |
| Sc | = | SacI |
| Sp | = | SphI |

D) Sequencing

The gene that codes for the CS31A sub-unit was sequenced on both strands in accordance with the Sanger method.

FIG. 9 shows the complete sequence of the clpG gene, with the presence of a single open reading frame consisting of 834 base pairs starting at the ATG initiation codon located 60 base pairs upstream of the first SphI site and ending with three stop codons located at positions 1218, 1227, and 1245. This reading frame codes for a protein with 278 remainders corresponding to a molecular weight of 28,780 daltons. The CS31A sub-unit is synthesized in the form of a precursor that carries a signal sequence of 21 amino acids that are cleaved before the tryptophan remainder at the time of export into the periplasm. Therefore, the mature sub-unit consists of 257 remainders, yielding a polypeptide with an inferred molecular weight of 26,777 daltons.

An AAGGAA sequence located 10 base pairs upstream of the ATG may constitute a ribosome (RBS) fixation sequence. The location of the 5' end of the messenger RNA reveals the existence of two transcription starting sites, separated by 76 base pairs, and suggests that the gene is transcribed from a pair of promoters, designated as P1 and P2 in FIG. 9.

E) Intergenic Complementation

Intergenic complementation makes it possible to manipulate, in vitro, the clpG gene of the constituent sub-unit of CS31A without affecting the rest of the CS31A operon, and to verify, in vivo, the expression of the modified clpG proteins. It facilitates the introduction of new single restriction sites in the clpg gene, through either directed mutagenesis or random mutagenesis. To implement intergenic complementation, the clpG gene and the associated genes that are necessary for the biogenesis of the CS31A were sub-cloned separately in two compatible vector plasmids.

I. Construction of the Plasmid that Carries the Associated Genes

Figure 10:
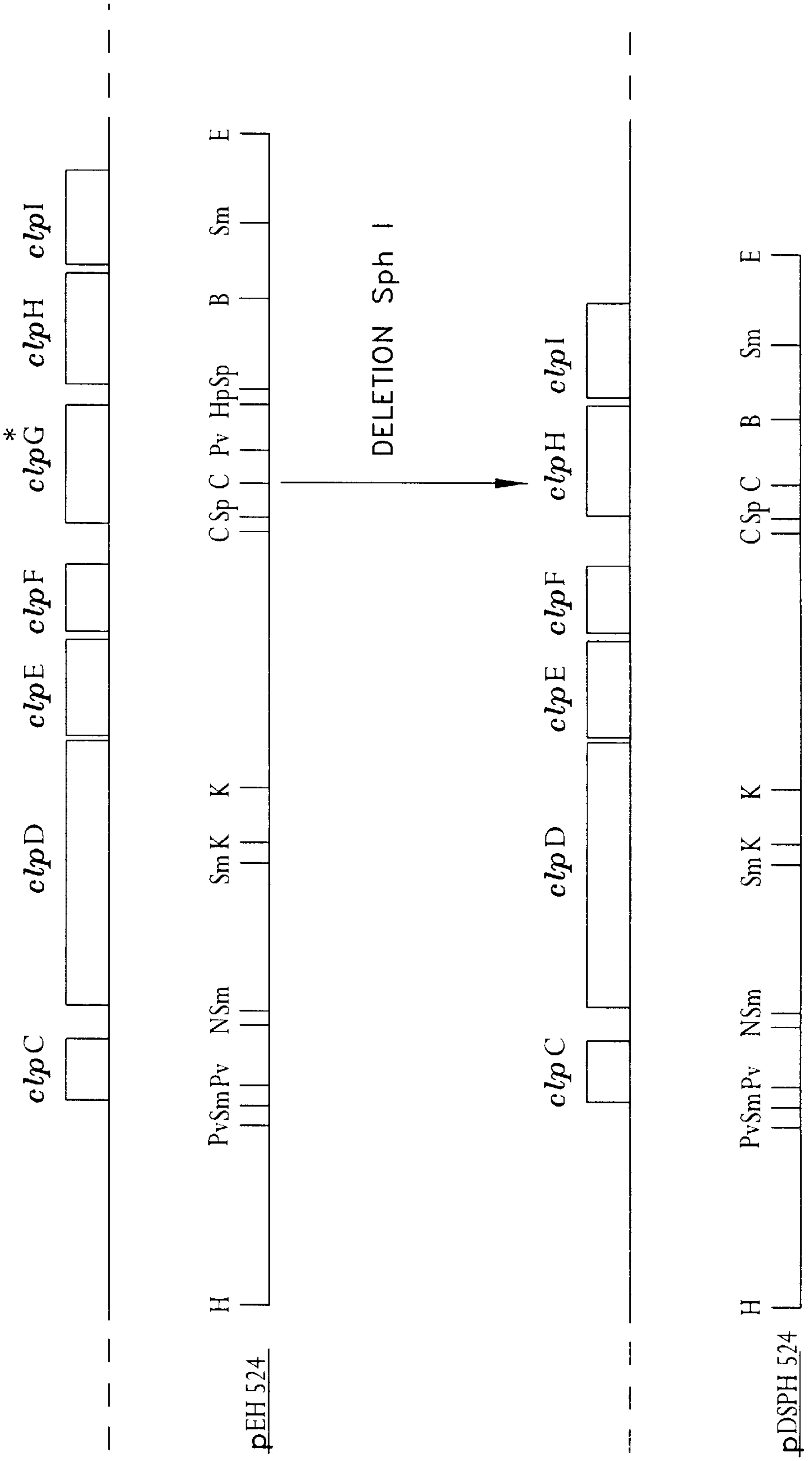
FIG. 10 shows the structures of the pEH524 and pDSPH524 plasmids.

The pDSPH524 plasmid derived from the pEH524 plasmid that contains the CS31A operon (as described by C. Martin et al. in *Microbial Pathogenesis,* Vol. 10 (1991), pp. 429–442) deletes the clpG gene from the sub-unit. For this purpose, the pEH524 is restricted by SphI, and the SphI/SphI fragment with 872 base pairs containing the region that codes for the clpG gene is deleted after recircularization, by the T4 ligase, of the linear plasmid generated by the SphI [fragment]. The deletion extends from a point 60 base pairs downstream of the ATG initiation codon to 96 base pairs downstream of the first TAA stop codon of the clpG gene, as described by J. P. Girardeau et al. in the *Journal of Bacteriology,* Vol. 173 (1991), pp. 7673–7683. The pDSPH524 plasmid is a plasmid that has a low copy number and a type pSC101 replication origin, and that confers resistance to chloramphenicol. FIG. 10 represents the structures of the pEH524 and pDSPH524 plasmids.

II. Construction of the Plasmids that Carry the clpG Genes

1) In the Bluescript SK(+) Vector Plasmid

Figure 11:
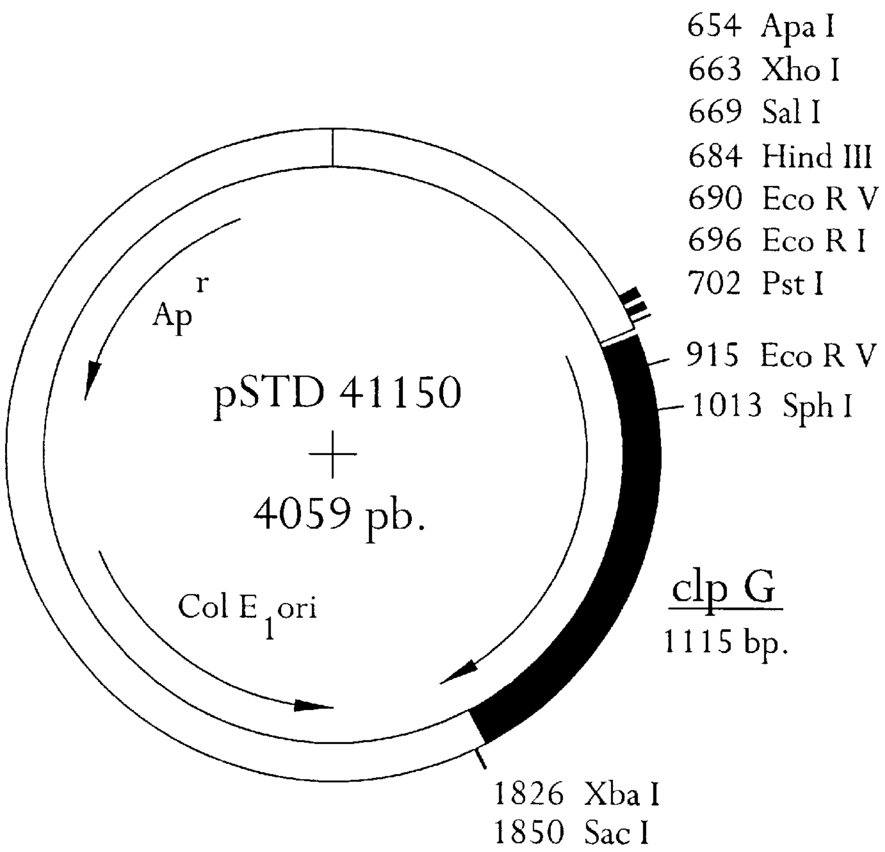
FIG. 11 shows the pSTD41150 plasmid.

FIG. 11 represents the pSTD41150 plasmid.

The PstI/HpaI fragment, with 1.2 kb, as carried by the pEH524 plasmid, containing the promoter region, the coding region, and the terminator region of the clpG gene, was cloned at the PstI/SmaI sites of the Bluescript SK(+) vector plasmid (from Stratagene). In this construction, the transcription of the clpG gene is under the control of its own promoter, and, depending on the Plac promoter of the vector, is oriented in the direction opposite to its transcription direction . The pSTD41150 plasmid obtained through this cloning trans-complements the pDSPH524 plasmid for biogenesis of the CS31A. The PstI site is located 255 base pairs upstream of the ATG initiation codon for the clpG gene.

Figure 12:
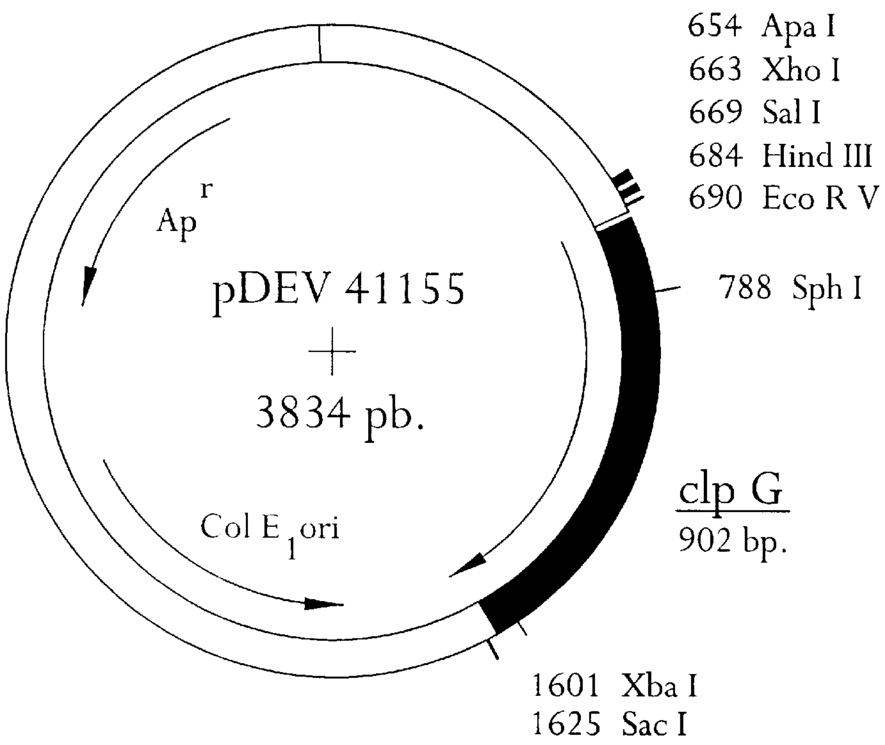
FIG. 12 shows the pDEV41155 plasmid.

FIG. 12 represents the pDEV41155 plasmid.

The pSTD41150 plasmid, which contains only two EcoRV sites, was restricted by EcoRV, and the EcoRV/EcoRv fragment with 225 base pairs was deleted. The first EcoRV site is located 40 base pairs upstream of the ATG initiation codon for the clpG gene, and the second EcoRV site is located in the polylinker of the Bluescript SK(+) vector. The pDEV41155 plasmid resulting from this construction carries the EcoRV/HpaI fragment with 0.92 kb of the clpg gene. This fragment expresses the clpG sub-unit when pDEV41155 is complemented by the pDSPH524 plasmid. The pDEV41155 plasmid, which has a high copy number and a Col EI replication origin, codes for resistance to ampicillin ($Ap^r$).

2) In the pSELECT-1 Vector Plasmid

The pStI/HpaI fragment of the clpG gene that contains the promoter, the coding region, and the terminator region for the clpG gene was cloned in the Bluescript SK(+) vector, as restricted by SmaI and PstI. Then the PstI/XbaI fragment of this recombinant [plasmid] (containing the above-mentioned PstI/HpaI vector) was cloned in the pSELECT-1 vector, as restricted by PstI and XbaI, resulting in the acquisition of the pPSX83 plasmid.

The pSELECT-1 plasmid (from Promega) is a vector with a high copy number. It carries the gene for resistance to tetracycline, and its replication origin (Col EI) is different from that of the pDSPH524 plasmid.

Figure 13:
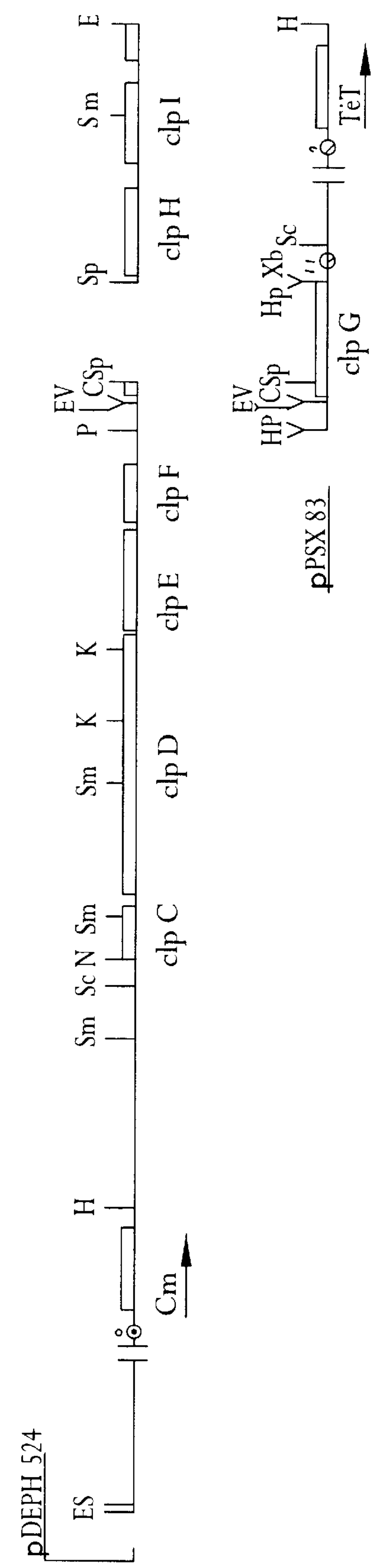
FIG. 13 shows the complementation of CS31A.

The complementation of the CS31A is shown schematically in FIG. 13, in which "E" represents EcoRV, "P" represents PstI, and "Xb" represents XbaI. The process involves the pDSPH524 plasmid and the pPSX83 plasmid, which contain the only gene in the major CS31A sub-unit that is controlled by its own promoter in pSELECT-1. The bacteria that contain both the pPSX83 and pDSPH524 plasmids are positive for CS31A.

F) PRESUMPTIVE IDENTIFICATION OF THE REGIONS OF THE clpG SUB-UNIT THAT CAN ACCEPT THE ADDITION OF AMINO ACIDS OR HETEROLOGOUS REPLACEMENTS To obtain this information, the following three strategies were implemented:

Definition of the variable regions that can accept modifications, based on a comparison of the primary sequenes of the CS31A protein with those of the K88 and F41 proteins;

Research of the continuous epitopes in the CS31A protein. The continuous epitopes often correspond to variable regions of the protein. The study of their accessibility to antibodies also provides information about their location in the native protein;

Random insertional mutagenesis, which consists of randomly inserting into the clpG gene a short synthetic oligonucleotide that contains the recognition site for a restriction nuclease (i.e., a so-called "linker"). The introduction of this new restriction site makes it possible to insert a heterologous sequence later. Analysis of the expression of the proteins modified through in vivo intergenic complementation and by means of immunoblotting using specific antibodies directed against the clpG protein constitutes the basis for the evaluation of the degree of permissivity of this protein. The permissive regions are then located and identified, after an analysis of restriction and nucleotide sequencing.

I. Sequence Comparison

Figure 14:
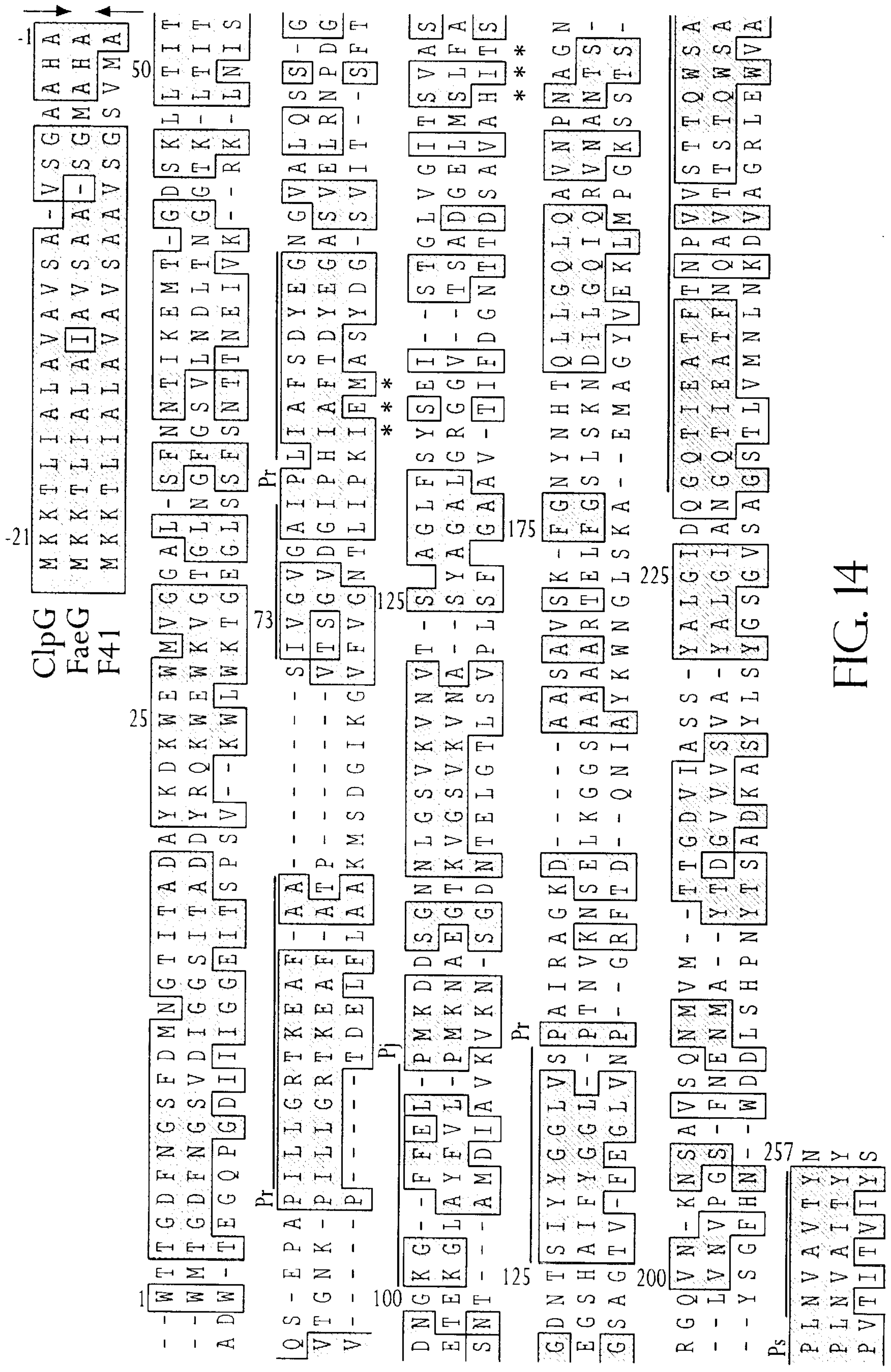
FIG. 14 shows the alignment of the primary sequences deduced for the CS31A (SEQ ID NO:2), K88 (SEQ ID NO:3) and F41 (SEQ ID NO:4) antigens.

FIG. 14 represents the alignment of the primary sequences deduced for the CS31A, K88, and F41 antigens. A comparison of these sequences indicates that the CS31A displays 44 percent identity with the sub-unit of the K88 antigen, and 24 percent identity with the sub-unit for the F41 antigen. In spite of the major discrepancies observed in the primary sequenes for CS31A and K88, the conservation of several hydrophobic regions systematically associated with the presence of a proline remainder suggests that the two sub-units take on a similar conformation. The variable regions that may be permissive are defined by the amino acids located at positions 10 and 58 in FIG. 9 for region B, at positions 123 and 164 in FIG. 9 for region C, and at positions 183 and 257 in FIG. 9 for region D.

II. Detection of Continuous Epitopes in the CS31A Protein

Because the immune responses against a protein presented in native form or in denatured form are different, the continuous epitopes have been defined either by means of antibodies directed against the denatured sub-unit, or by means of antibodies directed against the native protein that has a high molecular weight.

1) Definition of Continuous Epitopes in the Denatured Sub-units

The presence of continuous epitopes was researched through the measurement of the reactivity of the polyclonal antiserums prepared in four rabbits (L1, L2, L3, and L4) against the denatured protein in relation to the 257 overlapping nonapeptides that cover the CS31A sequence.

Figure 15A:
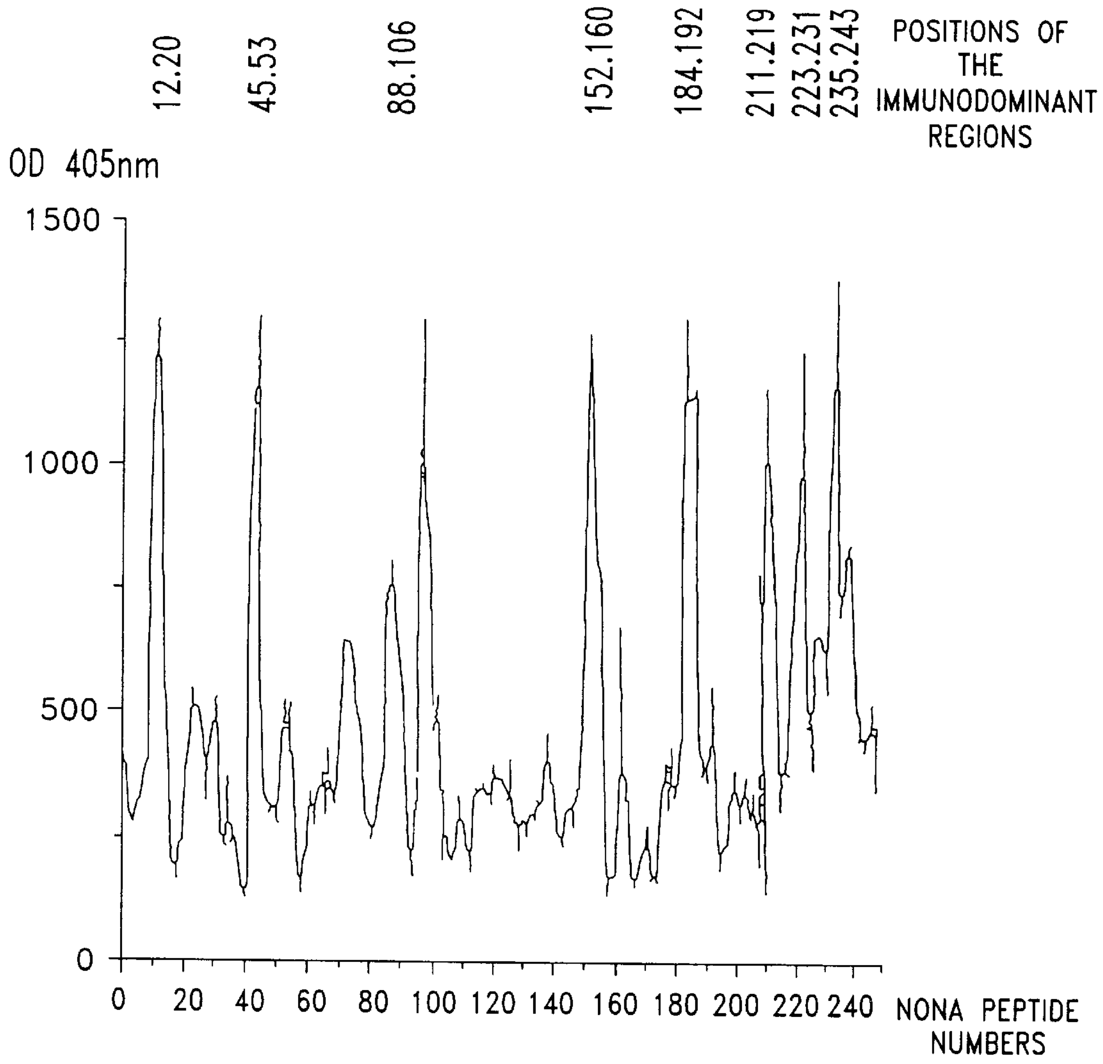
FIG. 15 shows the reactivity profile of the nonapeptides in relation to the L2 antiserum directed against denatured CS31A protein.
Figure 15B:
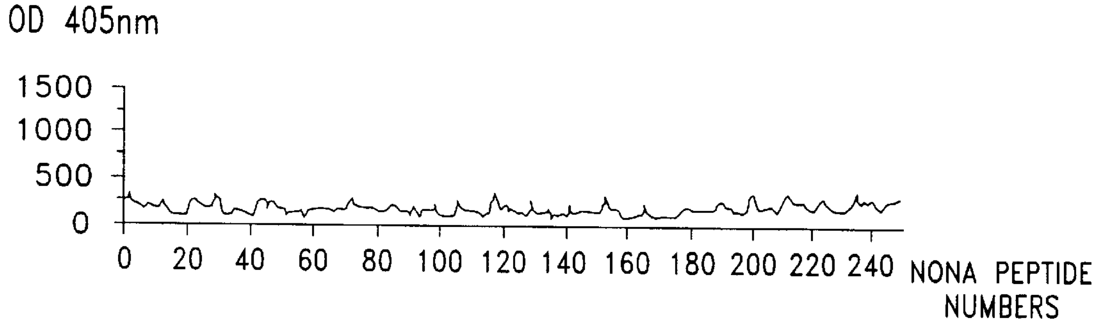

FIG. 15 shows, at "A", the reactivity profile of the nonapeptides in relation to the L2 antiserum directed against the denatured CS31A protein. FIG. 15 shows, at "B", the reactivity profile of the nonapeptides in relation to a non-specific control antiserum. This control antiserum is the one from a rabbit that was immunized in accordance with the same protocol, but against a different protein, i.e., the OmpA protein.

FIG. 16 represents the immunoreactive regions recognized by the antiserums, as produced in the four rabbits, against denatured CS31A.

FIGS. 15 and 16 show that the four antiserums recognize essentially 6 regions that contain the continuous epitopes of the denatured molecule.

The following peptides were selected: 10–19; 37–58; 88–106; 144–172; 184–219; and the C-terminal region (232–257). Individually, the serums recognize shorter sequences (consisting of 5 to 7 remainders).

These immunodominant regions that are recognized by all of the animals are supplemented by regions that are recognized only be certain antiserums. This is the case with the 37–44 and 200–207 peptides for the L1 rabbit, and with the 84–93 peptide for the L3 and L4 rabbits.

2) Determination of the Continuous Epitopes in the Native Protein

These epitopes were determined in accordance with the same procedure, but the reactivity of the peptides was observed with antiserums that were prepared against the native protein that has a high molecular weight.

FIG. 17 represents the immunoreactive regions recognized by the anti-CS31A antiserums produced in the rabbits (N1 ) and (N2). The underlined sequence 176–196 corresponds to the immunodominance region of the native CS31A protein.

The antiserums of both of these rabbits recognize only the 190–197 region that constitutes the only continuous epitope that is present on the native protein.

III. Determination of the Accessibility of the Continuous Epitopes

The measurement of the antigenicity of the peptides defined earlier makes it possible to determine their accessibility at the surface of the native molecule. Two different methods were utilized:

1) First Method:

Modification of the epitope-scanning profile after absorption of the polyclonal antibody by the native protein.

Figure 18A:
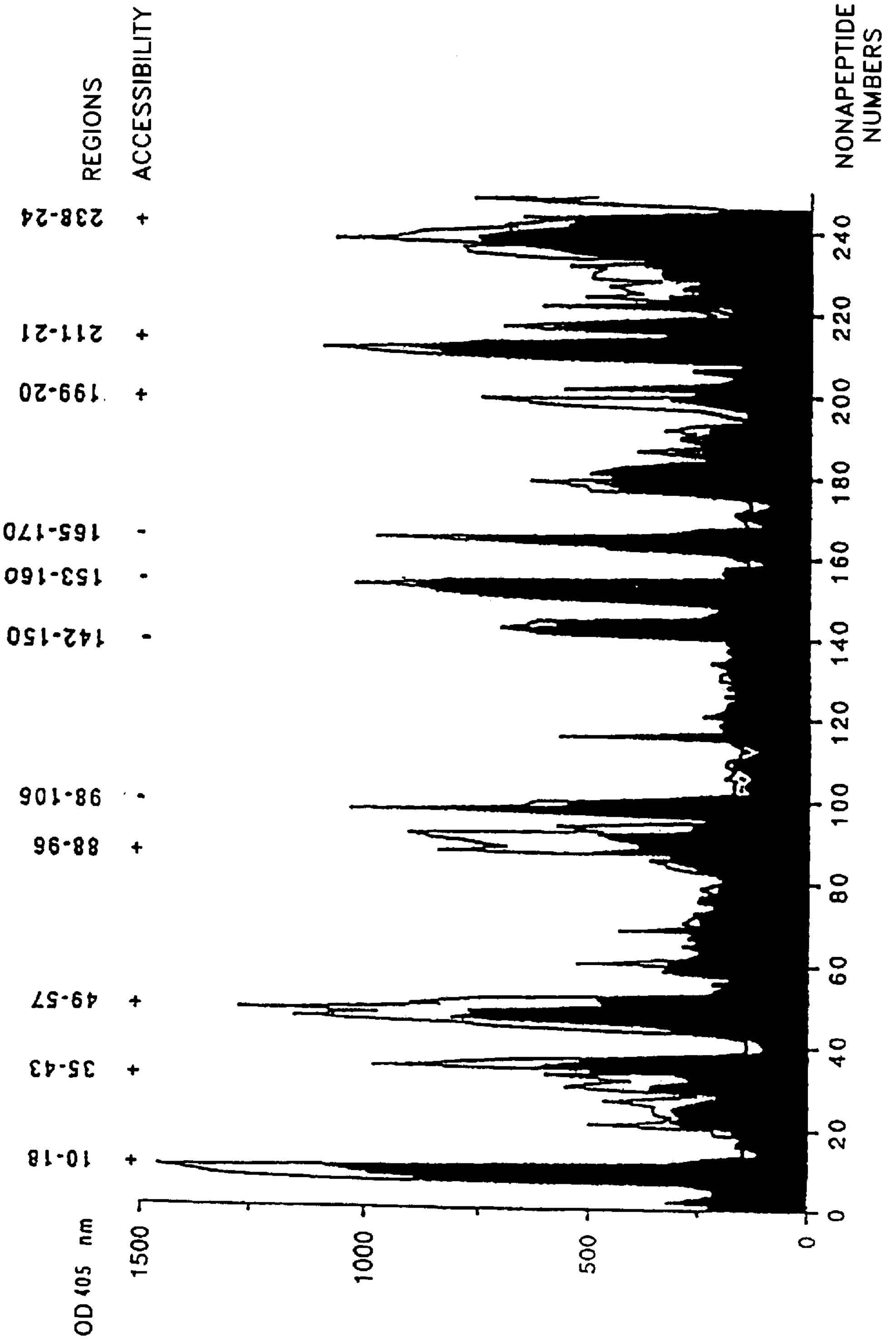
FIG. 18 shows the scanning peptide profiles obtained with anti-CS31A antiserums.
Figure 18B:
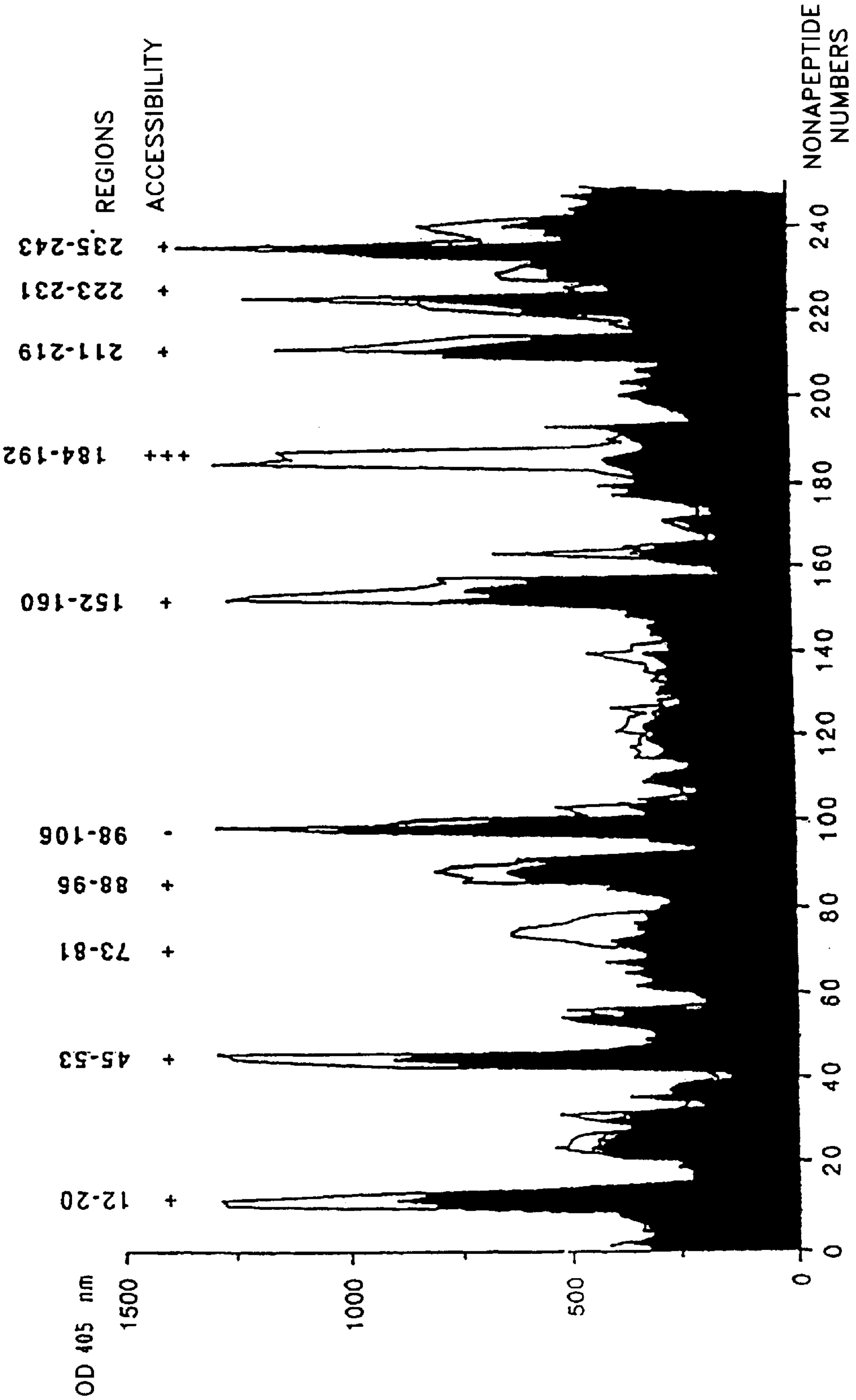

Three situations were observed, as indicated by the example in FIG. 18, which represents the scanning peptide profiles obtained with the anti-CS31A antiserums, before absorption by the native CS31A protein (the white peaks), and after absorption (the gray peaks), with "A" representing rabbit L1 and "B" representing rabbit L2:

Region 98 to 106 and region 151 to 160: The reactivity of the antiserum absorbed is not modified. The peptides are not accessible at the surface of the molecule.

Region 184 to 191, with the serum from rabbit L2, and region 200 to 207, with the serum from rabbit L1, the reactivity of the antiserum is completely negated. The peptides are accessible, and the corresponding antibodies have a good affinity.

Regions 10 to 19, 46 to 58, 92 to 99, and 235 to 245: The reactivity to peptides is more or less strongly reduced. Accessibility is partial, or the affinity of the antibodies for the peptide present in the native protein is weak.

2) Second Method:

Capture of an antipeptide by the native protein.

The measurement principle consists of either:

Measuring, in the presence of the native protein, the quantity of antipeptide captured by the corresponding peptide absorbed on a solid phase (i.e., ELISA accessibility), or Directly measuring the quantity of antipeptide captured by the native protein immobilized on nitrocellulose or on plastic.

a) Production of Antipeptides

Five antipeptides were produced against five synthetic peptides from 15 remainders, corresponding to the immunodominant regions defined earlier. Each antipeptide was prepared in two rabbits, as described above in the "Materials and Methods" section. Table 3 below presents the sequence, the position, and the peptides in the corresponding region.

TABLE 3

| Peptide | Sequences positions | anti-peptide | Positions des nonapeptides réactifs | Nonapeptide le plus réctif |
|---|---|---|---|---|
| Y-15-A | (Y)-GDSKLLTITOSEPA SEQ ID NO: 5<br>44 57 | Y-15-A(H) | 42–57 | GDSKLLTIT SEQ ID NO: 10 |
| Y-15-D | (Y)-GDNGKGFFELPMKD SEQ ID NO: 6<br>97 110 | Y-15-D(K) | 99–112 | FELPMKDDS SEQ ID NO: 11 |
| D-15-I | DNTSIYYGGLVSPAI SEQ ID NO: 7<br>148 162 | D-15-I(C) | 144–165 | (I) YYGGLVSPA SEQ ID NO: 12 |
| G-15-Q | GOLOAVNPNAGNRGQ SEQ ID NO: 8<br>185 199 | G-15-Q(F) | 184–201 | QLQAVNPNA SEQ ID NO: 13 |
| T-15-P | TFTNPVVSTTOWSAP SEQ ID NO: 9<br>235 249 | T-15-P(A) | 238–253 | STTQWSAPL SEQ ID NO: 14 |

Key:
//column headings:
Peptide
Sequences and positions
Antipeptide
Positions of the reactive nonapeptides
The most reactive nonapeptide//

The five peptides are located in the primary sequence in FIG. 19.

b) Verification of the Specificity and Titer of the Antipeptides

This test was carried out in accordance with ELISA procedures, through the capture of antibodies on peptides fixed on Immulon II plates (at a ratio of 0.5 μg per well). The titer and the cross-reactivity of the antipeptides are indicated in Table 4 below.

TABLE 4

| | Peptide | | | | |
|---|---|---|---|---|---|
| Anti-peptide | Y-15-A | Y-15-D | D-15-I | G-15-Q | T-15-I |
| Y-15-A (H) | >3200 | 0 | 0 | 0 | 0 |
| Y-15-D (J) | 0 | >16000 | 0 | 0 | 500 |
| Y-15-D (K) | 0 | >32000 | 0 | 0 | 500 |
| D-15-I (C) | 0 | 0 | 8000 | 0 | 0 |
| D-15-I (D) | 0 | 0 | >32000 | 500 | 250 |
| G-15-Q (E) | 128 | 128 | 128 | >32006 | 64 |
| G-15-Q (F) | 0 | 32 | 0 | 32000 | 0 |
| T-15-P (A) | 0 | 0 | 0 | 0 | 4000 |
| T-15-P (B) | 128 | 250 | 64 | 32 | 4000 |

TABLE 4-continued

| | Peptide | | | | |
|---|---|---|---|---|---|
| Anti-peptide | Y-15-A | Y-15-D | D-15-I | G-15-Q | T-15-I |
| Serum preimmun | 250<br>(H) | 250<br>(J + K) | 64<br>(C + D) | 64<br>(E + F) | 128<br>(A + B) |

Key:
//top row labels:
Peptide
Antipeptide
Serum
Pre-immun//

In Table 4, the letters in parentheses correspond to the designation of the immunized rabbit. Two antipeptides were produced for each peptide, except for peptide Y-15-A.

c) ELISA Accessibility

In order to avoid the problems associated with the differences in affinity of the competing antipeptides (i.e., the native protein and the peptide), the antipeptides are first absorbed on the native protein (or on the bacteria that produce it). After elimination of the imnmunocomplexes by centrifuging, the residual titer of the antipeptide is measured through capture of the antibody on the corresponding peptide immobilized on an Immulon II plate. The antipeptides have been used at dilutions determined in accordance with the titration curves, which correspond to a 50 percent reduction in optical density at a wavelength of 405 nm.

The accessibility results for the continuous epitopes of the CS31A protein are presented in Table 5 below.

TABLE 5

| Sequences | Position | Accessi-bilite Pepscan (graphe) | Accessi-bilite Pepscan (indice) | Accessi-bilite anti-peptide | Conclu-sion accessi-bilite |
|---|---|---|---|---|---|
| FDMNGTITA SEQ ID NO: 15 | 10–18 | +(L1) | – | | (+) |
| MNGTITADA SEQ ID NO: 16 | 12–20 | +(L2)<br>–(L1.8) | – | | |
| FNNTIKEMT SEQ ID NO: 17 | 35–43 | +(L1)<br>–(L1.8) | + | | (+) |
| LTITQSEPA SEQ ID NO: 18 | 49–57 | +(L1) | ++ | | |
| DSKLLTITTQ SEQ ID NO: 19 | 45–53 | +(L2)<br>+(L1.8) | – | | +<br> |

TABLE 5-continued

| Sequences | Position | Accessibilite Pepscan (graphe) | Accessibilite Pepscan (indice) | Accessibilite anti-peptide | Conclusion accessibilite |
|---|---|---|---|---|---|
| (Y)-GDSKLLTITQSEPA SEQ ID NO: 5 (Y-15-A) | 44–57 | | | + | + |
| VGVGAIPLI SEQ ID NO: 20 | 73–81 | +(L2) | ++ | | (+) |
| GNGVALQSS SEQ ID NO: 21 | 88–96 | +(L1) | ++ | | |
| GNGVALQSS SEQ ID NO: 21 | | +(L2)<br>+(L1.8) | − | | (+) |
| DNGKGFFEL SEQ ID NO: 22 | 98–106 | −(L1) | − | | |
| DNGKGFFEL SEQ ID NO: 22 | | −(L2)<br>−(L1.8) | − | | − |
| (Y)-GDNGKGFFELPMKD SEQ ID NO: 6 (Y-15-D) | 97–100 | | | − | |
| TSVASGNT SEQ ID NO: 23 | 142–150 | −(L1)<br>−(L1.8) | − | | − |
| YYGGLVSPA SEQ ID NO: 24 | 153–161 | −(L1) | + | | |
| IYYGGLVSP SEQ ID NO: 25 | 152–160 | +(L2)<br>−(L1.8) | ++ | | |
| DNTSIYYGGLVSPAI SEQ ID NO: 7 (D-15-I) | 148–162 | | | − | − |
| GKDAASAVS SEQ ID NO: 26 | 165–173 | −(L1)<br>−(L1.8) | +++ | | (+) |
| LGQLQAVNP SEQ ID NO: 27 | 184–192 | +++(L2) | +++ | | +++ |
| QVNKNSAVS SEQ ID NO: 28 | 199–207 | +(L1)<br>+(L1.8) | +++ | | +++ |
| GQLQAVNPNAGNRGQ SEQ ID NO: 8 (G-15-Q) | 185–199 | | | +++ | +++ |

Key:
//column headings:
Sequences
Position
Accessibility (as indicated by Pepscan) (graph)
Accessibility (as indicated by Pepscan) (index)
Antipeptide accessibility
Conclusion of accessibility//

FIG. 20 represents the ELISA competition for measuring the accessibility of the peptide in the native CS31A protein. The test curve is shown in solid dots, and the control curve is shown in open dots.

Three situations were observed:

- With the G15Q (185–199) and T15P (235–249) antipeptides, a reduction in optical density was observed that was proportional to the quantity of the native protein in competition with the peptide. The antipeptides were absorbed by the corresponding regions on the native protein. The specificity of the system was verified by the stability of the titer of the antipeptide in the presence of either a foreign protein (BSA) or bacteria containing a plasmid deleted in the region carrying the structural gene (pDSPH524).
- With the Y15A (44–57) antipeptides, the absorption of the antipeptide could be measured only at high concentrations of the native protein. This indicates either partial accessibility in the native protein, or a low affinity of the antipeptide for the native protein.
- With the Y15D (97–110) and D15I (148–162) antipeptides, the test curves (solid dots) and the control curves (open dots) were parallel, and there was no relationship between the residual titer of the antipeptide and the amount of the native protein used for the competition.

d) Capture of the Antipeptide by the Native Protein in a DOT-BLOT

Nitrocellulose membranes on which a series of dilutions (ranging from 120 to 0.4 ng) of purified CS31A protein (either native or denatured by heat) was deposited were placed in contact with the following antibodies:

- Each of the five antipeptides (at dilutions between 1/50 and 1/500);
- The polyclonal antiserum directed against the denatured purified sub-units (at a dilution of 1/500); and
- An antiserum (31AL) that recognizes only the native protein (at a dilution of 1/100).

The fixation of the antibodies on the immobilized antigens was measured in the same manner described in the "Materials and Methods" section above.

Figure 21:
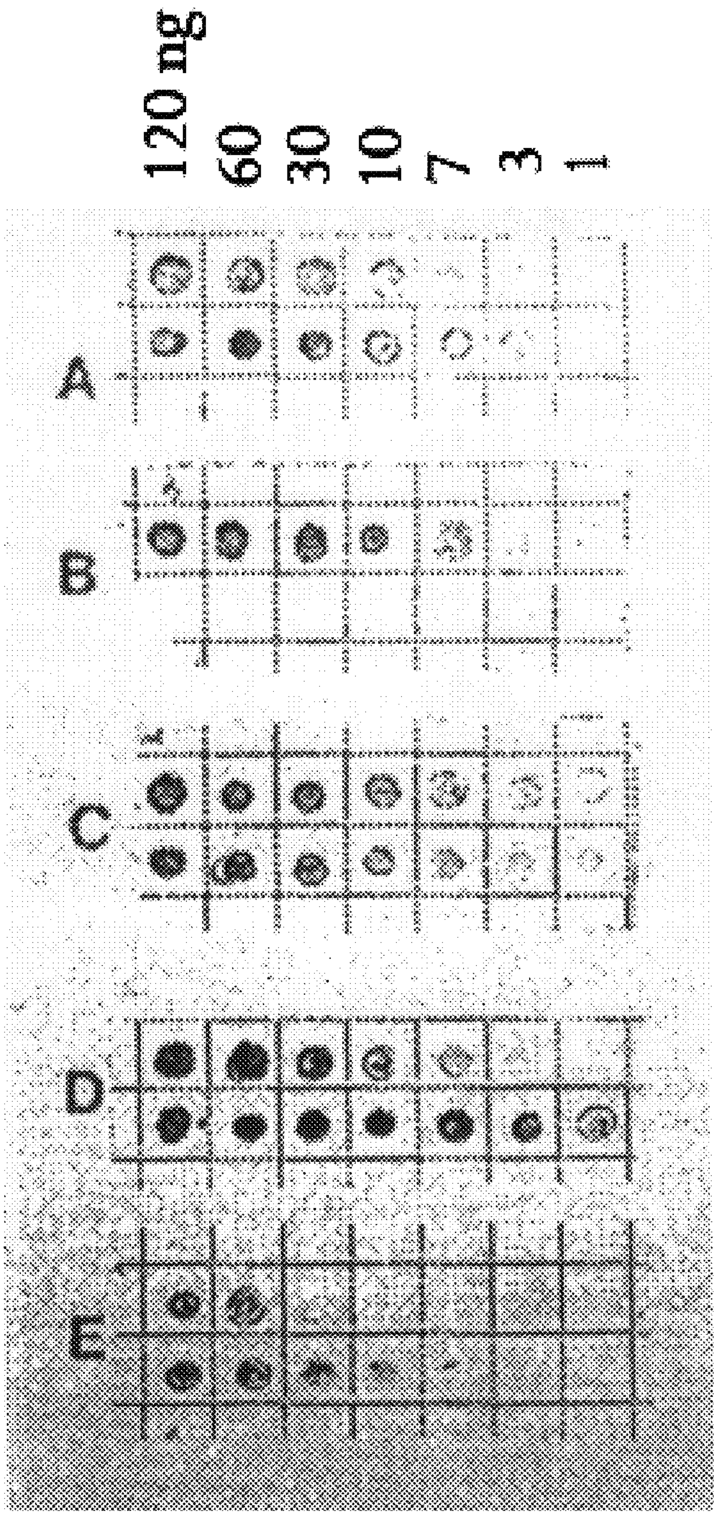
FIG. 21 is a photograph of membranes showing the reactivity of various antibodies in relation to immobilized antigen.

FIG. 21 is a photograph of the membranes showing the reactivity of the various antibodies in relation to the immobilized antigen.

| | |
|---|---|
| Line A: | The antibodies are directed against the denatured protein. It is shown that the same quantity of antigen (either native or denatured) is immobilized on the membrane. |
| Line B: | The 31AL antiserum indicates that the antigen that is not denatured by heat is properly immobilized in native form. |
| Line C: | The G15Q antipeptide recognizes the peptide (185–200) of the native or denatured protein. The peptide is therefore accessible and the antipeptide has a good affinity, regardless of the configuration of the molecule. |
| Line D: | The Y15A, D15I, and T15P antipeptides recognize the denatured form better than the native form when they are slightly diluted (1/50). At stronger dilutions (1/500) no reaction was observed. The weakest reactivity of the peptides in the native protein is linked to either its weak accessibility or to the weak affinity of the antipeptide. |
| Line E: | The Y15D antipeptide recognizes only the denatured antigen. The 97–110 peptide does not appear to be accessible in the native protein. |

3) Conclusions about the Study of Accessibility of Continuous Epitomes Identified in CS31A, and the Properties of the Regions that Contain the Continuous Epitomes The methods used give good indications of the accessibility of the 44–57, 97–110, and 185–199 peptides. On the other hand, the results do not allow a clear determination to be made of the accessibility of the other two peptides (see Table 5 above).

Peptide 44–57: The results obtained indicate that this region is accessible in the native protein. However, the antipeptide (Y15A) appears to have a low affinity for the peptide in its natural environment.

Peptide 97–110: All of the results indicate that this region is not accessible in the native protein.

Peptide 195–199: All of the results indicate that this region is very accessible, and that the corresponding antipeptide (G15Q) has a good affinity for the peptide, regardless of its configuration. Furthermore, the disappearance of the reactivity of the 183–191 and 199–207 regions observed by means of so-called "epitope scanning" after absorption of antibodies by the native protein indicates that a large region that contains at least 24 remainders (183–207) appears to be easily accessible to the antibodies.

Peptide 148–162: The results generally indicate the low accessibility of this region in the native protein. However, the Dot-Blot reactivity of the D15I antipeptide in relation to the native protein conflicts with the other results. The accessibility of this region remains to be determined, because the results do not allow a distinction to be made between the non-accessibility of the region and the inferior affinity of the D15I antipeptide.

The C-terminal region: This region appears to be accessible, but the superimposition of the continuous epitopes in this region does not allow a good determination to be made of the accessibility of each of the epitopes.

All of the information collected about the properties of the regions that contain continuous epitopes is presented in Table 6 below.

TABLE 6

| Région immunodominate | Position des épitopes continus<br>accessibilité des épitopes<br>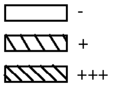 | Hydrophylie | Flexibilité |
|---|---|---|---|
| 10–19 | 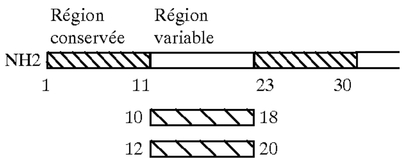 | +<br>+ | +<br>+ |
| 38–58 | 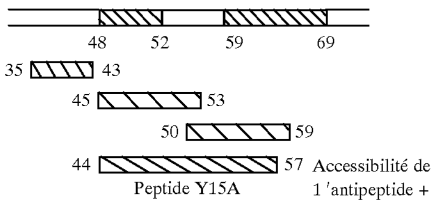 | +<br>+<br>+ | +<br>+<br>+ |
| 88–106 | 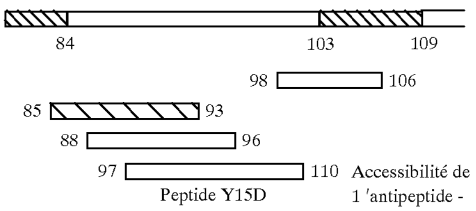 | –<br>+<br>+ | –<br>+++<br>+ |

TABLE 6-continued

| Région immunodominate | Position des épitopes continus<br>accessibilité des épitopes<br>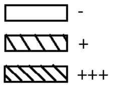 | Hydrophylie | Flexibilité |
|---|---|---|---|
| 144–172 | 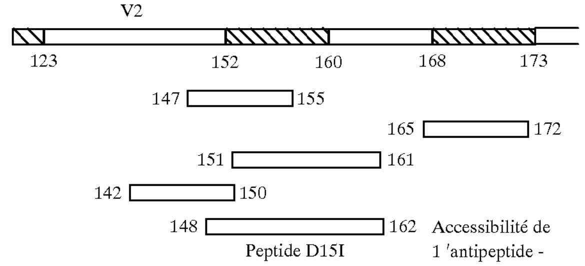 | +<br>−<br>+ | +<br>+<br>+ |
| 184–220 | 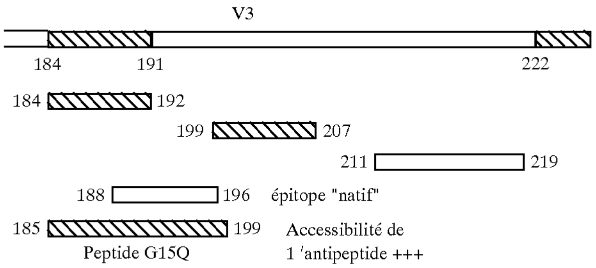 | +<br>+<br>+ | +<br>+<br>+ |
| 223–245 | 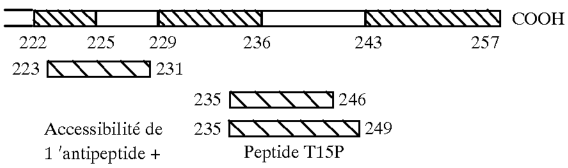 | | ++ |

Key:
//column headings:
Immunodominant region
Position of the continuous epitopes
Accessibility of the epitopes
Hydrophilia
Flexibility
center-column call-outs, starting with the "10–19" row:
Retained region
Variable region
The Y15A peptide
Accessibility of the antipeptide
The Y15D peptide
Accessibility of the antipeptide
The D15I peptide
Accessibility of the antipeptide
The G15Q peptide
"Native" epitope
Accessibility of the antipeptide
The T15P peptide
Accessibility of the antipeptide 4) General Properties of the Regions that Contain the Continuous Epitopes (Table 6)

Region 10–19: This region is strongly immunogenic, and all of the serums directed against the denatured protein (i.e., the so-called "anti-D" serums) react against it. The epitope is located in a variable region that is weakly hydrophilic, flexible, and accessible.

Region 38–58: This region is very immunogenic. The various anti-D serums make it possible to determine three overlapping epitopes located in a large variable region interrupted by 4 retained remainders. The region is hydrophilic, very flexible, and accessible to the antibodies.

Region 74–80: This region is immunogenic in certain animals. The epitope recognized by the anti-D serums is located in a short variable region flanked by very conservative regions. The region that contains the epitope is hydrophobic and non-flexible; however, it is accessible to the antibodies.

Region 88–106: This very immunogenic region is recognized by all of the anti-D serums. Three epitopes can be defined that are located in the variable region adjacent to the P3 cluster. The 88–99 epitope is located in a hydrophilic region that is flexible and accessible. On the other hand, the immediately adjacent 98–106 epitope is part of a hydrophobic region that is not flexible and not accessible to the antibodies. The Y15D antipeptide directed against the 97–110 sequence does not react against the native protein.

Region 144–172: The 151–160 sequence is very immunogenic in all of the animals. The 144–151 and 165–172 sequences are recognized by only one animal. The 151–160 epitope is located in a very hydrophobic and non-flexible region. The other sequences are hydrophilic but only slightly flexible. None of the epitopes is antigenic in the native protein. The D15I antipeptide (148–162) is not fixed by the protein.

Region 184–220: This region is the most immunoreactive region of the protein. It contains the only continuous epitope (190–197) in the native protein. The 190–197 region contains the NPN sequence that is capable of forming a twist in the polypeptide chain that could explain this strong immunoreactivity. All of the animals recognize the 184–197 region, but the 200–207 region reacts only with one single animal. The 184–191 epitope is located downstream of the NPN sequence in a preserved region that is hydrophobic and inflexible but accessible to the antibodies. The G15Q (185–199) antipeptide reacts strongly against the native protein. The 200–207 epitope is located in the V3 variable regions, which is hydrophilic, flexible, and easily accessible to the antibodies. The 211–219 region is strongly immunogenic in all of the animals, and is located in a hydrophobic, flexible, and non-accessible portion of the V3 region. Thus, the 184–220 region appears to be very immunogenic; however, its antigenicity is limited to the upstream (184–207) portion.

Region 223–245: The C-terminal region is strongly immunoreactive; however, the superimposition of the numerous epitopes complicates the task of defining them. The 223–231 epitope is located specifically and exactly in a variable region that is weakly hydrophilic but very flexible. The 235–245 epitope is located in a hydrophobic variable region that is only slightly flexible. The accessibility study with the T15P (235–249) antipeptide indicates that the entire region is antigenic in the native protein.

5) General Conclusions Regarding the Immunostructural Study

The foregoing findings can be summarized in the following conclusive points:

The immunostructural study clearly locates the continuous epitopes in variable regions that are generally flexible, hydrophilic, and accessible to the antibodies in the native protein.

The insertions, by means of directed mutagenesis, of foreign epitopes into the variable immunoreactive regions will make it possible (provided that the regions are permissive) to place the foreign sequences in a configurational environment which, because of its flexibility and accessibility, favors a good presentation to the immune system.

Provided that they are permissive, the following variable immunoreactive regions can be selected for insertion of the foreign epitopes: 10 to 19; 38 to 58; 88 to 106; 144 to 172; 184 to 220; and 223 to 245.

The V3 (184–220) region, which has the only continuous epitope in the native protein, has the immunological properties (i.e., immunogenicity and antigenicity) that are the most favorable for the presentation of foreign epitopes.

IV. Random Insertional Mutagenesis in the ClpG Protein

Figure 22:
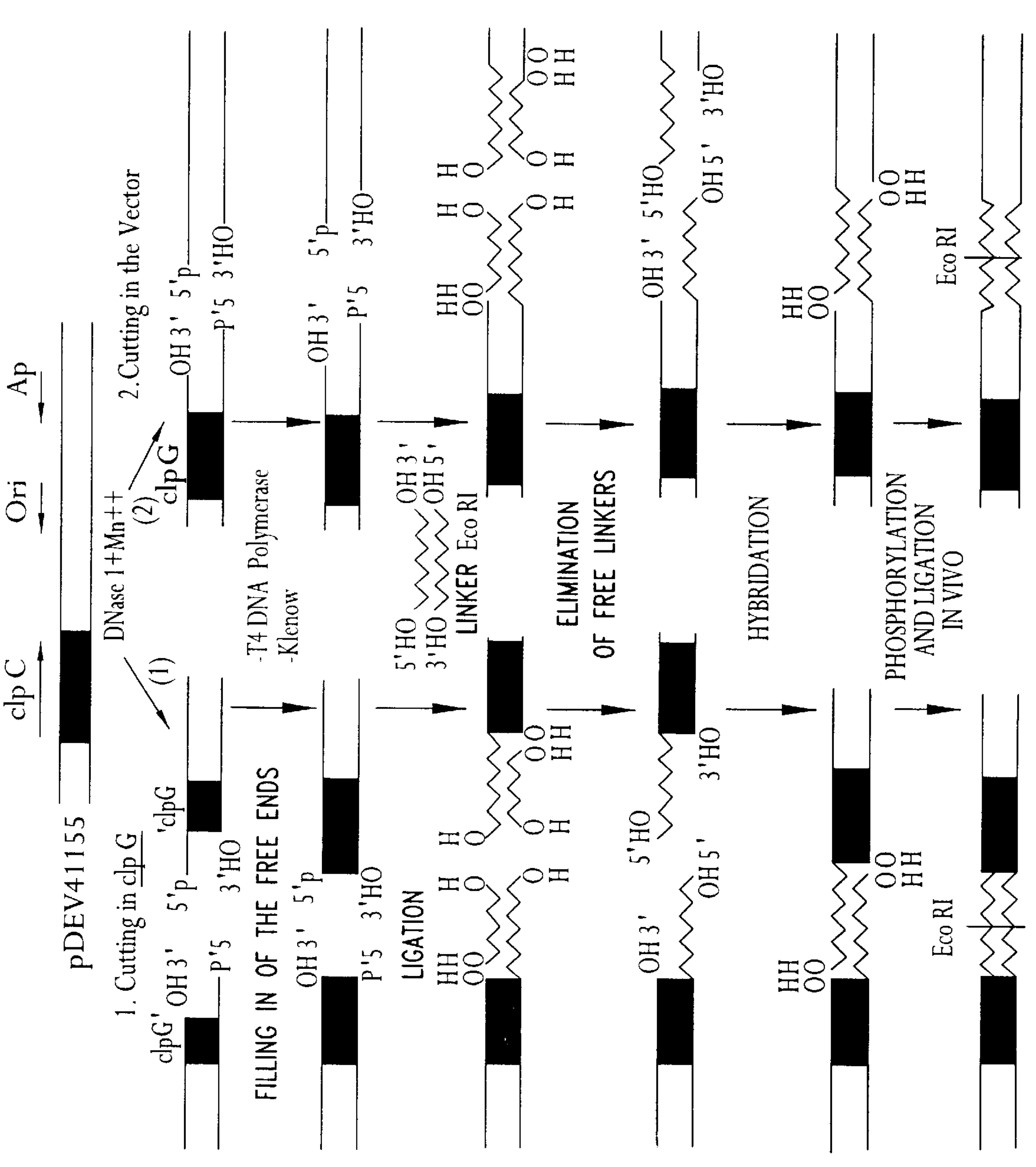
FIG. 22 shows introduction of a single unique EcoRI restriction site in pDEV41155 plasmid that carries the ClpG gene.

1) Random Insertion of the EcoRI Linkers and of Heterologous Sequences in the clpG Gene The introduction, by means of random mutagenesis, of a single unique EcoRI restriction site in the pDEV41155 plasmid that carries the clpG gene is illustrated schematically in FIG. 22.

The pDEV41155 plasmid is partially hydrolyzed by the Dnase I in the presence of $Mn^{++}$, in such a way that approximately ⅓ of the molecules are obtained in linear form. Thus, multiple cuttings of the plasmid by the Dnase I are avoided. The projecting ends of the pDEV41155 plasmid linearized in this way are transformed into free ends as a result of the effect of the T4 DNA polymerase and of the Klenow fragment of the DNA polymerase of *E. coli*. The linear DNA molecules with 3.8 kilobases that had been subjected to the action of the polymerases were then isolated and purified through the use of agarose gels. The recircularization of the plasmids was accomplished in the presence of an excess of non-phosphorylated EcoRI linkers and in the presence of the T4 DNA ligase. A total of five EcoRI linkers of various sizes (e.g., 8, 10, and 12 mers) were used in order to obtain at least one insertion that did not change the reading frame of the clpG gene, i.e.:

GGAATTCC (8 mers) SEQ ID NO:29
GCGAATTCGG (10 mers) SEQ ID NO:30
CGOAATTCCG (10 mers) SEQ ID NO:31
CCCGAATTCGGG (12 mers) SEQ ID NO:32
CCGGAATTCCGG (12 mers) SEQ ID NO:32

After transformation of the DH5α *E. coli* strain, the transformation mixture was placed directly in a culture medium. The total amount of plasmidic DNA extracted from this culture was restricted by the EcoRI enzyme. A linear mixture of DNA with 3.8 kilobases was recovered and purified by electrophoresis on agarose gel. This stage, consisting of digestion by EcoRI, made it possible to isolate only the pDEV41155 plasmids that had inserted the monomeric EcoRI linkers, and to discard the plasmids that had no EcoRI linkers or those that had incorporated multimeric EcoRI linkers.

The linear plasmids that contained an EcoRI site were subjected to the effect of T4 DNA ligase in the presence of a KmR cassette that codes for the 3'-phosphotransferase aminoglycoside that provides resistance to kanamycin.

Figure 23:
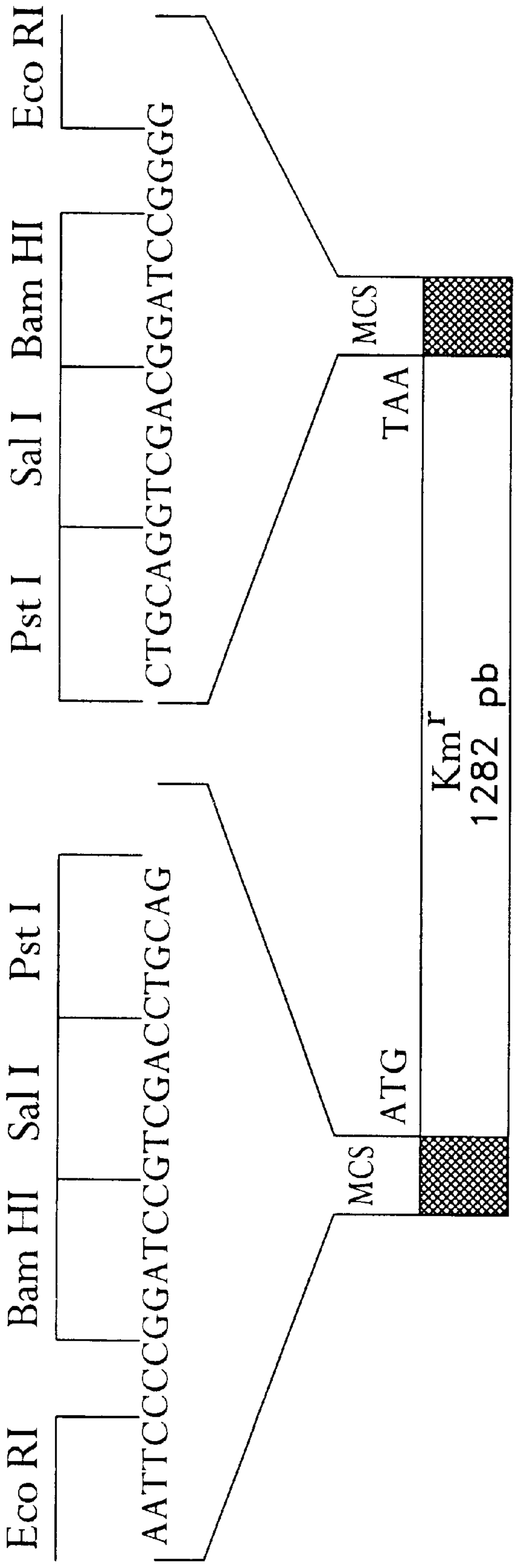
FIG. 23 shows the $Km^r$ cassette with its multiple and symmetrical restriction sites (SEQ ID NO:62 and (SEQ ID NO:63).
Figure 24A:
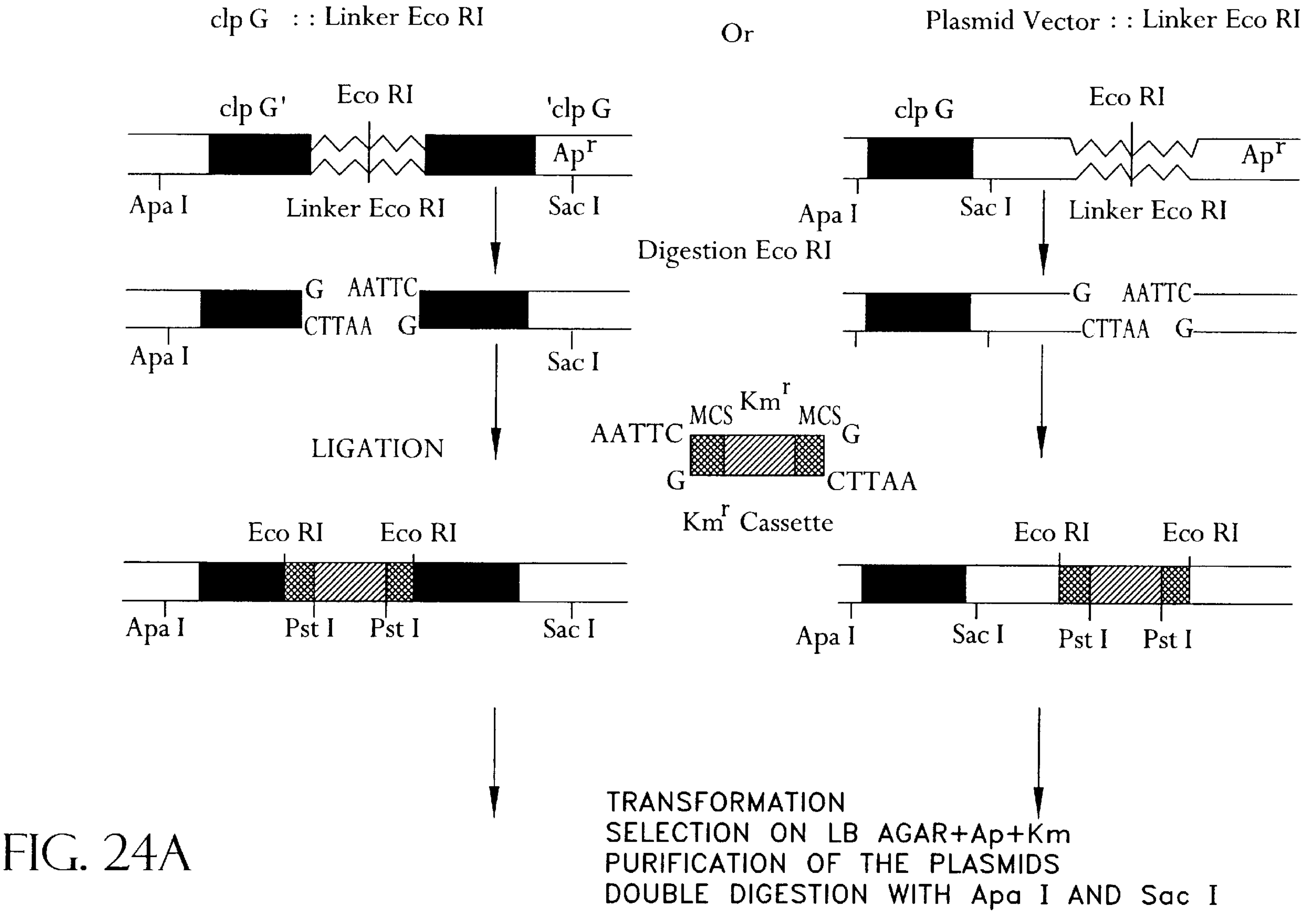
FIG. 24 shows the procedure for positive selection of EcoRI linkers and of EcoRI-PstI-EcoRI polylinker in the ClpG gene.
Figure 24B:
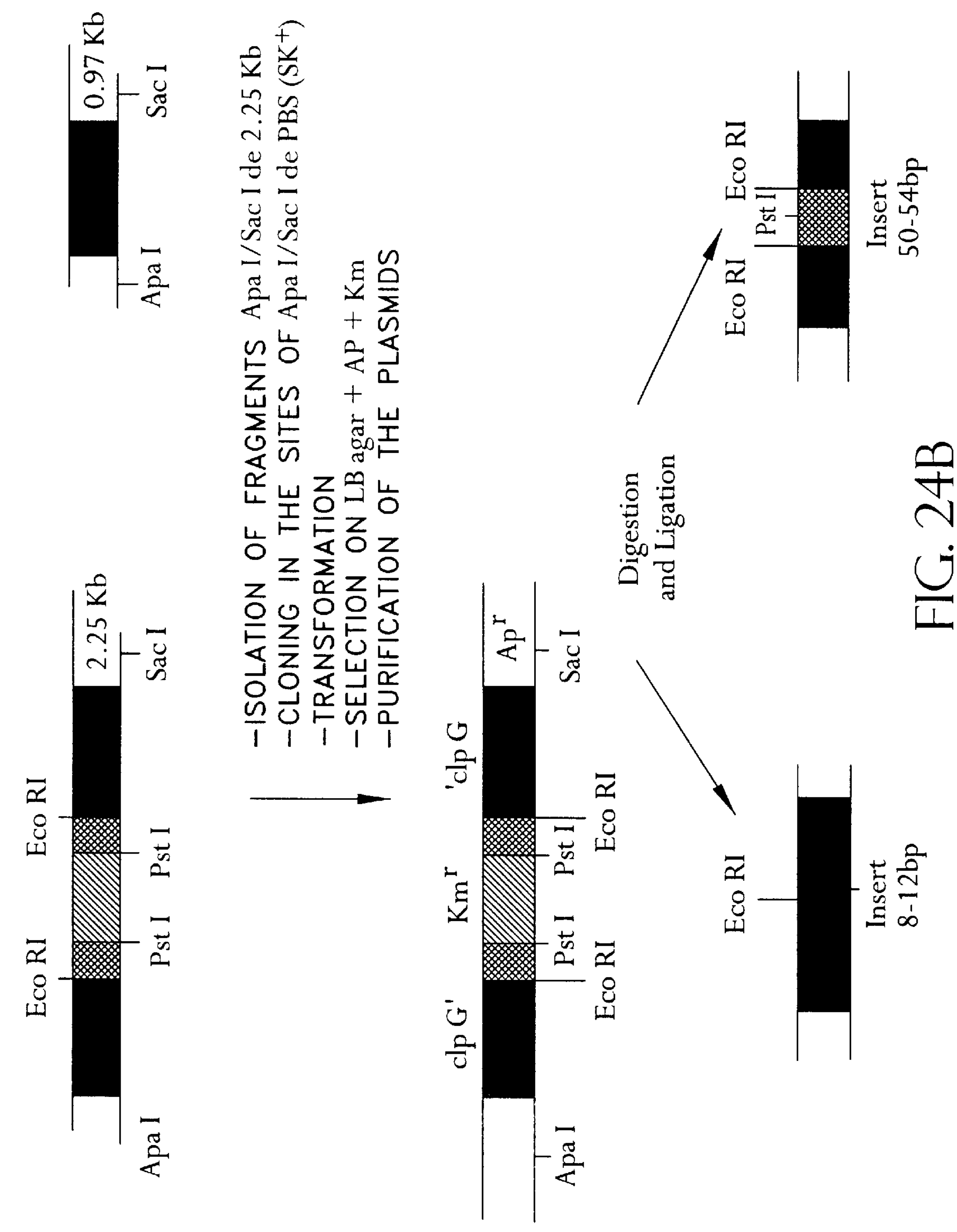

The $Km^r$ cassette used here, as shown in FIG. 23, along with its multiple and symmetrical restriction sites (MCS), is the EcoRI/EcoRI fragment that has 1.28 kilobases, as obtained from the pUC4K plasmid (as described by J. Viera and J. Messing, in *Gene,* Vol. 19 (1982), p. 259), and that contains the Tn 903 transposon. The 5' and 3' ends of the resistance gene include a polylinker that has the EcoRI site on the distal side of this gene, and the PstI site on the proximal side. The cloning of the $Km^r$ cassette at the single unique EcoRI site on the pDEV41155 plasmid, with the incorporation of an EcoRI linker, is shown in FIG. 24. The clones obtained after the transformation of the DH5α [*E. coli*] strain are selected on the basis of their dual resistance to kanamycin (which are the markers for the insertion sites) and to ampicillin (which is the marker for the vector plasmid). Accordingly, 830 $Ap^r$ $Km^r$ clones were isolated that contain the pDEV41155 plasmid that carries the $Km^r$ cassette. No mutated plasmids were found that had an insertion that affected either the activity of the beta lactamase or the replication of the plasmids. This selection favors the acquisition of mutations that have the $Km^r$ cassette in the clpG gene or in the rest of the vector.

To select the insertion points for the $Km^r$ cassette that are located solely within the clpG gene, the gene was excised and re-cloned in the same initial plasmid vector that had not been treated with Dnase I. For this purpose, the pDEV41155 plasmids that carry the $Km^r$ cassette were digested by both ApaI and SacI (as shown in FIG. 24). The ApaI and SacI sites are located 78 base pairs upstream and 893 base pairs downstream, respectively, from the ATG initiation codon of the clpG gene.

FIG. 24 indicates the procedure followed for the positive selection of the EcoRI linkers and of the EcoRI-PstI-EcoRI polylinker in the clpG gene.

The ApaI/SacI fragments that have 2.25 kilobases and that contain the clpG gene, as mutated by means of the insertion of the $Km^r$ cassette, are purified on agarose gels and cloned at the ApaI/SacI sites of the Bluescript SK vector. After transformation of the DH5α *E. coli* strain, 867 $Km^r$,$Ap^r$ clones were selected that had the $Km^r$ cassette in the clpG gene.

The presence of multiple and symmetrical restriction sites at the ends of the $Km^r$ cassette was used advantageously to introduce heterologous sequenes of different sizes into the clpG gene after excision of the cassette. This excision was accomplished starting with the plasmidic DNA extracted from the $Ap^r$ $Km^r$ clones by means of cutting with EcoRI or PstI. FIG. 24 illustrates two simple constructions that result in the excision of the $Km^r$ cassette by deletion. The recircularization of the DNA that had been linearized by EcoRI leads to the insertion of 8 to 12 base pairs, and the insertion of the DNA that had been linearized by PstI leads to the insertion of 50 to 54 base pairs.

In terms of the ClpG protein, this operation corresponds to the insertion of 3 or 4 amino acids, in the first case, and to the insertion of 17 to 18 amino acids, in the second case. After excision of the cassette, the recircularized plasmids are transferred to the DH5α *E. coli* strain that contains the pDSPH524 plasmid so that the expression of the mutated clpG genes can be tested.

FIG. 25 represents the nucleotide sequences resulting from the insertions of the EcoRI linkers (at the left of the figure) and of the EcoRI-PstI-EcoRI polylinker (at the right of the figure) into the clpG gene, and their corresponding peptide sequences. The three peptide sequences that correspond to the three possible reading frames for a given DNA sequence are deduced from each of the five EcoRI linkers utilized.

2) Expression of the Mutated clpG Genes

The permissivity of the ClpG protein was evaluated by means of an in vivo intergenic complementation test that made it possible to determine whether the clpG proteins, as modified by the various insertions of heterologic sequences consisting of from 3 to 18 amino acids, were still functional in terms of the biogenesis of the CS31A surface polymers.

A grand total of 5,895 clones were analyzed by means of in situ immunoblotting on colonies with a polyclonal antigen that was specified for native CS31A. Accordingly, 739 clones (i.e., 13.5 percent) were found to be positive for the production of CS31A. These results indicate that the ClpG proteins that have incorporated from 3 to 18 amino acids are being properly exported and integrated into the polymer structure of the CS31A, and that permissive regions exist within the ClpG protein.

3) Determination of the Location of Permissive Regions in the ClpG Protein

A mixture of recombinant plasmids extracted from the 739 clones that were positive for the biogenesis of the CS31A were subjected to a restriction analysis. The determination of the EcoRI site in the mutated clpG gene, in relation to other single and unique restriction sites (e.g., the XhoI and XbaI sites) existing on the vector plasmid on both sides of the clpG gene (as shown in FIG. 12) made it possible to position the insertions containing from 3 to 54 base pairs in this gene. In this way, various regions of the ClpG protein that tolerated the addition of from 3 to 18 additional amino acids could also be identified.

Figure 26:
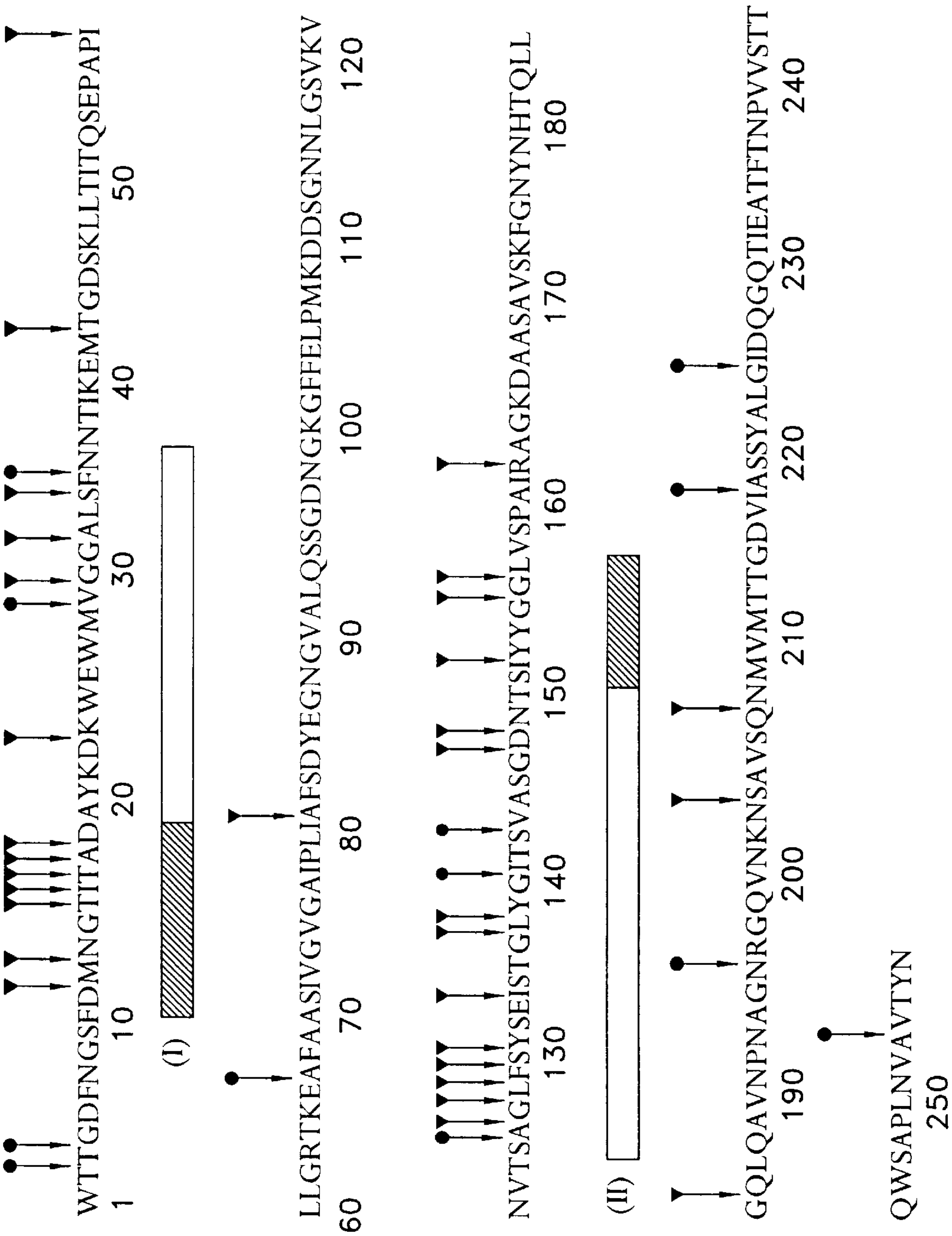
FIG. 26 shows the sequence for ClpG protein (SEQ ID NO:2) and location of insertion points for EcoRI linkers and EcoRI-PstI-EcoRI polylinkers.

A map was drawn up that indicated the permissive insertions. FIG. 26 shows the sequence for the ClpG protein and indicates the location of the insertion points for the EcoRI linkers (as solid dots) and the location of the insertion points for the EcoRI-PstI-EcoRI polylinkers (as solid diamonds). The vertical arrows indicate the approximate positions of the permissive insertions in the ClpG protein. The location of the permissive sites was determined on the basis of the restriction analysis. The regions (I) and (II) represented by rectangles indicate the two major permissive regions. The cross-hatched areas indicate the linear epitopes of the ClpG protein.

The results show that the 44 insertion points that were recorded are distributed along the entire length of the ClpG protein sequence. However, two primary regions, in which a large number of insertion points are located, appear to stand out. The first region, (I), which is located at the N-terminal end of the ClpG protein, between the amino acids at positions 11 and 36, contains 13 insertion points. The second region, (II), which is located in the central portion of the ClpG protein, between the amino acids at positions 125 and 156, contains 16 insertion points.

In conclusion, the results obtained demonstrate that it is possible to insert from 3 to 18 amino acids into the ClpG protein without affecting the biogenesis of the CS31A surface polymers.

V. General Conclusion Regarding the Potentially Permissive Zones of the CS31A Protein A synthesis of the results obtained in accordance with three complementary methods for identifying the zones on the surface of the molecule that are accessible and potentially permissive for heterologous insertions or replacements in the CS31A protein appears below.

Region A, as identified by random insertional mutagenesis, accepts the introduction of from 4 to 20 heterologous amino acids.

Region B, with its variable region VI and its antigenic immunogenic peptides in native form at positions 10–19 and positions 38–58, is permissive, because heterologous insertions were obtained through random mutagenesis, particularly in relation to the peptide at positions 10–19.

Region C, with its variable region V2, contains in its terminal portion an epitope (at positions 151–160) that is continuous but not antigenic in the native protein. However, several insertions were obtained through random mutagenesis, and therefore the permissivity of this region appears to be potentially worthwhile.

Region D, with its variable region V3, contains the only continuous antigenic and immunogenic epitope in the protein in native form—a condition which makes Region D a major immunodominant region. Several peptides in its C-terminal portion are immunogenic and antigenic in the denatured form of the protein. Finally, a few insertions were obtained by means of random mutagenesis.

G) Selection of Viral Epitopes

Five epitopes were selected for these examples. These epitopes consisted of the C and A epitopes of the S glycoprotein of the transmissive gastroenteritis (TGE) pork virus, an epitope of the VP6 protein of the bovine rotavirus, the C3 epitope of the VP1 capside protein of the Type 1 (Mahoney) polio virus, and an epitope of the VP1 capside protein of the aphthous fever virus (FMDV). The DNA fragments that code for these epitopes were obtained through chemical synthesis.

The codons that were selected were the ones that are most frequently used in the clpG gene. The ends of the DNA molecule that code for an epitope vary as a function of the location of the insertion, so that they will be compatible with the restriction sites introduced into the clpG gene.

FIG. 27 illustrates the oligonucleotide synthesis sequences utilized that code for the TGE, rotavirus, polio, and FMDV epitopes. The sequence of the epitope itself is indicated in boldface letters.

H) Cloning of the Dna Corresponding to the Viral Epitopes, and Expression of the Recombinant Proteins I. After Directed Mutagenesis The V2 region (from the amino acid at position 123 to the amino acid at position 150) and the V3 region (from the amino acid at position 183 to the amino acid at 221) were selected for the insertion of the epitopes in these examples. Single and unique restriction sites were created in the desired areas, by directed mutagenesis, using synthetic oligonucleotides that carried the selected mutation. The procedure used for this purpose involved partial single-strand DNA and the pMa 5-8 and pMc 5-8 vectors.

The HindIII-XbaI fragment of the pPSX83 [plasmid] was cloned in these vectors, resulting in the acquisition of the pMcHX and pMaHX plasmids. After mutagenesis, the HindIII-XbaI fragments obtained from the mutated pMcHX and from the mutated pMaHX were cloned again in pSELECT-1.

The presence of the desired mutations was confirmed by means of a restriction analysis and also through nucleotide sequencing in accordance with the Sanger method.

The expression of the recombinant proteins was verified by means of immunological tests on whole bacteria or on raw extracts at a temperature of 60° C. (i.e., by means of Immunodots and Western blots).

1) Changes Made in the V2 Region

The changes made in the V2 region are indicated in FIG. 28. In mutations 2 and 5, the amino acid at position 131 (i.e., tyrosine) was replaced by a threonine remainder. In mutation 6, the amino acids at positions 131 to 141 were deleted.

The mutated plasmids were introduced, by means of transformation, into a strain that contained pDSPH524, and the presence of CS31A was detected by means of immunological tests on extracts at a temperature of 60° C. after electrophoresis on a denaturing polyacrylamide gel (i.e., a Western blot).

Mutations 1 through 5 produced CS31A in quantities comparable to those produced by the control strain that contained pPSX83+pDSPH524.

Figure 29:
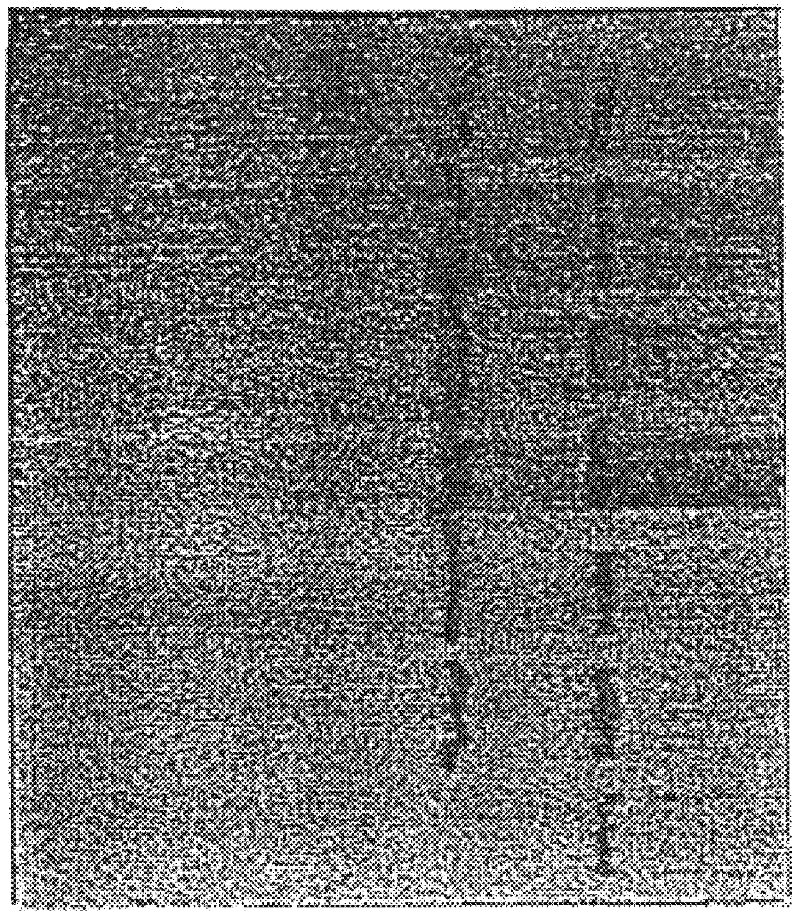
FIG. 29 shows mutation 6.

As shown in FIG. 29, mutation 6 did not produce any CS31A.

a) Introduction of the Epitopes and Expression of the Recombinant Proteins

Figure 30A:
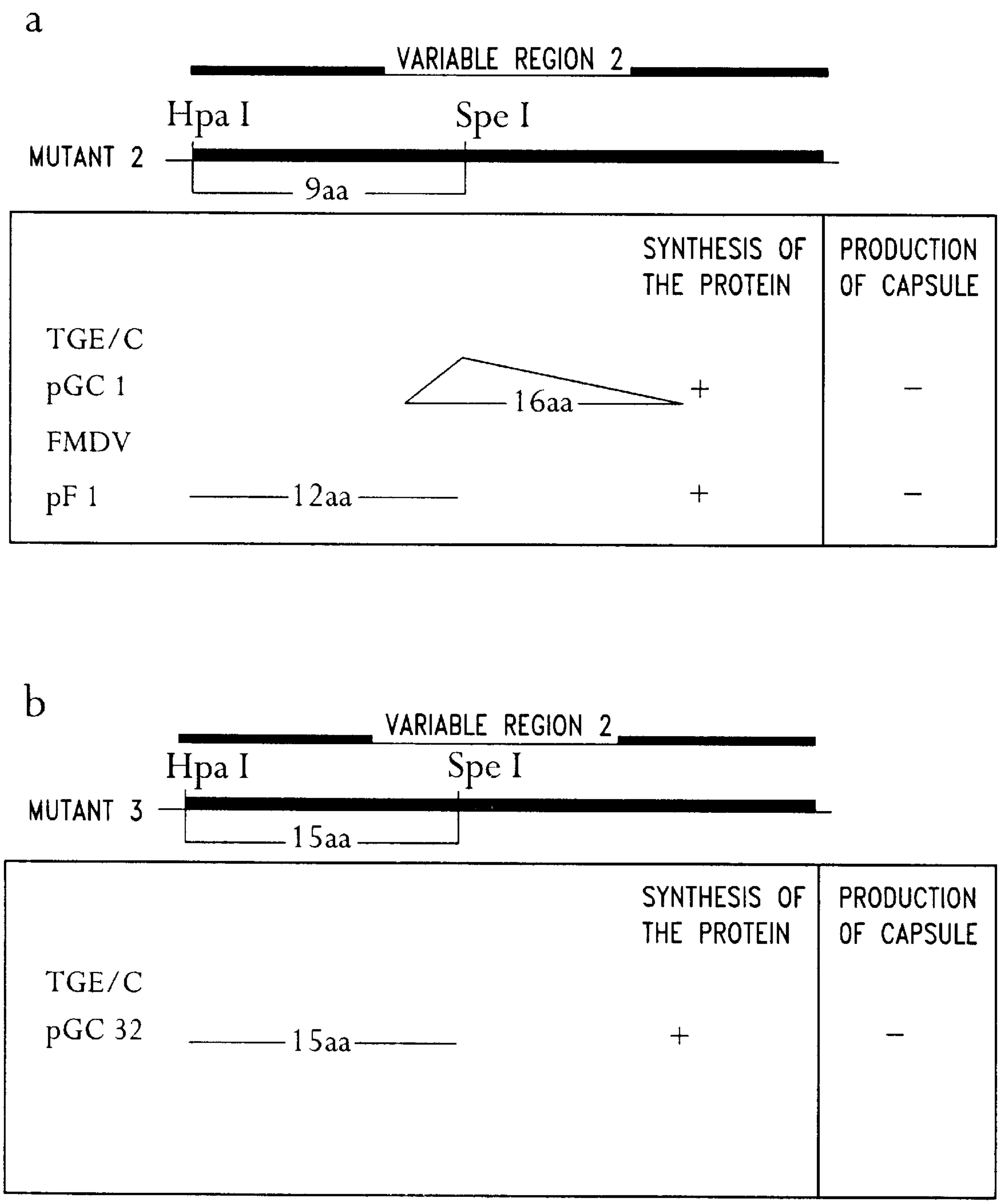
FIG. 30 shows the synthesis (+) or non-synthesis (−) of protein, and production (+) or non-production (−) of CS31A capsule for each mutation.
Figure 30B:
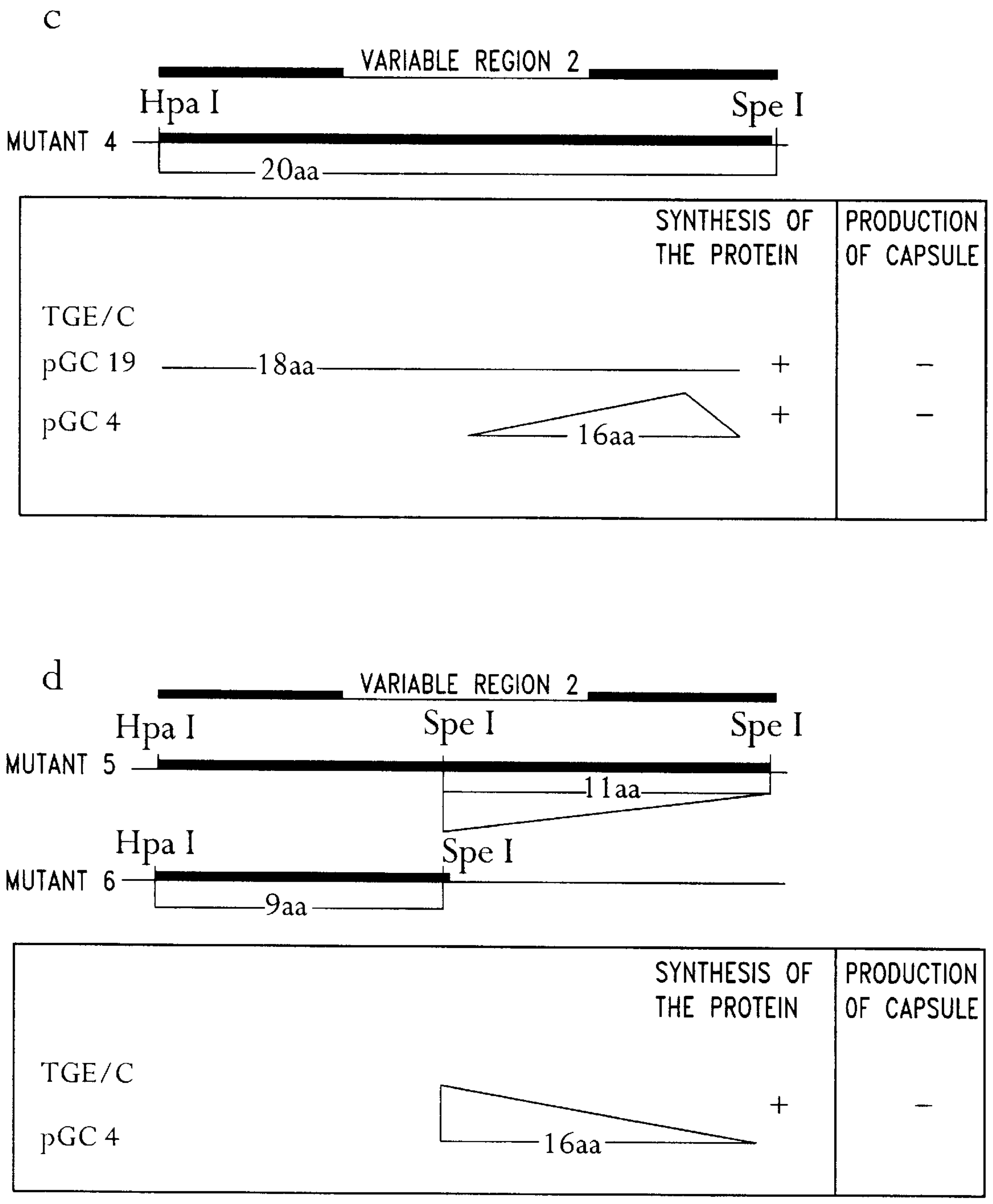

A synthetic DNA that codes for the TGE epitope has ends that are compatible with the HpaI/SpeI restriction sites (as indicated in FIG. 27*d*). This DNA replaced the HpaI and SpeI fragment of the clpG gene in mutations 3 and 4, generating the pGC32 and pGC19 plasmids, respectively (as indicated in FIGS. 30*b* and 30*c*).

A synthetic DNA that codes for the TGE epitope has two ends that are compatible with SpeI restriction sites (as indicated in FIG. 27*d*). This DNA was inserted in phase at the SpeI site on the clpG gene of mutations 2 and 4, thereby generating the pGC1 and pGC4 plasmids (as indicated in FIGS. 30*a* and 30*c*). It also replaced the SpeI/SpeI fragment in mutation 5, thereby generating the pGC44 plasmid (as indicated in FIG. 30*d*).

A synthetic DNA that codes for the FMDV epitope has ends that are compatible with the HpaI/SpeI restriction sites. This DNA replaced the HpaI/SpeI restriction fragment of the clpG gene in mutation 2, generating the pF1 plasmid (as indicated in FIG. 30*a*).

FIG. 30 indicates, for each of the mutations, the synthesis (+) or non-synthesis (−) of the protein, and the production (+) or non-production (−) of the CS31A capsule.

The pGC32, pGC19, pGC44, pGC1, pGC4, and pF1 plasmids are introduced individually into the complementation strain. Western blot tests were performed, at a temperature of 60° C., on extracts obtained from these strains. The polyclonal antibodies against CS31A or the G150 antipeptide decribed earlier do not recognize a polypeptide that has the expected molecular weight, but does recognize polypeptides that have a higher molecular weight, i.e., that weigh approximately 50 kDa. In these Immunodot experiments, the whole bacteria were negative for CS31A. Therefore, the ClpG sub-unit is synthesized but not exported and polymerized at the surface of the bacterium. In all likelihood, the ClpG sub-unit is blocked in the periplasm in association with another protein that has not yet been identified.

Figure 31:
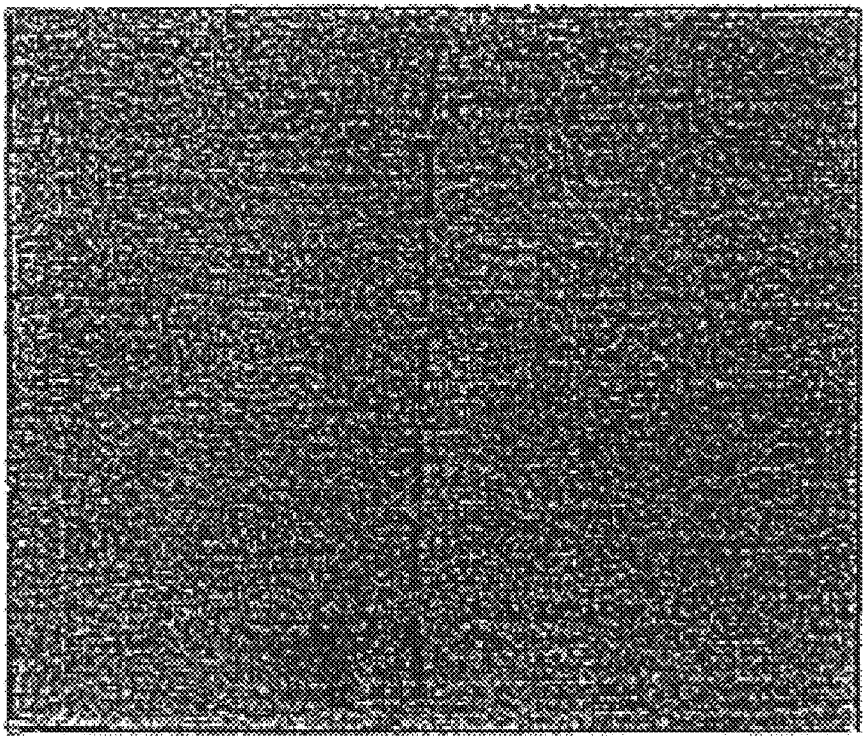
FIG. 31 is a photograph of a Western blot taken from bacteria that contain mutations 1–6 (+pDSPH524) and from the polyclonyl antibody against CS31A.

FIG. 31 is a photograph of a Western blot, as obtained at a temperature of 60° C. from extracts (concentrated 10 times) taken from bacteria that contain mutations 1 through 6 (+pDSPH524) and from the polyclonal antibody against CS31A.

This result is not incompatible with the use of such recombinant bacteria in vaccines.

b) Conclusions Regarding the V2 Region

Figure 32:
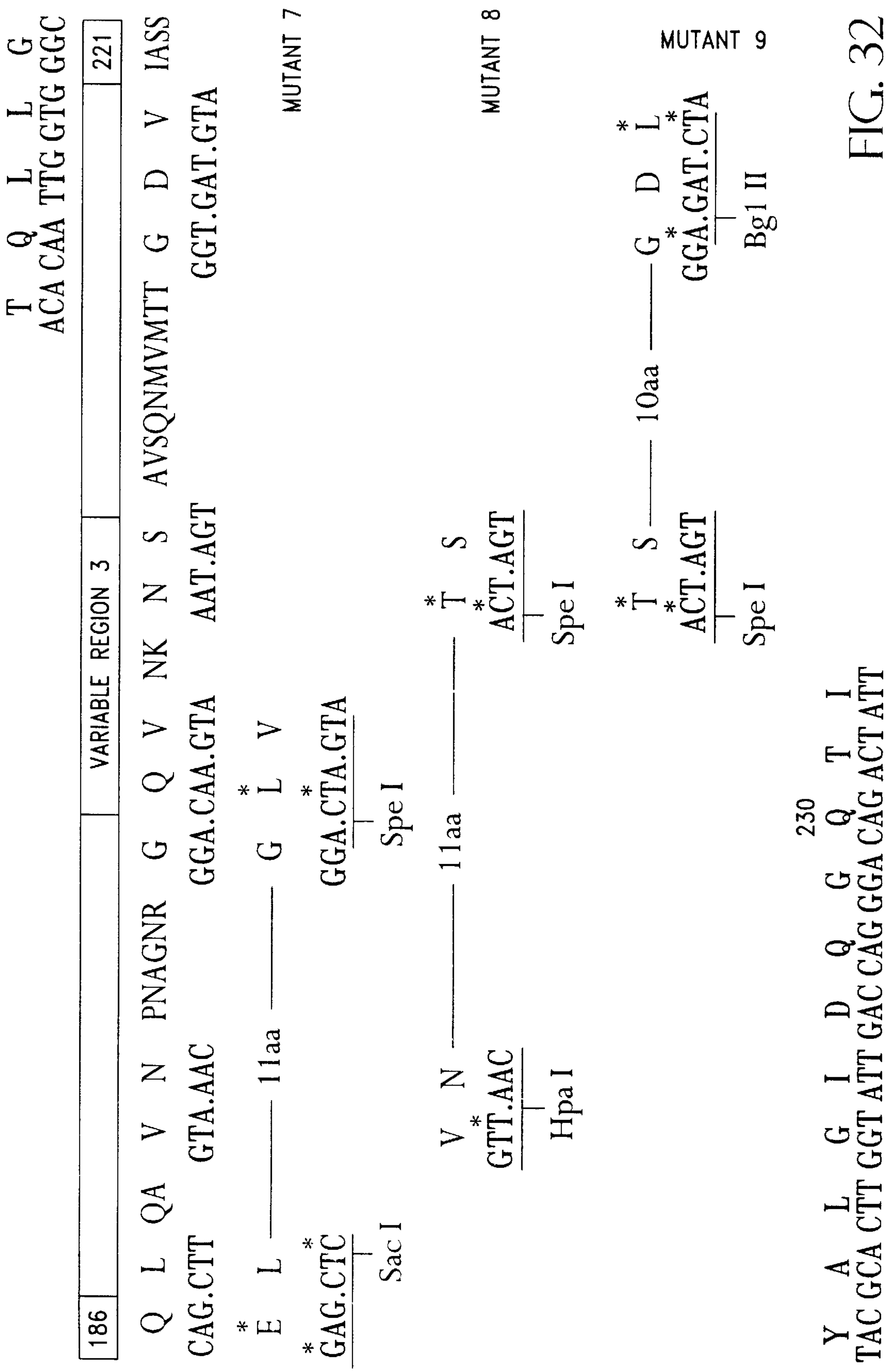
FIG. 32 shows changes in region V3 (SEQ ID NO:1 and SEQ ID NO:2).

According to the results of random mutagenesis experiments, the V2 region appears to be permissive overall. However, certain amino acids should be important, inasmuch as the introduction (in the form of insertions and substitutions) of nucleotide sequences that code for various epitopes does disturb the biogenesis of the CS31A. Therefore, it will be necessary to determine more specifically the exact location of the permissive sites in this zone 2) Changes Made in the V3 Region The changes made in the V3 region are indicated in FIG. 32. In this figure, the nucleotides and the amino acids marked with an asterisk are the ones that were modified by mutagenesis.

In mutation 7, the glutamine remainder at position 186 was replaced by a glutamate remainder. In this way an SacI restriction site was created. Furthermore, a glutamine remainder at position 199 was replaced by a leucine remainder. In this way an SpeI restriction site was created.

In mutation 8, an HpaI restriction site was created in conjunction with the valine codon at position 190. An asparagine remainder at position 203 was replaced by a threonine remainder, thereby creating an SpeI restriction site.

In mutations 9 and 10, an asparagine remainder at position 203 was replaced by a threonine remainder, thereby creating an SpeI restriction site. Furthermore, in mutation 9, a valine remainder at position 217 was replaced by a leucine remainder. In this way a BglII restriction site was created.

The mutated plasmids were introduced, by means of transformation, into a strain that contained pDSPH524, and the presence of CS31A was detected through immunological tests on whole bacteria and on extracts at a temperature of 60° C. after electrophoresis on a denaturing polyacrylamide gel. Mutations 8, 9, and 10 produced CS31A in a quantity comparable to the quantity produced by the control strain that contained pPSX83+pDSPH524. Mutation 7 produced slightly less CS31A.

shown in FIG. 27), replaced the HpaI/SpeI fragment in mutation 8, thereby generating the pP688, pGP684, and pF681 plasmids (as shown in FIG. 34*a*).

The bacteria that contain the pP688+pDSPH524 or pF681+pDSPH524 plasmids are very weakly recognized by the polyclonal antibodies against CS31A. Similarly, in the Western blot, the recombinant sub-units are also recognized more weakly than the control sub-unit. On the contrary, however, the bacteria that contain the pGP684+pDSPH524 plasmids are strongly recognized by the polyclonal antibodies against CS31A and by the monoclonal antibody directed against the C epitope of the TGE virus.

In mutation 10

A synthetic DNA fragment whose ends are compatible with the SpeI restriction site, that codes for the C epitope of the TGE virus (S D S S F F S Y G E I P) SEQ ID NO:33, and that has the following sequence:

```
      Xho1                                        SEQ ID NO: 35
CT  ACG GAC TCG AGC TTC TTT TCG TAC GGT GAG ATT CCT AGT
 T   S   D   S   S   F   F   S   Y   G   E   I   P   S
```

Figure 33:
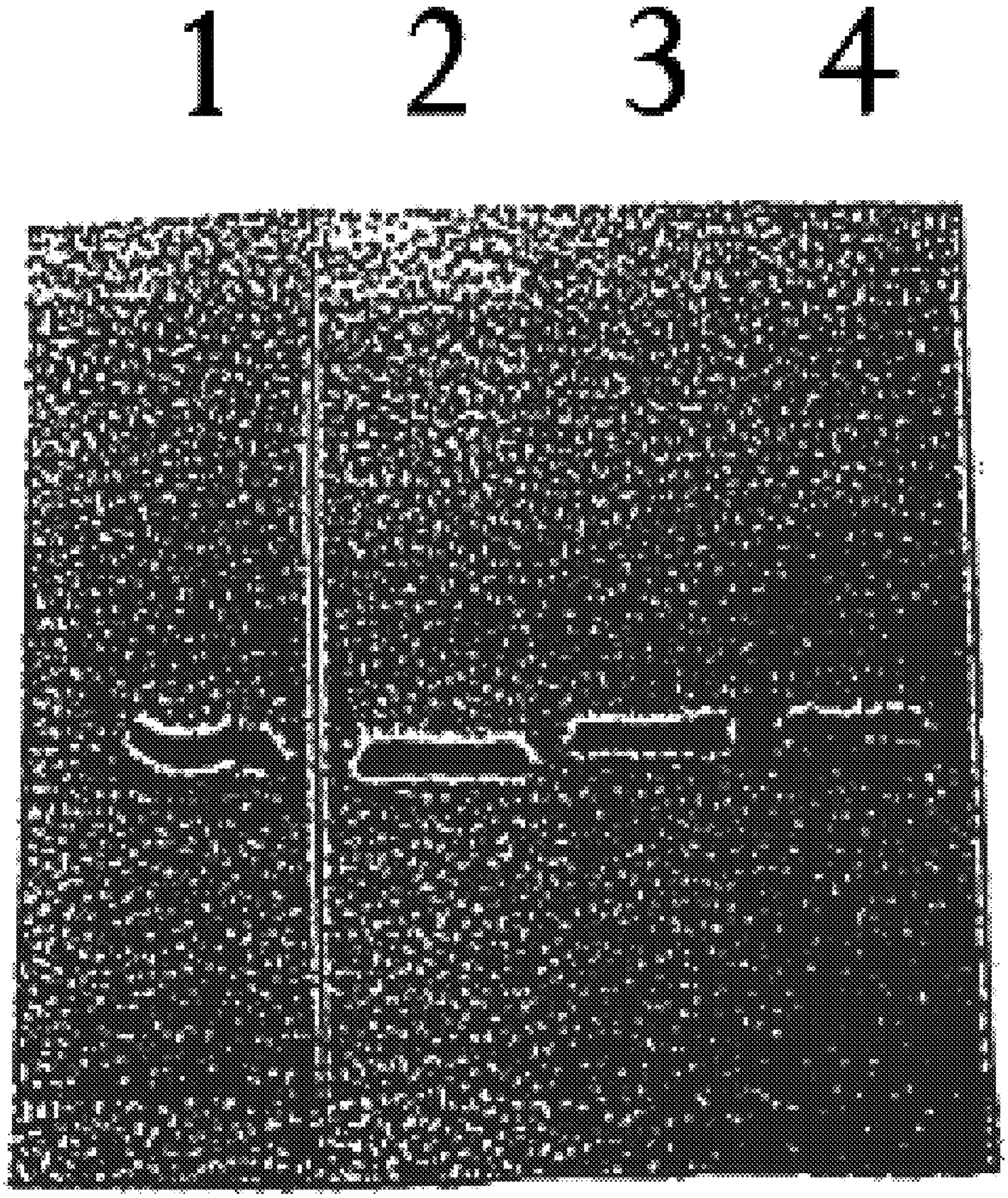
FIG. 33 is a photograph of a Western blot taken from the polyclonyl antibody against CS31A.

FIG. 33 is a photograph of a Western blot, as obtained at a temperature of 60° C. from extracts (concentrated 10 times) and from the polyclonal antibody against CS31A. In this figure, Part 1 corresponds to pPSX83+pDSPH524; Part 2 corresponds to mutation 9+pDSPH524; Part 3 corresponds to mutation 8+pDSPH524; and Part 4 corresponds to mutation 7+pDSPH524.

a) Introduction of Epitopes and Expression of Recombinant Proteins

In mutation 9

Five synthetic DNA fragments, two of which code for the C epitope of the TGE virus, one of which codes for the A epitope of the TGE virus, one of which codes for the epitope of the rotavirus, and the last of which codes for the polio epitope, and [all of] which have cohesive SpeI and BglII ends (as shown in FIG. 27), replaced the SpeI/BglII fragment in mutation 9, thereby generating the pGG103, pGP 105, pGA102, pR104, and pP101 plasmids (as shown in FIG. 34*b*).

FIG. 34 indicates the synthesis (+) or non-synthesis (−) of the protein, and the production (+) or non-production (−) of the CS31A capsule.

Figure 35A:
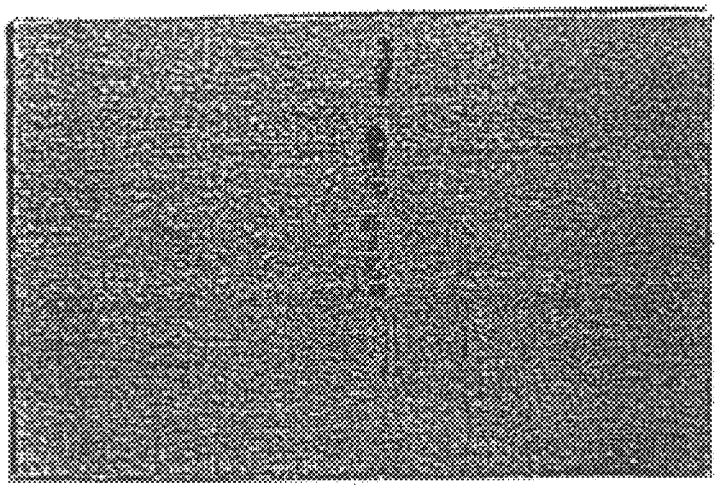
FIG. 35 is a photograph of a Western blot taken from bacteria that contain certain constructions created in the V3 region and from the polyclonyl antibody against CS31A.
Figure 35B:
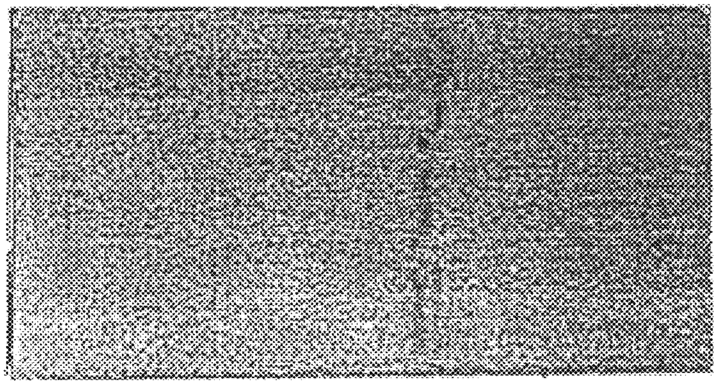

Whether in the form of a Western blot or in the form of a dot-blot, the recombinant CS31A/epitope sub-units are very well recognized by the anti-CS31A polyclonal antibodies, although to a somewhat lesser extent for the pGA102 and pR104 plasmids. Furthermore, the hybrid sub-unit coded by pGA102 has a lower molecular weight than the wild sub-unit. FIG. 35 is a photograph of a Western blot, as obtained at a temperature of 60° C. from extracts (concentrated 10 times) from bacteria that contain certain constructions created in the V3 region and from the polyclonal antibody against CS31A.

The whole bacteria the contain the pGG103 or pGP 105+pDSPH524 plasmids are recognized by a monoclonal antibody directed against the C epitope of the TGE virus.

In mutation 8

Three synthetic DNA fragments, one of which codes for the polio epitope, the second of which codes for the C epitope of the TrE virus, and the third of which codes for the FMDV epitope, and [all of] which have ends that are compatible with the HpaI and SpeI restriction sites (as is inserted at the SpeI site of mutation 10, thereby generating the paC326 plasmid.

This synthetic DNA includes a single and unique Xho1 site, located on the5' side. Under Western immunoblotting, the recombinant sub-unit expressed by the bacteria that contain the pGC326+pDSPH524 plasmids is strongly recognized by the polyclonal antibodies against CS31A and by the monoclonal antibody directed against the C epitope of the TGE virus. The hybrid sub-unit coded by the pGC326 hybrid has a higher molecular weight than the wild sub-unit, due to the addition of the twelve amino acids that make up the C epitope.

c) Conclusions Regarding the V3 Region

The results obtained agree well with the results of the immunostructural studies. This region appears to be very permissive, in that 5 different epitopes were introduced at two different sites in the V3 region, in all cases leading to the production of CS31A, although somewhat more weakly in mutation 8 for the polio and FMDV epitopes and in mutation 9 for the A epitope of the TGE virus and the epitope of the rotavirus.

Furthermore, this region is located outside the molecule, because the C epitopes of the TGE virus are recognized on the recombinant bacteria by the corresponding monoclonal antibodies. Consequently, this very tolerant region appears to be a region of choice for the insertion of foreign polypeptides that are intended to be present on the outside of the molecule. Accordingly, foreign sequences can be introduced either by substitution, starting with mutations 7, 8, and 9, or else by means of additive insertion, starting with mutation 10.

3) Changes Made in Region D

Starting with mutations 7, 8, and 9 (as indicated in FIG. 32), substitutions were made between the V3 region (delimited in FIG. 9 by the amino acids located at positions 186 and 221), and the C-terminal amino acid (represented in FIG. 9 by the asparagine located at position 257) in the ClpG sub-unit.

a) In Mutation 7

The DNA that corresponds to the recombinant plasmid of mutation 7, which contains a single unique SpeI site in the V3 region (as shown in FIG. 32) and a single unique XbaI site in the polylinker of the pSELECT1 vector, has been restricted by SpeI and XbaI. Because of the compatibility of the ends generated by SpeI and XbaI, the plasmid restricted in this way could be recircularized by the T4 DNA ligase in order to yield the pDSX28 plasmid. This operation made it possible to eliminate the last 59 C-terminal amino acids in the ClpG sub-unit located, in FIG. 9, between the amino acids in positions 198 and 257, and to fuse with the ClpG protein a foreign sequence consisting of 100 amino acids coded by a portion of the DNA of the vector in phase with the rest of the unmodified clpG gene.

The results obtained through the use of Western immunoblotting with the anti-CS31A polyclonal antibodies indicate that the bacteria that contain the pDSPH524+pDSX28 plasmids still express the CS31A capsule, albeit weakly.

b) In Mutation 8

The DNA that corresponds to the recombinant plasmid in mutation 8, which contains a single unique HpaI site in the V3 region (as shown in FIG. 32) and a single unique SmaI site in the polylinker of the pSELECT1 vector, has been restricted by HpaI and SmaI. Because of the free ends generated by HpaI and SmaI, the plasmid restricted in this way could be recircularized by the T4 DNA ligase in order to yield the pDS68 plasmid. This manipulation led to the elimination of the last 67 C-terminal amino acids in the ClpG sub-unit located, in FIG. 9, between the amino acids in positions 199 and 257, and to the introduction, by means of genetic fusion, of a foreign sequence consisting of 84 amino acids coded by a portion of the DNA of the vector in phase with the rest of the unmodified clpG gene.

The results obtained through the use of Western immunoblotting with the anti-CS31A polyclonal antibodies indicate that the bacteria that contain the pDSPH524+pDS68 plasmids still express the CS31A capsule, albeit weakly.

c) In Mutation 9

The DNA that corresponds to the recombinant plasmid of mutation 9, which contains a single unique BglII site in the V3 region (as shown in FIG. 32) and a single unique BamHI site in the polylinker of the pSELECT vector, has been restricted by BglII and BamHI. Because of the compatibility of the ends generated by BglII and BamHI, the plasmid restricted in this way could be recircularized by the T4 DNA ligase in order to yield the pDBB10 plasmid. This recircularization had the effect of eliminating the last 41 C-terminal amino acids in the ClpG sub-unit located, in FIG. 9, between the amino acids in positions 216 and 257, and of introducing, by means of genetic fusion, of a foreign sequence consisting of 84 amino acids coded by a portion of the DNA of the vector in phase with the rest of the unmodified clpG gene.

The results obtained through the use of Western immunoblotting with the anti-CS31A polyclonal antibodies indicate a very good degree of reactivity on the part of the bacteria that contain the pDSPH524+pDBB10 plasmids.

II. After Random Insertional Mutagenesis

1) Principle

The random insertional mutagenesis procedure that has made it possible to detect the permissive regions in the ClpG protein was used advantageously in connection with the insertion of the C epitope of the transmissible pork gastroenteritis virus. This continuous epitope is a major antigenic site for the external E2 glycoprotein, which is the best candidate as a potential protective antigen, because it is capable of inducing neutralizing antibodies and of stimulating immunity to cell mediation.

A synthetic oligonucleotide that corresponds to the nucleotide sequence that codes for the C epitope is inserted at the EcoRI site, which was located beforehand in the permissive sites on the clpG gene by means of the random insertion of an EcoRI linker. The mutated clones in the clpG gene that has incorporated the oligonucleotide are analyzed by means of immunoblotting with the aid of a polyclonal antibody that is specific for the ClpG protein and a monoclonal antibody that is specific for the C epitope of the transmissible gastroenteritis coronavirus.

2) Procedure a) Insertion of the C Epitope of the Transmissible Gastroenteritis (TGE) Virus A double-stranded non-phosphorylated oligonucleotide was synthesized that codes for the C epitope of the TGE virus (i.e., the amino acids located at positions 361 to 372), that has the sequence SDSSFFSYGEIP SEQ ID NO:33, and that includes an EcoRI site at the 5' and 3' ends. This oligonucleotide contains a BspEI restriction site (BspMII, AccIII, Kpn 21, MroI) (5'-TCC GGA-3') that facilitates the selection of the recombinant agents that include the C epitope.

Figure 36:
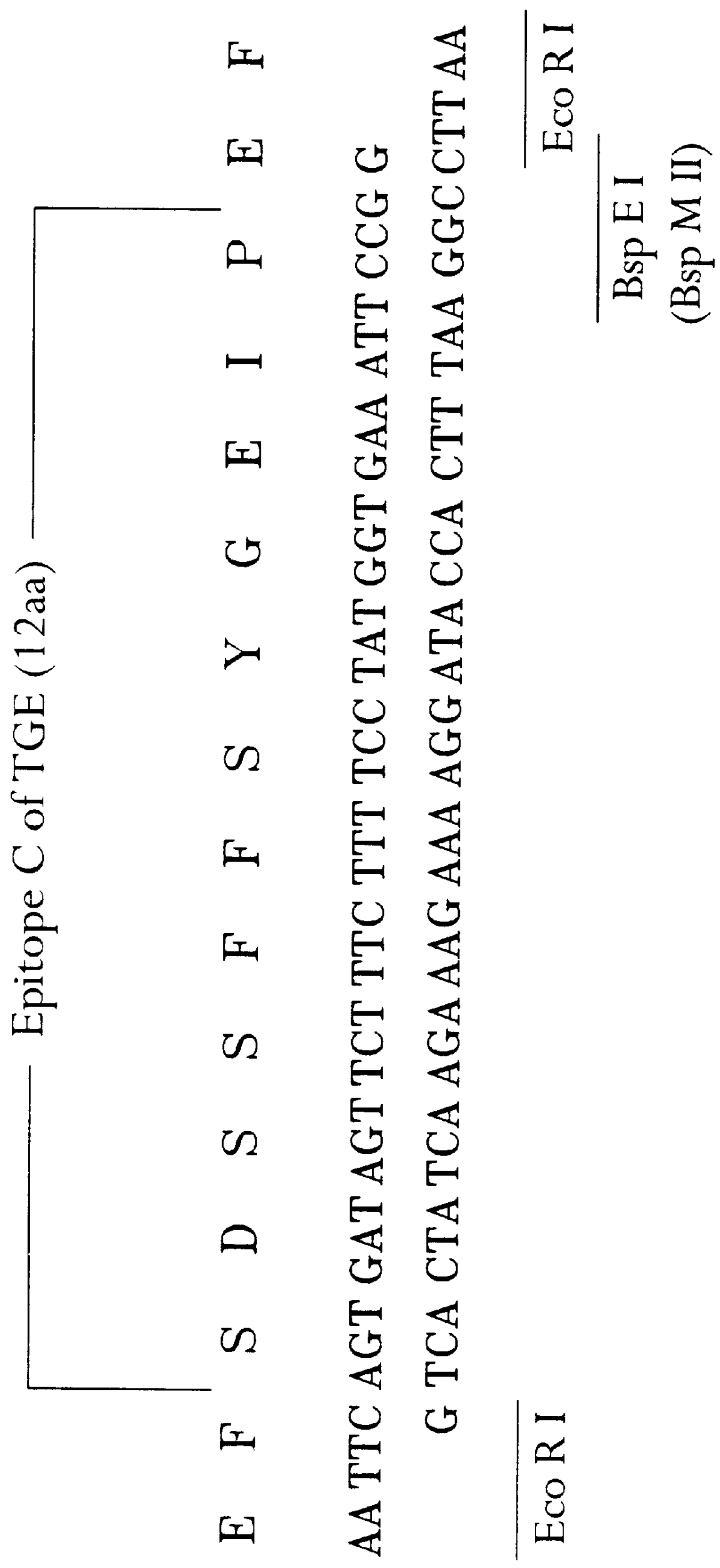
FIG. 36 shows the oligonucleotide (SEQ ID NO:109 and SEQ ID NO:111) and peptide (SEQ ID NO:110) sequences that correspond to the C epitope introduced into the EcoRI linker.

The oligonucleotide and peptide sequences that correspond to the C epitope introduced into the EcoRI linker are shown in FIG. 36.

The selection of the codons was based on the frequency of the codons preferentially used in the clpG gene. The non-phosphorylated double-stranded oligonucleotide at 5' was placed in the presence of the T4 DNA ligase and of a mixture of pDEV41155 DNA that had been linearized beforehand by EcoRI, whose site is present in various permissive regions of the clpG gene. After transformation of the DH5α *E. coli*, the transformation mixture was placed directly in a fluid LB culture medium with ampicillin. The total plasmidic DNA extracted from this culture was restricted by BspEI. A mixture of linear DNA was recovered and purified from an agarose gel. This stage made it possible to isolate uniquely the plasmid DNA that had inserted the oligonucleotide that corresponds to the C epitope. This DNA was recircularized by ligation and transferred to the Dh5α *E. coli* strain that contained the pDSPH524 plasmid in order to test, through intergenic complementation, for the presence of the C epitope in the CS31A surface polymers.

b) Immunoreactivity of the Hybrid ClpG/C Epitope Proteins

A total of 1,000 clones that incorporated the C epitope of the TGE virus were obtained and analyzed for the production of CS31A surface polymers and for the antigenicity of the C epitope. The clones that synthesize the CS31A protein on the surface of the mutated bacteria were detected by means of an in situ immunodetection test on colonies through the use of a native anti-CS31A serum. In this way, 492 mutant clones (i.e., 49 percent) were shown to be positive for the production of CS31A, thereby suggesting that the hybrid ClpG/C epitopes are integrated into the final structure of the CS31A. To examine the antigenicity of the C epitope, these 492 CS31A clones were tested by means of in situ immunoblotting on colonies with the Mab 3b.5 monoclonal antibodies that are specific for the C epitope of the TGE virus, as described by B. Delmas et al. in *J. Gen. Virol.,* Vol. 71 (1990), p. 1313.

Figure 37A:
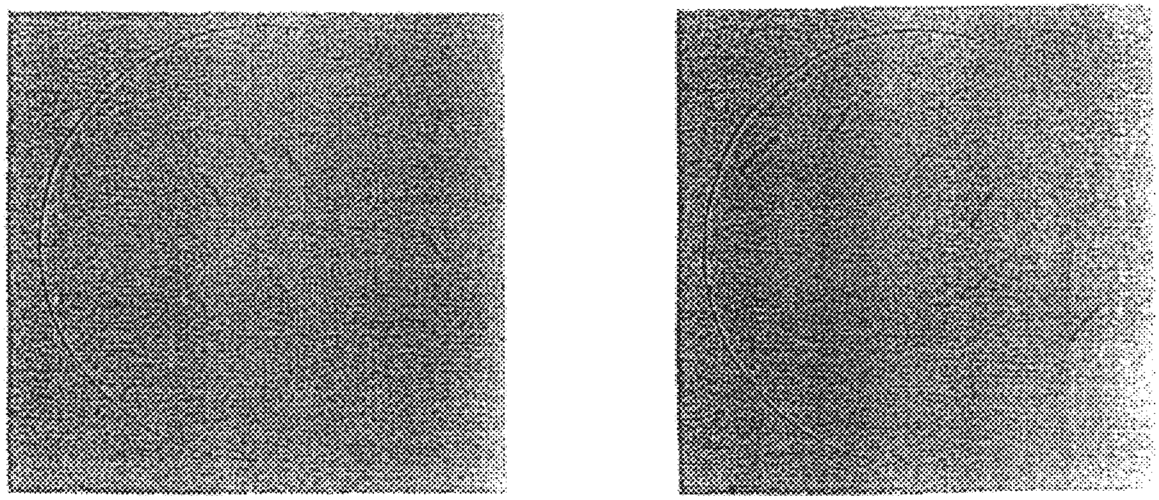
FIG. 37 shows the immunoreactivity of modified ClpG proteins at various locations.
Figure 37B:
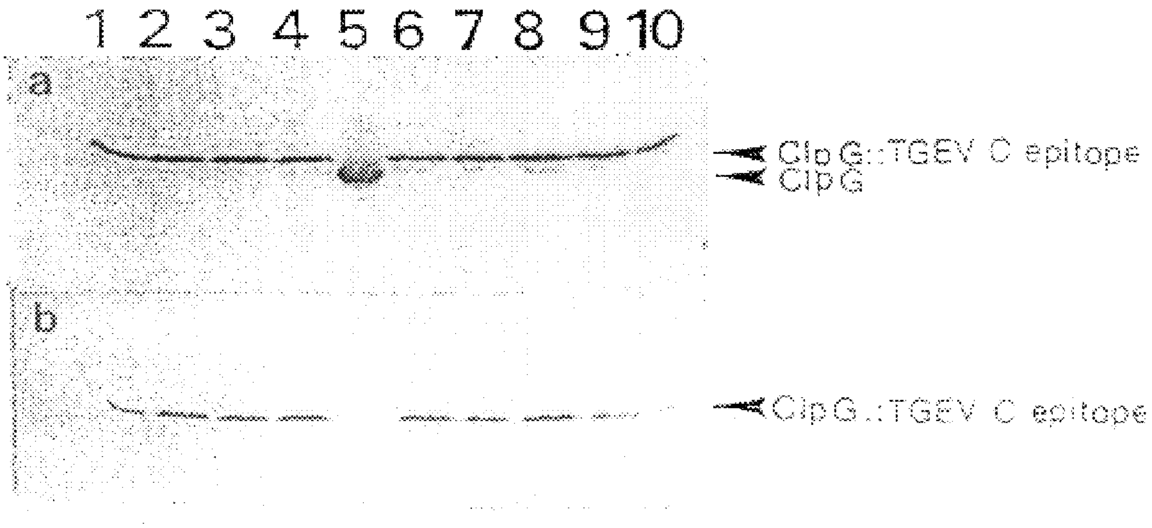

FIG. 37(A) and FIG. 37(B) indicate the immunoreactivity of the modified ClpG proteins at the various locations listed below:

- FIG. 37(A): Immunoreactivity with the Mab 3b.5 monoclonal antibody that is specific for the C epitope of the TGE virus (as described by B. Delmas et al. in *J. Gen. Virol.,* Vol. 71 (1990), p. 1313) by means of in situ immunoblotting on colonies.
- FIG. 37(B): Western blotting with an anti-ClpG serum (panel a) and with the Mab 3b.5 monoclonal antibody (panel b) that is specific for the modified ClpG proteins (channels 1–4 and 6–10) and the unmodified ClpG proteins (channel 5) under denaturing conditions.

FIG. 37A shows that only 11 colonies (i.e., 1 percent) react with the Mab 3b.5 antibody. The immunoreactivity of these hybrid proteins with the Mab 3b.5 antibody and with the native anti-CS31A polyclonal antibodies was confirmed by Western blotting under denaturing conditions (as shown in FIG. 37B) and also under non-denaturing conditions. Under denaturing conditions (i.e., SDS-PAGE at a temperature of 100° C. for 5 minutes), all 11 of the clones (although only 9 are shown in FIG. 37B) reacted with both types of antibodies and displayed a weaker electrophoretic migration than the wild ClpG protein, because of the presence of the 16 supplementary amino acids that correspond to the C epitope. Under non-denaturing conditions (i.e., PAGE without SDS and without heating to 100° C. for 5 minutes), the electrophoretic profiles indicate an oligomeric structure for the hybrid ClpG proteins which is similar to that of the wild ClpG protein.

c) Determination of the Location of the C Epitope in the Hybrid ClpG Protein

The location of the C epitope in the hybrid ClpG protein was determined by sequencing. The results indicate that among the 11 mutant clones, the C epitope is inserted exactly between the signal peptide and the mature peptide in the ClpG pre-protein.

Figure 38:
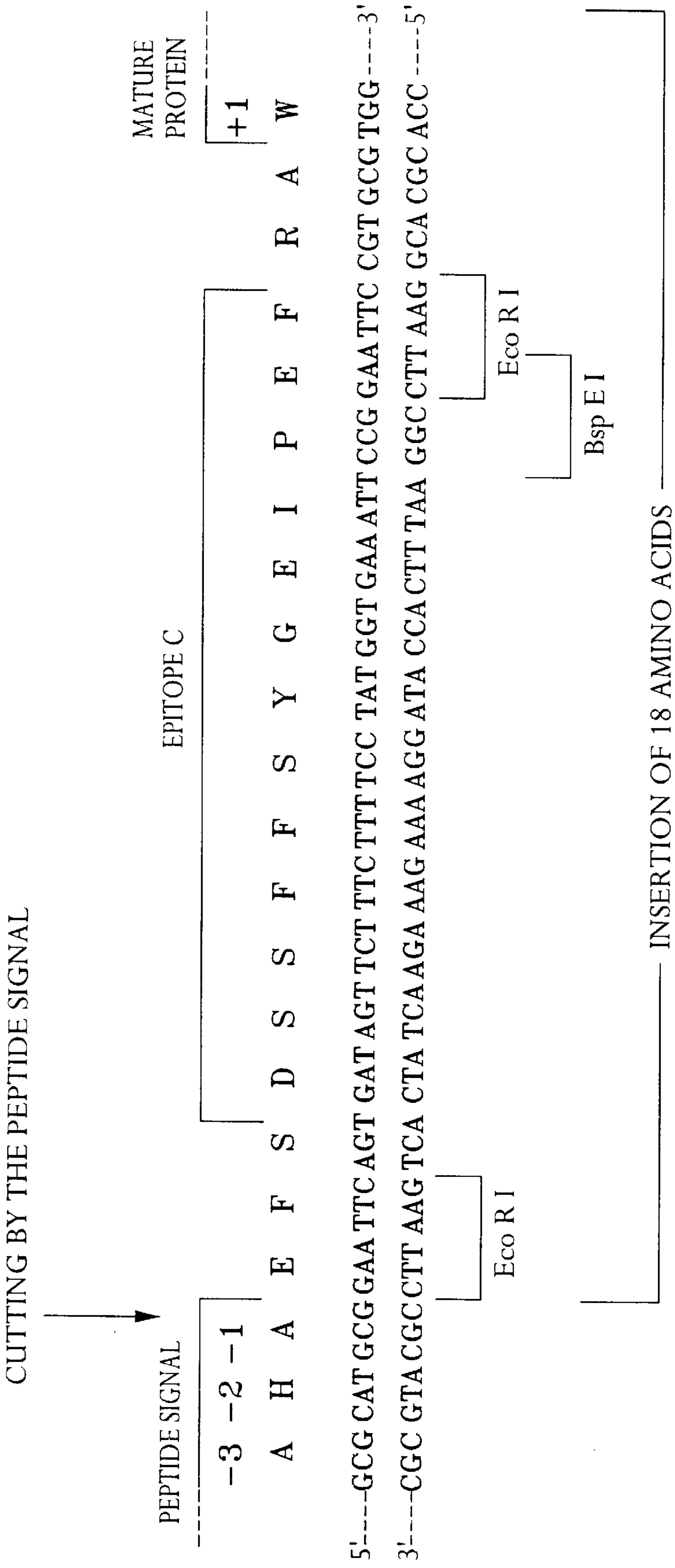
FIG. 38 shows the sequence of oligonucleotide (SEQ ID NO: 112) and (SEQ ID NO:113) that codes for the C epitope of the TGE virus.

FIG. 38 shows the sequence for the oligonucleotide that codes for the C epitope of the TGE virus, as introduced between the signal peptide and the mature peptide in the ClpG pre-protein.

The sequencing-based analysis of the plasmid DNA of several mutant clones that express the CS31A protein but not the C epitope of the TGE virus indicates that the synthetic DNA that codes for this epitope was inserted in an improper orientation inside the clpG signal sequence located, in FIG. 9, between the amino acids located at positions −21 and −1 in the CS31A protein (see FIG. 14). Four heterologous insertion sequences were obtained. (The additional heterologous sequences are underlined):

The first insertion sequence is located between the amino acids located at positions −13 and −12 in FIG. 9:

```
-21      -13                       -12  SEQ ID NO: 36
MKKTLIALA GIPEFHHRKRKNYHOIPALA VAVSAV
```

The second insertion sequence is located between the amino acids located at positions −7 and +8 in FIG. 9:

```
-21                   -                 SEQ ID NO: 37
7                          +8
MKKTLIALAVAVSAV EFRNFTIGHERTITEFRA GS-
FDM
```

The third insertion sequence is located between the amino acids located at positions −6 and +1 in FIG. 9:

```
                                        SEQ ID NO: 38
-21                   -1                 +1
MKKTLIALAVAVSAVGAAAHA EFRNFTIGHERTITEFRA W
```

The fourth insertion sequence is located between the amino acids located at positions −6 and −1 in FIG. 9:

```
                                        SEQ ID NO: 39
-21                -1                  +1
MKKTLIALAVAVSAVS RNSGISPOEKKELSINSG AW
```

Because the reading frame was respected, it is easy to understand why the CS31A capsule, unlike the C epitope, is always expressed. This indicates that the ClpG signal sequence may be a permissive region and that several cutting sites may exist, thanks to the signal peptidase located within the ClpG signal sequence.

This work shows that it is possible to insert a heterologous peptide with 20 amino acids into the ClpG pre-protein as well as in the mature protein without disturbing the biogenesis of the CS31A, and consequently that the heterologous peptide is antigenic toward the native protein.

Figure 39A:
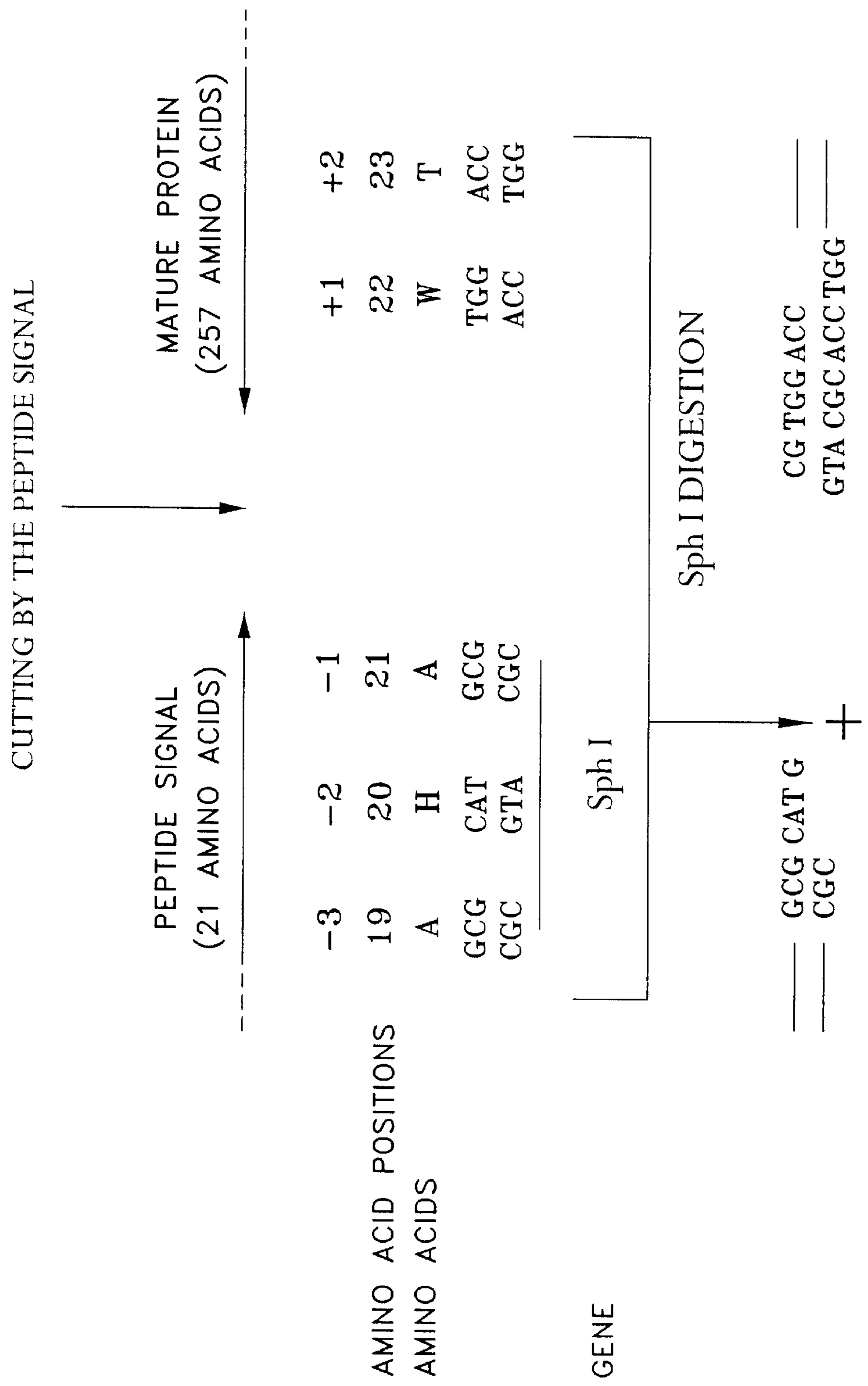
FIG. 39 shows the insertion plan (SEQ ID NO:115 and SEQ ID NO:114) for the C epitope of the TGE virus between the signal peptide and the mature protein of the ClpG pre-protein (SEQ ID NO:1).
Figure 39B:
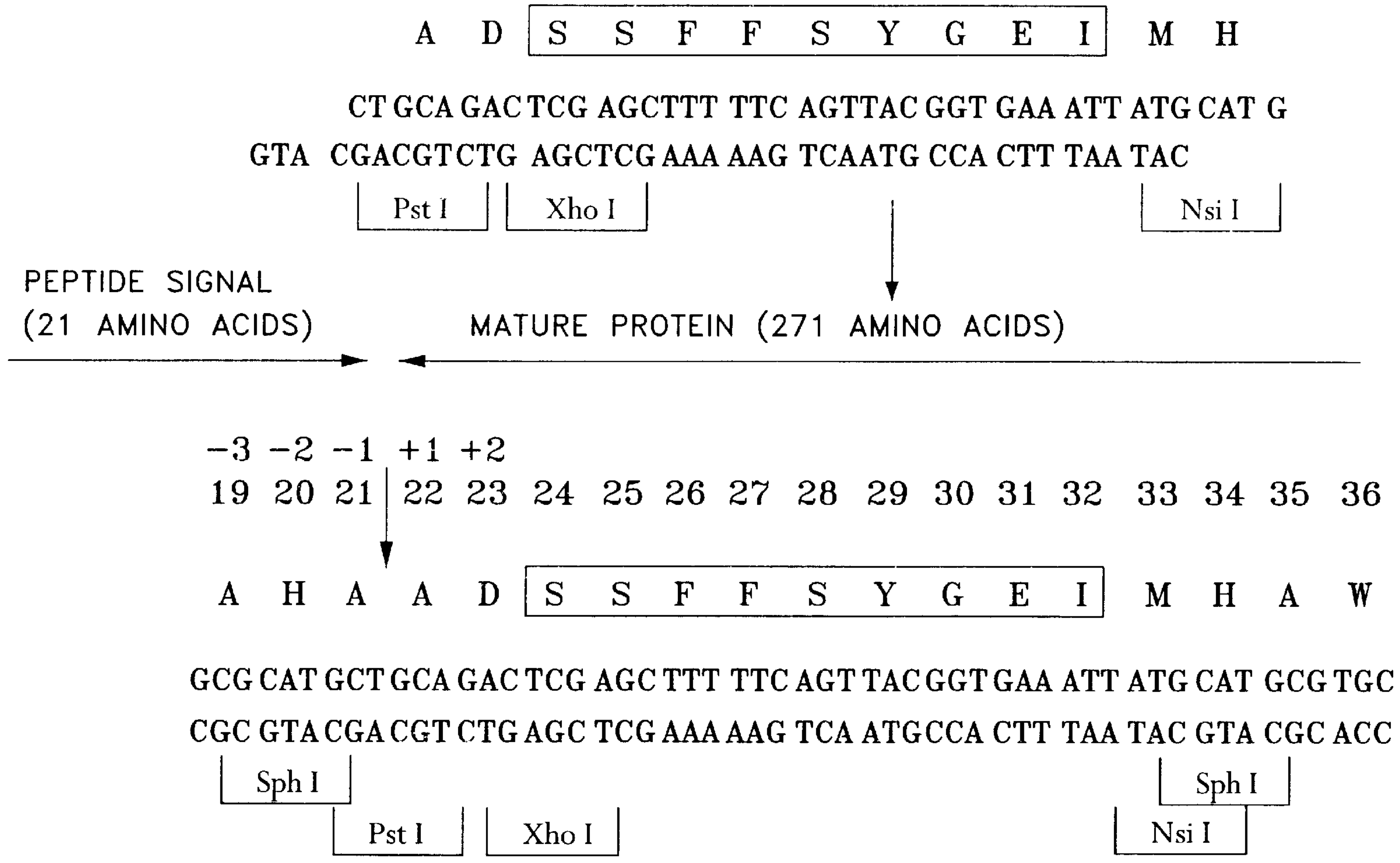

III. Directed Insertion of the C Epitope of the TGE Virus Between the Signal Peptide and the Mature Peptide in the ClpG Pre-protein A non-phosphorylated double-stranded oligonucleotide (42 mers) was synthesized that codes for the C epitope of a total of 9 amino acids (SSFFSYGEI SEQ ID NO:40) and that contains the SphI site (5'-GCATGC-3') at each of its ends. This oligonucleotide also contains the PstI, XhoI, and NsiI restriction sites. The insertion of the synthesized oligonucleotide at the single SphI site on the pDEV41155 recombinant plasmid (as shown in FIG. 12) is illustrated in FIG. 39. The recombinant plasmid resulting from this insertion is designated as "pGISA". FIG. 39 illustrates the insertion plan for the C epitope of the TGE virus between the signal peptide and the mature protein of the ClpG pre-protein. The sequence shown in boldface characters indicates the synthesized oligonucleotide sequence that was inserted into the clpG gene. The amino-acid sequence that corresponds to the C epitope of the TGE virus is enclosed within a square. The sequence that consists of the 14 amino acids shown in boldface characters corresponds to the peptide that was added to the peptide sequence of the mature ClpG protein.

The SphI site in the clpG gene is located 7 base pairs upstream of the TGG codon that corresponds to the first amino acid (tryptophan:W) in the mature ClpG protein. The initial cutting site (AHA/WT SEQ ID NO:41) for the signal peptidase was modified and optimized (AHA/AD SEQ ID NO:42). The final result of the insertion leads to the addition of the 14 amino acids (ADSSFFSYGEIMHA SEQ ID NO:43) in the peptide sequence in the mature ClpG protein located between positions −1 and +1 in the initial peptide sequence.

After cloning of the synthetic oligonucleotide at the SphI site on the clpG gene and the transformation of the DH5α *E. coli* strain, the hybrid clones were tested by means of immunoblotting with a native anti-CS31A serum and the Mac 3b.5 monoclonal antibody that is specific for the C epitope.

Two immunological techniques were utilized, namely, in situ immunodetection of the native hybrid protein on colonies, and the immunodetection of the denatured hybrid proteins on Western blots.

In both cases, the results indicate that the hybrid ClpG/C epitope proteins are immunoreactive. They also demonstrate that the hybrid ClpG proteins are normally exported and polymerized in order to form the CS31A, and that the C epitope is exposed at the surface of the CS31A.

IV. Co-insertion of Viral Epitopes in the ClpG Protein

1) Co-insertion of the A and C Epitopes of the TGE Virus a) Between the Signal Peptide and the Mature Peptide of the ClpG Pre-protein a.1) A non-phosphorylated double-stranded oligonucleotide (36 mers) was synthesized that has the following sequence:

(5'-TCG ATG AAG AGA TCT GGC TAT GGT CAG CCT ATT GCG-3' SEQ ID NO:44

3'-AC TTC TCT AGA CCG ATA CCA GTC GGA TAA CGC AGC T-5'SEQ ID NO:45)

This oligonucleotide also codes for the A epitope with 12 amino acids (SMKRSGYGQPIA SEQ ID NO:46), and has an XhoI-compatible (5'-CTC GAG-3') site at each of its ends. This oligonucleotide, which contains the BglII restriction site (5'-AGA TCT-3'), was inserted at the single unique XhoI site on the pGISA recombinant plasmid (see Section H, paragraph III, and FIG. 39). The XhoI site is located immediately upstream of the sequence that codes for the C epitope of the TGE virus. Accordingly, the co-insertion of the A and C epitopes of the TGE virus between the signal peptide and the mature peptide of the ClpG pre-protein ultimately corresponds to an additional heterologous sequence of 26 amino acids in relation to the original ClpG pre-protein, as indicated below:

-1 +1

AHA ADSMKRSGYGQPIA SSFFSYGEIM HAW-ClpG SEQ ID NO: 47

The A epitope for TGEV The C epitope for TGEV

+26 amino acids

The modified clpG gene that contained the sequence that codes for the A epitope and also the sequence that codes for the C epitope of the TGE virus has been replaced by molecular cloning in its original operon, which itself had been cloned beforehand in the pHSG575 plasmid (as described by C. Martin et al. (1991)). The final construction led to the acquisition of the pGAC524 plasmid. The in situ immunodetection of the native modified proteins on colonies and the immunodetection of the denatured hybrid proteins on Western blots with a native anti-CS31A serum (see FIG. 40) and monoclonal antibodies for the C and A sites of the TGE virus have demonstrated that the tri-hybrid proteins (i.e., the proteins consisting of the TGE virus A epitope, the TGE virus C epitope, and the ClpG protein) were still immunoreactive. This finding indicates that the tri-hybrid ClpG protein was expressed, exported, and polymerized in order to form the CS31A capsule.

a.2) Another construction was also implemented that is analogous to the preceding one, but different in that in it, the A and C epitopes for the TGE virus are positioned upstream of the clpG gene. In this case, the A epitope was inserted not before the C site, but rather after it, between the signal peptide and the mature peptide of the ClpG pre-protein, as indicated below.

A non-phosphorylated double-stranded oligonucleotide (36 mers) was synthesized that has the following sequence:

(5'-G AAA AGA TCT GGT TAT GGA CAG CCG ATT GCA GTG CA-3' SEQ ID NO:48

3'-AC GTC TIT TCT AGA CCA ATA CCT GTC GGC TAA CGT C-5' SEQ ID NO:49)

This oligonucleotide also codes for the A epitope with 12 amino acids (KRSGYGQPIAVH SEQ ID NO:50), and has an NsiI-compatible (5'-ATG CAT-3') site at each of its ends. This oligonucleotide, which contains the BglII restriction site (5'-AGA TCT-3'), was inserted at the single unique NsiI site on the pGISA recombinant plasmid (see Section H, paragraph III, and FIG. 39). The NsiI site is located immediately downstream of the sequence that codes for the C epitope of the TGE virus. Accordingly, the co-insertion of the A and C epitopes of the TGE virus between the signal peptide and the mature peptide of the ClpG pre-protein corresponds to an additional heterologous sequence of 26 amino acids in relation to the original ClpG pre-protein, as indicated below:

-1 +1

AHA AD SSFFSYGEI MX KRSGYGQPIAVHAW-ClpG SEQ ID NO: 51

The C epitope for TGEV The A epitope for TGEV

+26 amino acids

The final construction led to the acquisition of the pGAC41155 plasmid. The in situ immunodetection of the denatured hybrid proteins on Western blots with a native anti-CS31A serum (see FIG. 40) and monoclonal antibodies for the C and A sites of the TGE virus has demonstrated that the tri-hybrid proteins (i.e., the proteins consisting of the TGE virus C epitope, the TGE virus A epitope, and the ClpG protein) were very immunoreactive. This result indicates that the tri-hybrid ClpG protein was expressed, exported, and polymerized in order to form the CS31A capsule. However, the level of expression of the ClpG, as evaluated by means of the Western blot with these three types of antibodies, appears to be weaker in the case of the tri-hybrid protein consisting of NH2, the TGE virus A epitope, the TGE virus C epitope, the ClpG protein, and COOH, in comparison with the tri-hybrid protein consisting of NH2, the TGE virus C epitope, the TGE virus A epitope, the ClpG protein, and COOH.

This difference may be due to the type of positioning of the A and C epitopes in the ClpG protein, resulting in a more or less restrictive configuration of the overall heterologous sequence, in such a way as to affect one of the stages involved in the biogenesis of the CS31A. This difference may also be due to the complementation system (i.e., trans- or cis- complementation) used to study the expression of the CS31A in each of these constructions.

b) In the V3 Region b.1) A non-phosphorylated double-stranded oligonucleotide (36 mers) was synthesized that has the following sequence:

(5'-CTA GCG ACT CGA GCT TCT TTT CGT ACG GTG ACA TTC-3' SEQ ID NO:52

3'-GC TGA GCT CGA AGA AAA GCA TGC CAC TCT AAG GAT C-5' SEQ ID NO:53)

This oligonucleotide also codes for the C epitope with 12 amino acids (SDSSFFSYGETP SEQ ID NO:3), and has an SpeI-compatible (5'-ACT AGT-3') site at each of its ends. This oligonucleotide, which contains the XhoI and SplI restriction sites (5'-CTC GAG-3') and (5'-CGT ACG-3'), was inserted at the single unique SpeI site on the pGA102 plasmid (see FIG. 34) that contains the coding sequence for the A epitope of the TGE virus (see FIG. 27). Accordingly, in the final construction the C epitope of the TGE virus was positioned immediately upstream of the A epitope of the TGE virus. The plasmid resulting from the co-insertion of these two epitopes is the pGCA102 plasmid, as indicated below:

NH2-ClpG-NKTS DSSFFSYGEIPS MKRSGYGQPIA GDL (SEQ ID NO: 54)-ClpG-COOH

The TGEV C epitope The TGEV A epitope

The hybrid ClpG proteins were tested by means of immunoblotting with a native anti-CS31A serum (see FIG. 40), a monoclonal antibody for the A epitope of the TGE virus, and the Mab 3b.5 antibody that is specific for the C epitope. Two immunological techniques were utilized, i.e., in situ immunodetection of the native hybrid proteins on colonies, and immunodetection of denatured hybrid proteins on Western blots (see FIG. 40).

The results indicate very good immunoreactivity for the tri-hybrid protein consisting of NH2, the ClpG protein, the TGE virus C epitope, the TGE virus A epitope, the ClpG protein, and COOH with the three antibodies.

Nevertheless, the results obtained on Western blots with the anti-CS31A polyclonal antibodies indicate that a sub-population of this tri-hybrid is truncated at the A epitope of the TGE virus. In fact, two bands were actually displayed on the Western blots, i.e., a dominant upper band corresponding to the complete tri-hybrid protein, and a weak lower band corresponding only to the protein portion of the ClpG gene located upstream of the A epitope of the TGE virus.

b.2) A non-phosphorylated double-stranded oligonucleotide (36 mers) was synthesized that has the following sequence:

(5'-TCG ATG AAG AGA TCT GGC TAT GGT CAG CCT ATT GCG-3' SEQ ID NO:55

3'-AC TTC TCT AGA CCG ATA CCA GTC GGA TA CGC ACG T-5' SEQ ID NO:56)

This oligonucleotide also codes for the A epitope with 12 amino acids (SMKRSGYGQPIA SEQ ID NO:46), and has an XhoI-compatible (5'-CTC GAG-3') site at each of its ends. This oligonucleotide, whicih contains the single unique BglII restriction site (5'-AGA TCT-3'), was inserted at the single unique XhoI site on the pGC326 recombinant plasmid located upstream of the sequence that codes for the C epitope of the TGE virus (see Section H, paragraph I). The co-insertion of the A and C epitopes of the TGE virus corresponds to an additional heterologous sequence of 24 amino acids in relation to the original ClpG pre-protein, as shown below:

T SDS MKRSGYGQPIA SFFSYGEIP S SEQ ID NO: 57

The TGEV A epitope The TGEV C epitope

+24 amino acids

The final construction led to the acquisition of the pGAC326 plasmid. The immunodetection of the denatured hybrid proteins on Western blots with a native anti-CS31A serum and monoclonal antibodies for the C and A epitopes of the TGE virus has demonstrated that the CS31A is expressed by the bacteria that contain the pDSPH524+ pGAC326 plasmids. However, a large population of tri-hybrid proteins appears to be truncated at the A epitope. Three bands were displayed on the Western blots with the anti-CS31A polyclonal antibody, i.e., a minor upper band corresponding to the complete tri-hybrid protein, a large intermediate band corresponding to the protein portion located upstream of the A epitope of the TGE virus, and a weak lower band corresponding to the protein portion of the ClpG gene located downstream of the A epitope of the TGE virus.

Figure 40:
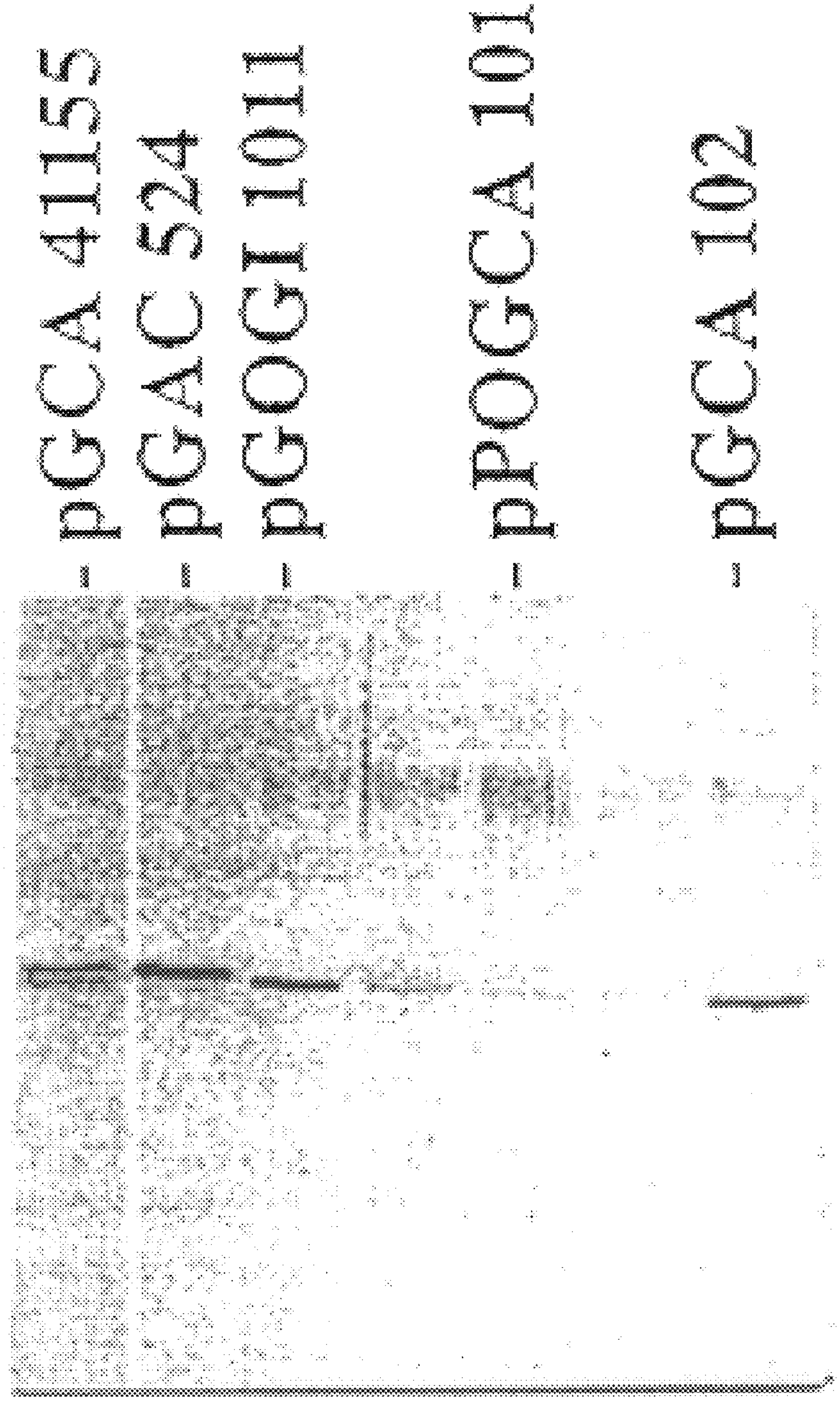
FIG. 40 shows results of Western immunoblotting with native anti-CS31A serum with monoclonal antibodies directed against the A or C epitopes.

2) Preservation of the C Epitope of the TGE Virus and of the C3 Epitope of the VP1 [Protein] of the Type 1 Polio Virus Starting with the pGISA plasmid (see FIG. 39) and the pP101 plasmid (see FIG. 34), the nucleotide sequences that code for the C epitope of the TGE virus and the C3 epitope of the VP1 [protein] were simultaneously replaced, by means of molecular cloning, in the CS31A operon that had been cloned beforehand in the pHSG575 plasmid (as described by Martin et al. (1991)). The final construction led to the acquisition of the pPOG11101 plasmid. In this construction the C epitope of the TGE virus is located between the signal peptide and the mature ClpG peptide, between the amino acids located at positions −1 and +1 in FIGS. 9 and 32, and the C3 epitope of the Vp1 protein is located in the V3 region of the ClpG peptide between the amino acids located at positions 202 and 215 in FIGS. 9 and 39. The study of the expression of the ClpG protein that includes both the C epitope of the TGE virus and the C3 epitope of the VP1 protein shows that the biogenesis of CS31A was detectable but weak. In point of fact, the results obtained through Western immunoblotting with a native anti-CS31A serum (as indicated in FIG. 40) and with the Mab 3b.5 antibody that is specific for the C epitope of the TGE virus actually indicate a drop in the level of expression of the ClpG in comparison with that of the unmodified homologous protein.

3) Co-insertion of the A and C Epitopes of the TGE Virus and of the C3 or VP1 Epitopes of the Type 1 Polio Virus A non-phosphorylated double-stranded oligonucleotide (36 mers) was synthesized that has the following sequence:

(5'-G AAA AGA TCT GGT TAT GGA CAG CCG ATT GCA GTG CA-3' SEQ ID NO:48

3'-AC GTC TTT TCT AGA CCA ATA CCT GTC GTC GGC TAA CGT C-5' SEQ ID NO:49)

This oligonucleotide codes for the A epitope with 12 amino acids (KRSGYGQPIAVH SEQ ID NO:50), and includes a site that is compatible with the NsiI (5'-ATG CAT-3') site located at each of the ends to be synthesized.

This oligonucleotide, which contains the BglII (5'-AGA TCT-3' ) site, was inserted at the single unique NsiI site on the pPOGI1011 recombinant plasmid (as described in Section H, paragraph IV). This plasmid contains the nucleotide sequence that codes for the C3 or VP1 epitope located in the V3 region of the ClpG gene (located between the amino acids located at positions 202 and 215 in FIGS. 9 and 32) and the sequence that codes for the C epitope of the TGE virus located between the signal peptide and the mature ClpG peptide (located between the amino acids located at positions −1 and +1 in FIGS. 9 and 32). The NsiI site is located immediately downstream of the sequence that codes for the C epitope of the TGE virus. The plasmid resulting from this construction is the PPOGCA101 plasmid. Thus, the co-insertion of the C and A epitopes of the TGE virus and of the C3 polio epitope into the ClpG gene corresponds to an additional heterologous sequence of 26 amino acids in relation to the original ClpG protein, as shown below:

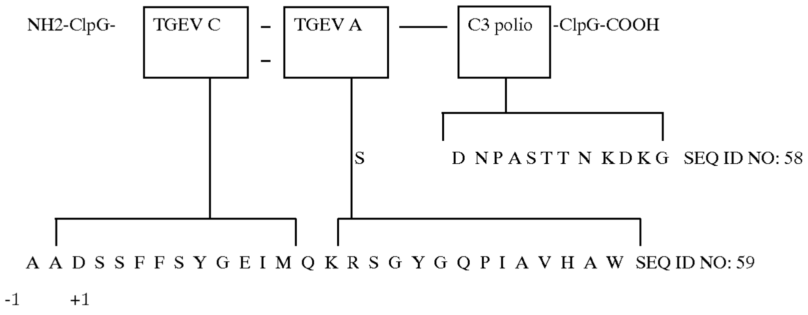

The results obtained through Western immunoblotting with a native anti-CS31A serum (as shown in FIG. 40) and with the monoclonal antibodies directed against the A or C epitopes of the TGE virus indicate a major decrease in the level of expression of the tetra-hybrid (i.e., $NH_2$ plus ClpG plus the C epitope of the TGE virus plus the A epitope of the TGE virus plus the C3 polio epitope plus the ClpG protein) in comparison with the unmodified ClpG protein, and even in comparison with all of the tri-hybrids obtained.

I) Conclusions Regarding the Insertion of Viral Epitopes into the Clpg Protein

Among the four permissive regions A, B, C, and D for heterologous insertions or substitutions, the cloning of synthetic DNA fragments that correspond to various viral epitopes has been achieved in regions A, C, and D.

1) In Region A

Constructions through insertion have been obtained in accordance with two different strategies (i.e., insertions after random mutagenesis, or directed insertions via direct cloning). In both instances, the sequence that corresponds to the C epitope of the TGE virus was cloned in the N-terminal position between the signal peptide and the mature peptide of the ClpG pre-protein (i.e., between the amino acids located at positions −1 and +1 in FIG. 9). In both cases, the hybrid protein (i.e., ClpG plus the C epitope of the TGE virus) is produced in large quantity, and the epitope is recognized by the monoclonal antibody in the hybrid protein under its native form.

In some cases, heterologous peptide sequences with from 5 to 20 amino acids have been introduced through insertion or substitution, after random mutagenesis, into the ClpG pre-protein between the amino acids located at positions −13 and +8 in FIG. 9 without disturbing the biogenesis of the CS31A.

2) In Region C

Five different constructions that include the sequence that corresponds to the C epitope of the TGE virus (i.e., pGC32, pGC19, pGC1, pGC4, and pGC44), as well as a sixth construction (pF1) that codes for an epitope of the VP1 protein of the aphthous fever virus, have been obtained by insertion or substitution. In all of these cases, the biogenesis of the hybrid CS31A/epitope capsular protein has been affected, in that the protein sub-units are no longer exported and polymerized on the surface of the bacterium.

3) In Region D

The following types of constructions have been obtained in this region:

a) Constructions by Substitution

Three constructions that include the sequence that corresponds to the C epitope of the TGE virus (i.e., pGG103, pGP105, and pGP684); two constructions with the sequence that codes for the C3 epitope of the polio virus (i.e., pP101 and pP686); one construction with the sequence for the A epitope of the TGE virus (i.e., pGA102); and one construction with the sequence for the epitope of the bovine rotavirus (pR104); and, finally, one construction with theÃsequence that corresponds to an epitope of the VP1 protein of the virus for aphthous fever (i.e., pF681). The pGG103, pGP105, and pGP684 plasmids make it possible to obtain a good expression of the hybrid proteins that consist of CS31A plus the C epitope of the TGE virus on the surface of the bacterium. With the three plasmids, the C epitope of the TGE virus is recognized by the monoclonal antibody in the hybrid protein in its native form. With the constructions that code for the hybrid proteins that consist of CS31A plus the C3 epitope of the Ãpolio virus, the pP101 plasmid allows a good expression of the hybrid protein. However, with the pP688 plasmid the expression is weak. With the construction that codes for an epitope of the VP1 protein of the aphthous fever virus (i.e., pF681), the expression of the hybrid protein is weak. It is close to that of the control with the constructions that code for the A epiope of the TGE virus (i.e., pGA102) or for the epitope of the bovine rotavirus (i.e., pR104).

Three constructions that include a heterologous sequence of 41 amino acids (i.e., the pDBB10 plasmid), 84 amino acids (i.e., the pDHS68 plasmid), and 100 amino acids (i.e., the pDSX68 plasmid). These three different heterologous sequences have been inserted into the terminal —COOH portion of the ClpG protein through the substitution of a peptide fragment defined in FIG. 9 by the amino acids located at positions 190 and 257, and, more specifically:

Between the amino acids located at positions 216 and 257, for the pDBB10 plasmid;

Between the amino acids located at positions 190 and 257, for the pDHS68 plasmid;

Between the amino acids located at positions 198 and 257, for the pDSX680 plasmid.

Of these three constructions, none of which prevents or negates the biogenesis of the CS31A, the construction that corresponds to the pDBB10 plasmid allows the best expression of the ClpG protein.

b) Constructions by Insertion

One construction that includes the sequence that corresponds to the C epitope of the TGE virus (i.e., the pGC326 plasmid), located between the ClpG amino acids at positions 203 and 204 in FIG. 9. The hybrid protein that consists of the ClpG protein and the C epitope, which is strongly recognized by the anti- CS31A polyclonal antibodies and the Mab 3b.5 monoclonal antibody directed against the C epitope, is largely expressed on the surface of the bacteria that contain the pDSPH524 and pGC326 plasmids.

Finally, several heterologous sequences that correspond either to two different epitopes of the same virus (such as the A and C epitopes of the TGE virus) or that correspond to two different epitopes of the same virus (such as the A and C epitopes of the TGE virus) plus an epitope of Ãanother virus (such as the C3 epitope of the VP1 protein of the Type 1 polio virus) have been successfully co-inserted into the same ClpG protein without disturbing the biogenesis of CS31A. The tri-hybrid proteins, such as the A and C epitopes of the TGE virus plus the ClpG protein, have been obtained through co-insertion of the A and C epitopes of the TGE virus, either in the N-terminal position (i.e., in Region A) or else in the V3 region of the ClpG protein (i.e., in Region D). A tetra-peptide, consisting of the A and C epitopes of the TGE virus plus the C3 polio epitope and the ClpG protein, has been obtained through co-insertion of the A andÃC epitopes of the TGE virus in the N-terminal position and the C3 polio epitope in the V3 region. All of the tri-hybrid proteins are recognized by the monoclonal antibodies directed against the A and C epitopes of the TGE virus and by the anti-ClpG monoclonal antibody. On the other hand, however, the tetra-hybrid is recognized strongly by the anti-ClpG polyclonal antibody, weakly by the anti-C epitope monoclonal antibody, and not at all by the anti-A epitope antibody.

J) IMMUNOGENICITY OF HYBRID PROTEINS, AS MEASURED BY THE PRODUCTION OF ANTIBODIES DIRECTED AGAINST THE CS31A PROTEIN AND AGAINST THE "C" OR "A" PEPTIDES OF THE T.G.E. VIRUS OR VIRAL PARTICLES. SERONEUTRALIZING EFFECT OF SERUMS.

Lots consisting of five Swiss mice from non-consanguineous OF1 lines were immunized with purified recombinant bacteria in their native or denatured form.

I. Immunization Protocols and Measurement of the Activity of Serum Antibodies 1) Intraperitoneal Inoculation with Recombinant Bacteria

| | |
|---|---|
| Day 0: | 6 × $10^8$ bacteria in 0.3 ml of a mixture consisting of equal parts of physiological water (phy) and incomplete Freund's adjuvant (IFA): Lot A |
| Day 22: | 2 × $10^8$ bacteria in 0.1 ml of a mixture of phy and IFA |
| Day 36: | 2 × $10^8$ bacteria in 0.1 ml of a mixture of phy and IFA |

This same immunization protocol was also followed for inoculations consisting of 0.3 ml of bacteria without IFA: Lot B 2) Intraperitoneal Inoculation with Purified Recombinant Proteins a) In denatured form:

Lot C. The proteins in an aqueous solution were injected intraperitoneally at a volume of 0.3 ml, one-half of which consisted of incomplete Freund's adjuvant.

| | |
|---|---|
| Day 0: | 20 μg of proteins |
| Day 22: | 20 μg of proteins |
| Day 36: | 20 μg of proteins |

b) In Native Form:

Lot D. The protocol was identical, but the protein in native form in an aqueous solution was associated with an aluminum hydroxide gel. The final concentration of Ã$Al(OH)_3$ was 30 percent, and the mice received 0.3 ml, administered intraperitoneally.

The memory effect of the hyperimmunizations performed with the whole bacteria or with the purified proteins was measured after a booster administered at approximately Day 150, in the form of an intraperitoneal inoculation of recombinant bacteria (0.2 ml containing $4\times10^8$ bacteria in a mixture consisting of one-half phy and IFA) for Lot A and Lot B; recombinant proteins (7 μg of proteins in 0.1 ml of a mixture consisting of one-half water and IFA for the proteins in denatured form for Lot C, or else an aqueous suspension containing approximately $10^8$ PFU/ml of the Purdue strain of the TGE virus in 0.3 ml for the mice in Lot D that have been immunized with the recombinant protein in native form.

3) Measurement of Antibody Titers

Blood was drawn from each mouse at Day 0, Day 21, Day 35, and Day 150, and also 10 days after the second booster, i.e., at Day 45 (after hyperimmunization), and 6 days after the booster at Day 150, so that the memory effect could be measured.

The IgGs directed against the CS31A protein, [against] the C and A peptides of the TGE virus, and also against the TGE viral particles were measured by means of an indirect ELISA technique. Serum from the mice was distributed, at a dilution of one-half, into the wells of ELISA plate that had been sensitized with the purified CS31A protein. After incubation and washing, the anti-IgGs of the mice marked with peroxidase was caused to react. After incubation and washing, the IgGs were revealed by means of hydrogen peroxide ($H_2O_2$) in the presence of 2-2'-azino-bis-(3-ethyl benzthiazoline-6-sulfonic acid), known as "ABTS". A reading was taken of the intensity of the coloration at a wavelength of 405 nm. The antibody titer was then defined in conjunction with the dilution of the serum so as to yield an optical density of 0.3.

The titers of the antibodies directed against the heterologous peptide introduced into the CS31A were measured in accordance with this same method, but with the difference that the ELISA plates were sensitized with either a synthetic peptide or TGE viral particles. The synthetic peptides corresponding to the C and A epitopes of the TGE virus have the following compositions, respectively: T V S D S S F F S Y G E I P F SEQ ID NO:60 and SMKRSGYGQPIAG SEQ ID NO:61.

4) Seroneutralizing Effect of Serums

The seroneutralizing effect against the TGE virus was measured in accordance with the technique described by Laude et al. in *J. Gen. Microbiol.,* Vol. 67 (1986), pp. 119–130. One-half to one-third dilutions of the antiserum were mixed with a viral suspension containing 500 PFU of the Purdue-115 strain of the TGE virus. After one hour of incubation at a temperature of 37° C., $4\times10^4$ cells from the ST line were added. The neutralization titer was read 40 hours later. A reference serum was included for each experiment. The titer was expressed in terms of the inverse of the dilution of the serum protecting the cell fabric from the cytopathogenic effect of the virus.

II. Results

The various constructions described above generally correspond to viral peptide sequences that have been introduced into the permissive zones and are natural immunogens of the CS31A protein.

Figures 41A, 41B, 41C, 41D:
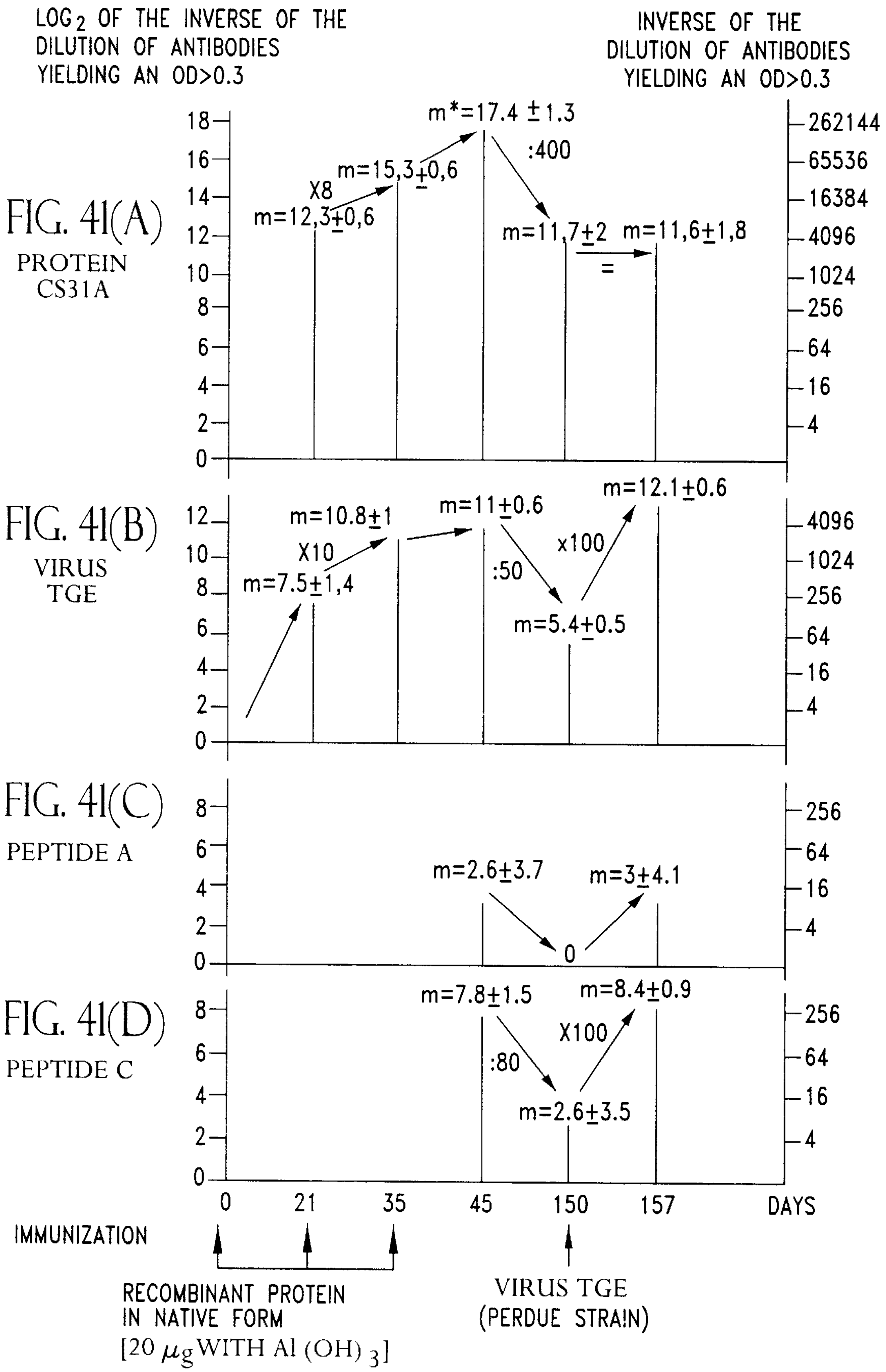
FIG. 41 shows titers of antibodies produced by mice immunized with GCA102 recombinant protein in native form.

As an example, FIGS. 41 to 45 present the titers and seroneutralizing effects of the serum antibodies produced in the immunized mice with the recombinant bacteria and proteins obtained with the pGCA102 plasmid. With this plasmid, the C and A epitopes of the TGE virus were produced in the V3 permissive zone in which a linear epitope had been identified that was exposed on the surface of the CS31A protein in native form.

in FIGS. 41(A–D) represent the titers of the antibodies produced by the mice immunized with the GCA102 recombinant protein in native form, in association with aluminum hydroxide, and recognizing, respectively:

in FIG. 41(A), the CS31A protein in FIG. 41(B), the TGE virus in FIG. 41(C), the A peptide in FIG. 41(D), the C peptide In these figures, "m" is the mean of the log2 of the inverse of the dilutions of the antibody yielding an optical density greater than 0.3.

Figure 42:
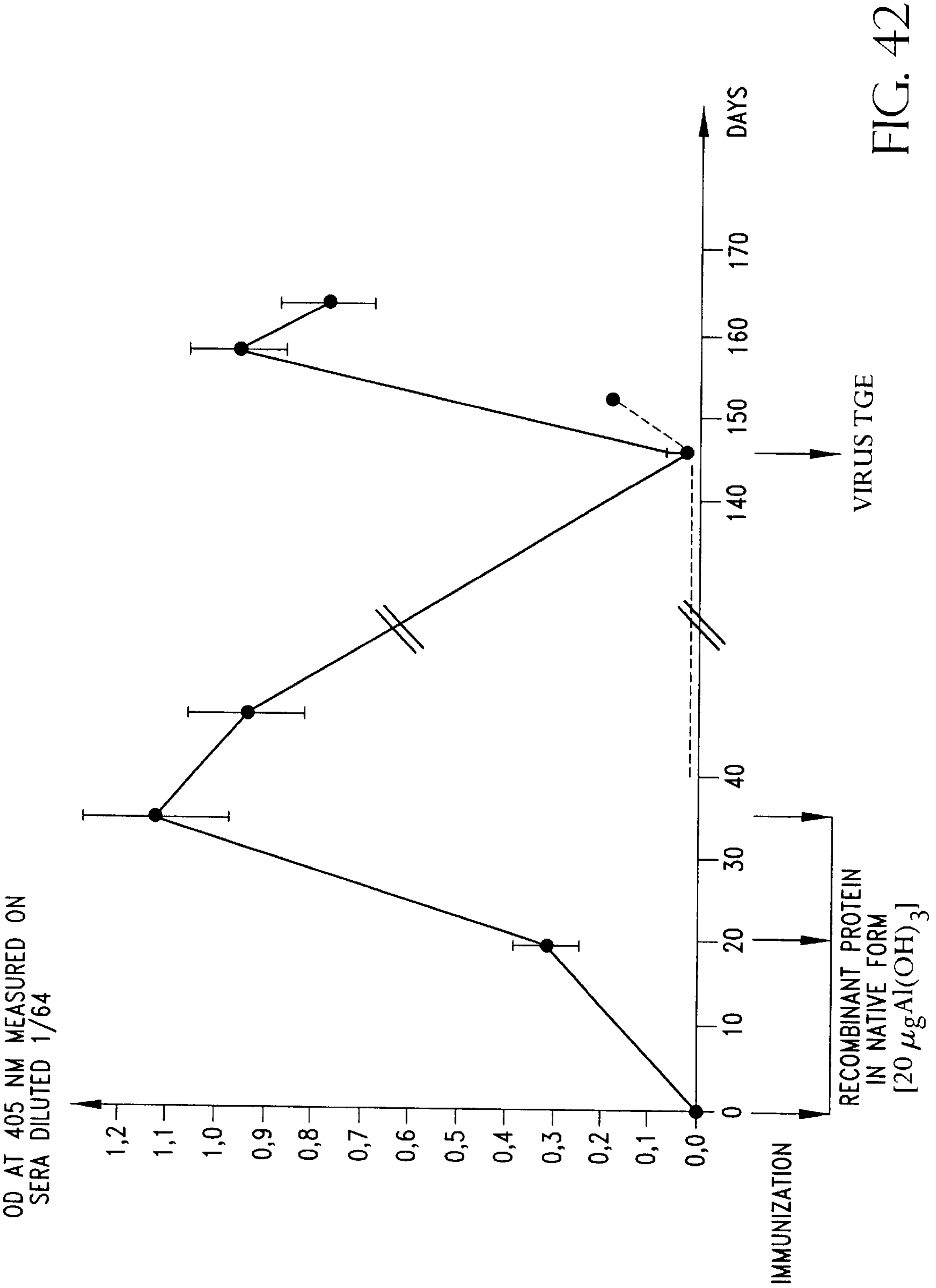
FIG. 42 shows titers of anti-peptided C antibodies produced by mice immunized with GCA102 recombinant protein in native form.
Figures 43A, 43B, 43C, 43D:
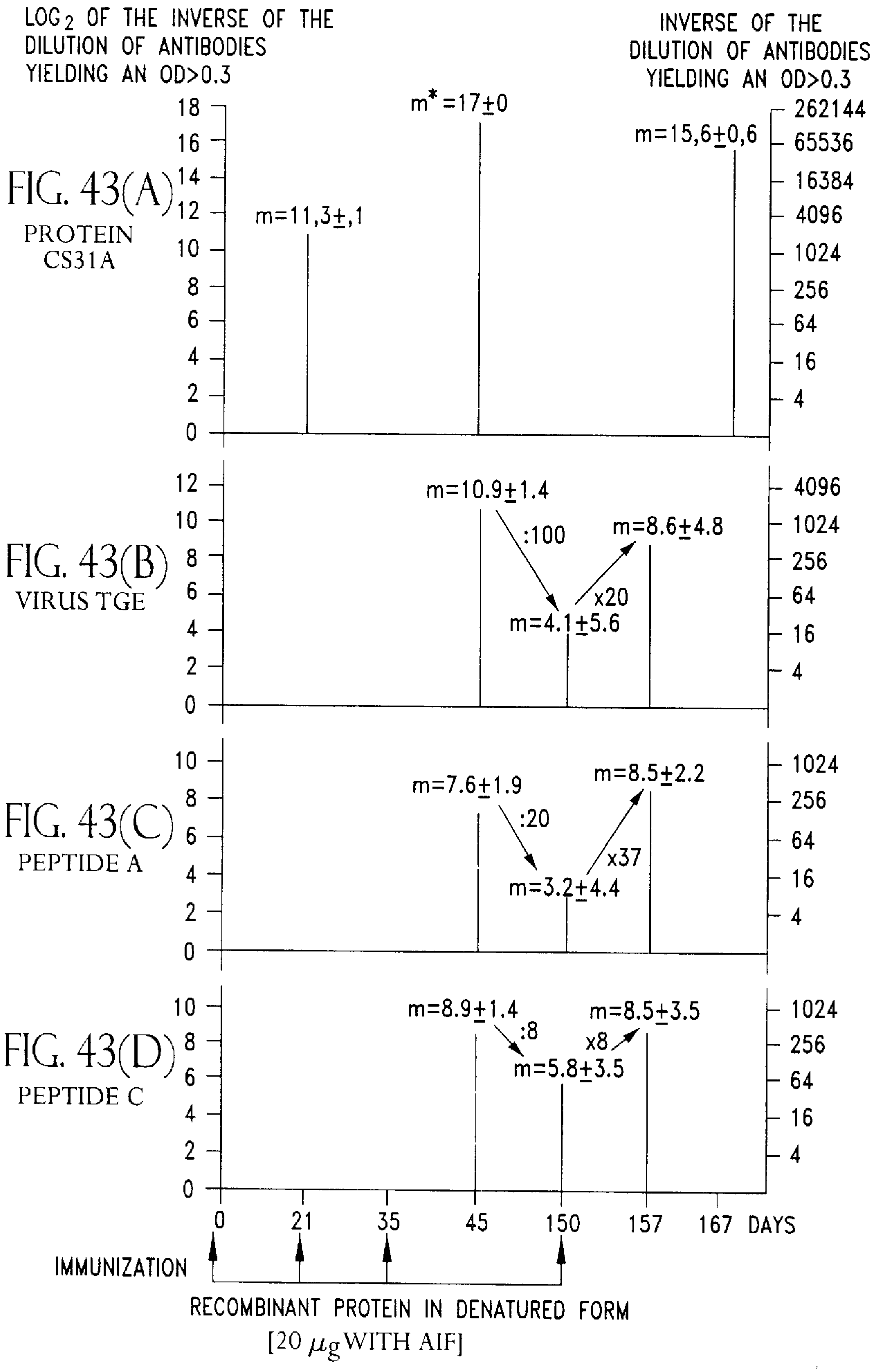
FIG. 43 shows the titers of antibodies produced by mice immunized with GCA102 recombinant protein in denatured form (IFA).
Figures 44A, 44B, 44C, 44D:
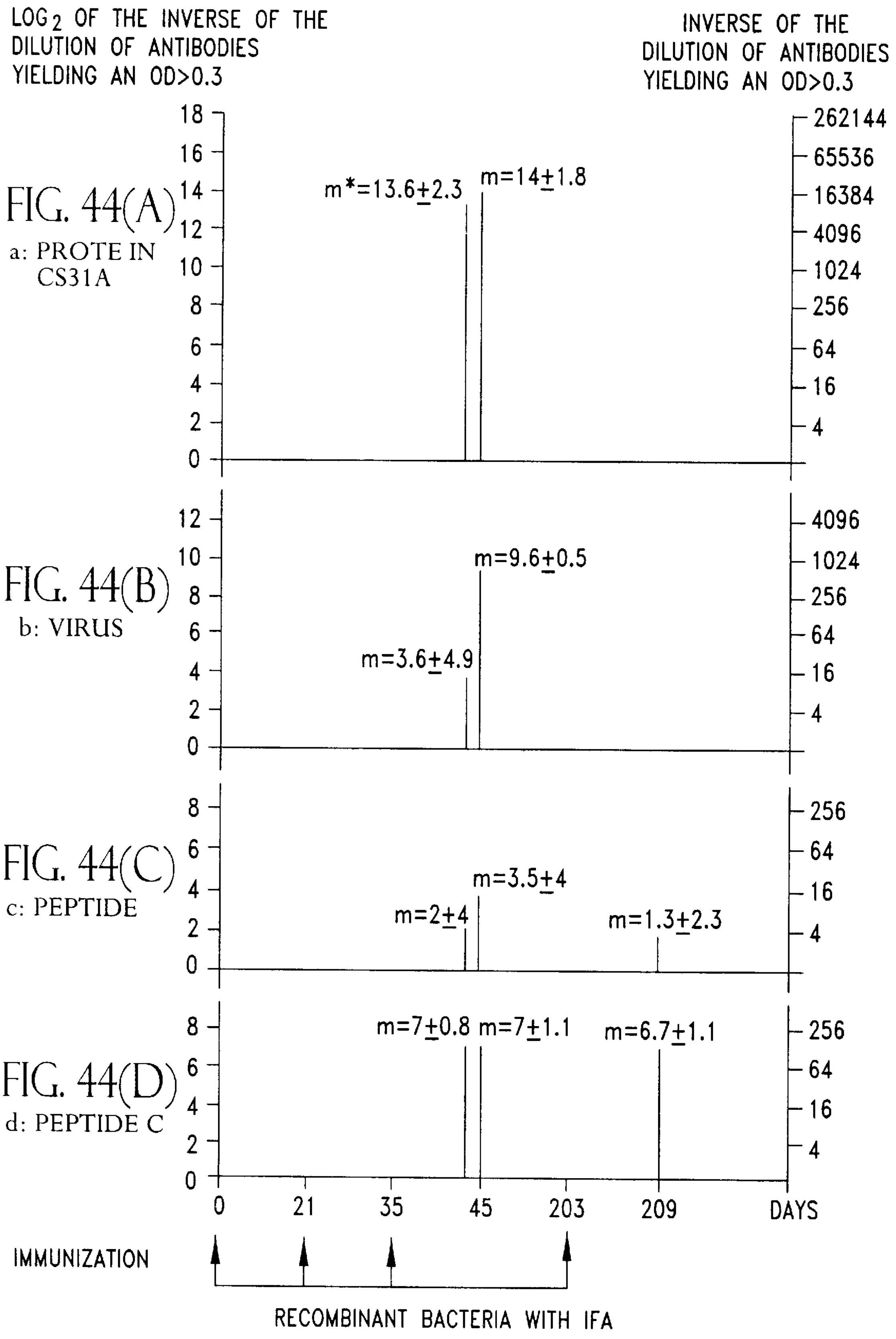
FIG. 44 shows the titers of antibodies produced by mice immunized with the bacteria that produce GCA102 recombinant protein (with IFA).
Figures 45A, 45B, 45C, 45D:
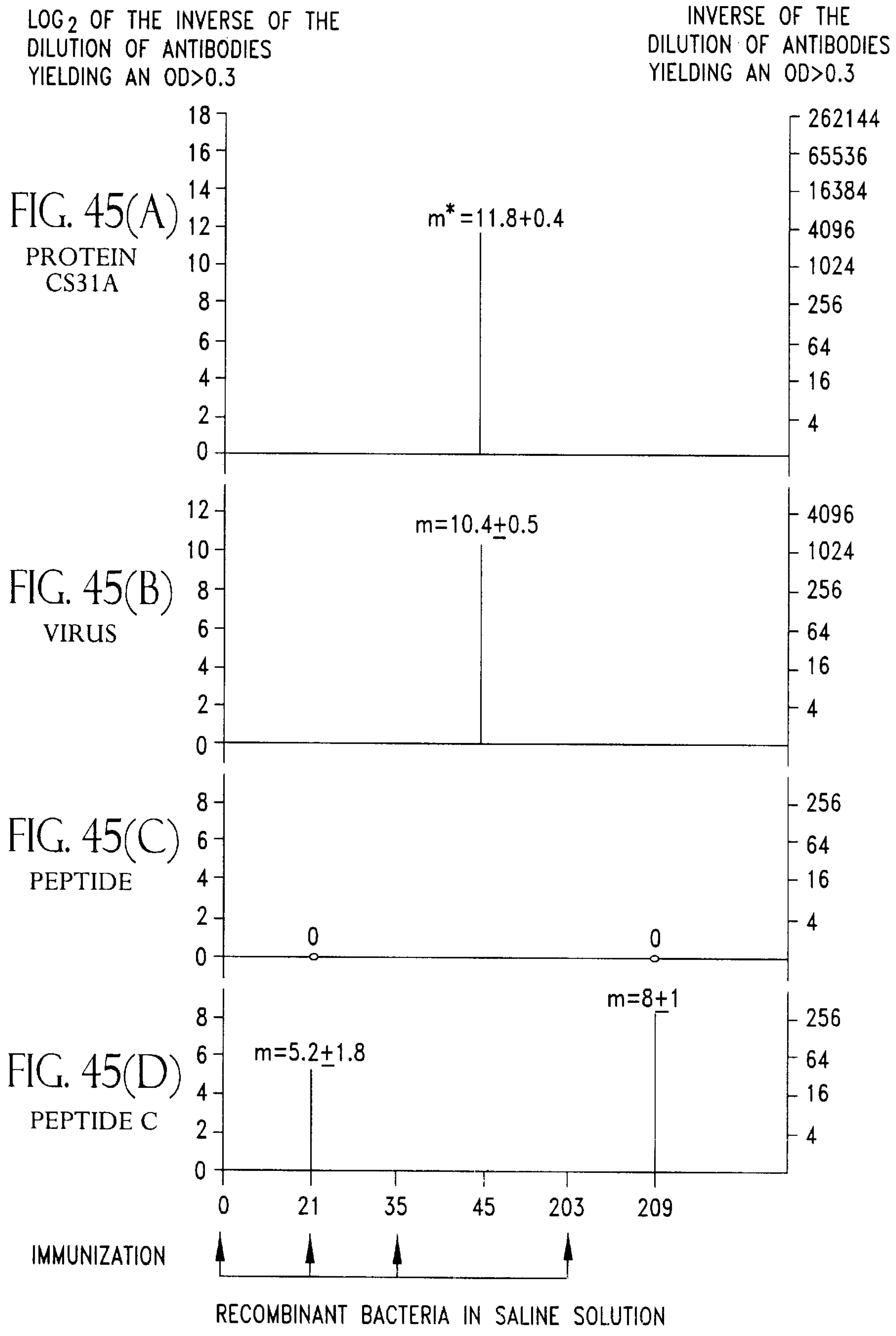
FIG. 45 shows the titers of antibodies produced by mice immunized with the bacteria that produce GCA102 recombinant protein (in saline solution).

FIG. 42 represents the titers of the anti-peptide C antibodies produced by the mice immunized with the GCA102 recombinant protein in native form, and then with the TGE virus. In this figure, the dotted line corresponds to the control mice that were immunized with a heterologous recombinant protein and then with the TGE virus on Day 146.

in FIGS. 43(A–D) represent the titers of the antibodies produced by mice immunized with the GCA102 recombinant protein in denatured form (with IFA), and recognizing, respectively:

in FIG. 43(A), the CS31A protein in FIG. 43(B), the TGE virus in FIG. 43(C), the A peptide in FIG. 43(D), the C peptide In these figures, "m" is the mean of the log2 of the inverse of the dilutions of the antibody yielding an optical density greater than 0.3.

in FIGS. 44(A–D) represent the titers of the antibodies produced by the mice immunized with the bacteria that produce the GCA102 recombinant protein (with IFA), recognizing, respectively:

in FIG. 44(A), the CS31A protein in FIG. 44(B), the TGE virus in FIG. 44(C), the A peptide in FIG. 44(D), the C peptide In these figures, "m" is the mean of the log2 of the inverse of the dilutions of the antibody yielding an optical density greater than 0.3.

in FIGS. 45(A–D) represents the titers of the antibodies produced by the mice immunized with the bacteria that produce the GCA102 recombinant protein (in a saline solution), recognizing, respectively:

in FIG. 45(A), the CS31A protein in FIG. 45(B), the TGE virus in FIG. 45(C), the A peptide in FIG. 45(D), the C peptide In these figures, "m" is the mean of the log2 of the inverse of the dilutions of the antibody yielding an optical density greater than 0.3.

The mice immunized with the recombinant protein in native form in association with aluminum hydroxide produce an antibody that recognizes the viral particles with a high titer (see FIG. 41(B)) after the first hyperimmunization stage (at Day 45). The second booster, at Day 35, produced a slight increase in the anti-CS31A response, but had no effect on the anti-TGE virus titer.

After a rest of approximately 100 days, the titers decreased significantly (by a factor of 50 in relation to their values on Day 45).

After inoculation with the Purdue strain of the TGE virus, the anti-TGE virus titers rose again very rapidly (100 times greater after 6 days), thereby indicating that the vaccination had induced a memory effect. Similar results, although less intense, were observed in conjunction with measurements of the titers of the antibodies that recognize the A peptides (see FIG. 41(C)) and the C peptides (see FIG. 41(D)). These instances involve a specific response in opposition to the viral sequence, inasmuch as the titer of the anti-CS31A antibodies does not change after inoculation with the virus. Furthermore, it can also be noted that the titers of the antibodies directed against the C peptide are always higher than those of the antibodies directed against the A peptides.

The results involving the titers of the antibodies directed against the C peptides are presented in a different form in FIG. 42. In this figure, the titers of the antibodies are measured in accordance with the mean of the log2 of the inverse of the dilution of the serums yielding an optical density greater than 3 in FIGS. 41, 43, 44, and 45. With this representation, the standard deviations are smaller, but the evolutions of the curves are similar.

The results obtained for the mice immunized with the GCA102 recombinant protein in native form are essentially identical to the results observed in the mice immunized with the GCA102 recombinant protein in denatured form (see FIG. 43). The primary difference was observed for the titers of the antibodies directed against the A peptides (see FIG. 43), which are clearly higher with the GCA102 protein in denatured form. Stimulation of the memory cells was very clearly observed in connection with the booster at Day 150 with the denatured recombinant protein.

Comparable results have been obtained in mice that were immunized with recombinant bacteria that were either associated (as shown in FIG. 44) or not associated (as shown in FIG. 45) with the Freund's adjuvant complex. However, the titers are lower than in the mice that were immunized with the purified proteins.

Results regarding the seroneutralizing effect of the serums were obtained through measurements made at Day 45 of the serums of two mice that were immunized with the GCA102 protein in denatured form. These two serums had anti-TGE virus titers of 4,000, and were neutralized at a ratio of 1/150 for one and at a ratio of 1/500 for the other in connection with the TGE virus.

III. Conclusions

The results reported above show that viral peptide sequences introduced into the permissive and immunodominant V3 region of the CS31A protein make it possible to induce a good anti-viral vaccinal response in animals that have been immunized with these bacteria or with these recombinant proteins.

A good vaccine should provide long-lasting immunity and an immunological memory that ensures a rapid protective immune response on the occasion of a subsequent contact with the infectious agent that is the target of the vaccination.

The experimental results obtained in mice indicate that the vaccination against the TGE virus, as measured by the titers of the antibodies directed against the entire virus or against the S-glycoprotein peptide sequences (i.e., the A and C epitopes), were characterized by a significant increase in antibodies during the course of the hyperimmunization stage, followed by a very large rise when, 100 days later, the mice received a booster in the form of the recombinant proteins or bacteria or in the form of the TGE virus itself. This memory effect is characteristic of a good vaccination. The seroneutralizing effect, as measured on several serums, is also a significant result. It should also be noted that the majority of the non-consanguineous OF1 mice responded to the vaccination. Therefore, the vaccination peptide sequence does not appear to be subject to the CMH restriction. Finally, although the highest antibody titers were obtained when the mice were immunized with the purified recombinant proteins, the responses obtained with the recombinant bacteria also appear to be very significant.

REFERENCES

B. A. D. Stocker (1990). Res. Microbiol., 141, 787–796.

P. Klemm, L. Hedegaard (1990). Res. Microbiol., 141, 1013–1017.

De Graff F. K. (1988). J. of Microbiol., 59, 395–404.

M. Hofnung (1988). J. of Microbiol., 54, 442–445.

D. O'Callaghan, A. Charbit, P. Martineau, C. Leclerc, S. Van Der Werf, C. Nanciel, M. Hofnung (1990). Res. Microbiol., 121, 963–969.

J. L. Harrison, I. M. Taylor, C. D. O'Connor (1990). Res. Microbiol., 141, 1009–1012.

S. Pistor, G. Hobom (1990). Res. Microbiol., 141, 879–881.

FIGURES

[TRANSLATOR'S NOTE: None of the 45 figures was included with the French-language text submitted for translation.]

What is claimed is:

1. A ClpG sub-unit of a CS31A protein capsule wherein said ClpG sub-unit comprises an amino acid sequence containing a permissive region, wherein said ClpG sub-unit is modified by at least one heterologous peptide in said permissive region wherein said permissive region is selected from the group consisting of the region that covers the signal peptide and the N-terminal end of the mature protein defined by the amino acids located at positions −13 and +8 in SEQ ID NO: 2;

the region defined by the amino acids located at position 10 and 58 in SEQ ID NO:2;

the region defined by the amino acids located at positions 123 and 164 in SEQ ID NO:2; and the region defined by the amino acids located at positions 183 and 257 in SEQ ID NO:2.

2. The ClpG sub-unit of a CS31A protein capsule of claim 1, wherein its amino-acid sequence is modified between the amino acids located at positions −1 and +1 in FIG. 9 (SEQ ID NO:2).

3. The ClpG sub-unit of a CS31A protein capsule of claim 1, wherein its amino-acid sequence is modified at least at an epitope defined by the amino acids located at positions selected from the group consisting of position 10 and 19 and positions 38 and 58 in FIG. 9 (SEQ ID NO:2).

4. The ClpG sub-unit of a CS31A protein capsule of claim 1, wherein its amino-acid sequence is modified at least at an epitope defined by the amino acids located at positions 151 and 160 in FIG. 9 (SEQ ID NO:2).

5. The ClpG sub-unit of a CS31A protein capsule of claim 1, wherein its amino-acid sequence is modified at least at an epitope selected from the group consisting of those epitopes defined by the amino acids located at positions 188 and 196, positions 211 and 219, positions 223 and 231, and positions 235 and 246 in FIG. 9 (SEQ ID NO:2).

6. The ClpG sub-unit of a CS31A protein capsule of claim 1, wherein its amino-acid sequence is modified by at least one heterologous peptide obtained from bacteria, parasites, or viruses.

7. The ClpG sub-unit of a CS31A protein capsule of claim 6, wherein its amino-acid sequence is modified by at least one heterologous peptide selected from the group consisting of the C epitope or the A epitope of the transmissible pork gastroenteritis virus, an epitope of the V6 protein of bovine rotavirus, the C3 epitope of the polio virus, and an epitope of the VP1 protein of the aphthous fever virus.

8. A CS31A protein capsule that includes the ClpG sub-unit of claim 1.

9. A microorganism having an outer membrane that carries the CS31A protein capsule of claim 8.

10. An immmunogenic composition that includes, as an active ingredient, at least one sub-unit of the protein capsule of claim 8, or at least one microorganism of claim 9.

11. A vaccine which comprises the immunogenic composition of claim 10.

12. The ClpG sub-unit of a CS31A protein capsule of claim 1, wherein the heterologous peptide is from 4 to 18 amino acids long.

13. The ClpG sub-unit of a CS31A protein capsule of claim 6, which comprises two heterologous viral peptides.

14. The ClpG sub-unit of a CS31A protein capsule of claim 13 wherein the two viral peptides are peptides of different viruses.

15. The ClpG sub-unit of a CS31A protein capsule of claim 7 which comprise two epitopes of the transmissible pork gastroenteritis virus.

16. The ClpG sub-unit of a CS31A protein capsule of claim 7 which comprises an epitope of the transmissible port gastroenteritis virus and a epitope of the polio virus.

17. The vaccine of claim 11 wherein the antigenic compound contains an epitope of transmissible gastroenteritis virus of swine or of bovine rotavirus.

18. The ClpG sub-unit of a CS31A protein of claim 1 wherein the modification into one of the permissive regions of the ClpG amino acid sequence is without affecting the biogenesis of the CS31A protein capsule.

19. The ClpG sub-unit of a CS31A protein capsule of claim 1 whereby the modification of the amino acid sequence in the V2 region is by introduction of a DNA fragment that codes for a heterologous peptide, the modification being without deletion of amino acids at positions +131 to +141, whereby the biogenesis of the CS31A protein capsule is not affected.

20. A process for obtaining a ClpG subunit of a CS31A protein whose amino-acid sequence is modified by at least one heterologous peptide, comprising introducing at least one fragment of DNA that codes for a heterologous peptide into the gene that codes for the sub-unit and expressing the encoded sub-unit, wherein the DNA fragment that codes for said heterologous peptide is introduced into the segment of the gene that codes for a region of said sub-unit selected from the group consisting of the region that covers the signal peptide and the N-terminal end of the mature protein defined by the amino acids located at positions −13 and +8 in SEQ ID NO:2;

the region defined by the amino acids located at positions 10 and 58 in SEQ ID NO:2;

the region defined by the amino acids located at positions 123 and 164 in SEQ ID NO:2; and the region defined by the amino acids located at positions 183 and 257 in SEQ ID NO:2.

21. The process of claim 20, wherein the DNA fragment that codes for a heterologous peptide is introduced by cloning into the gene that codes for the sub-unit after directed mutagenesis leading to the creation of restriction sites, by cloning into restriction sites introduced by random insertional mutagenesis, or by directed insertion of a heterologous epitope between the signal peptide and the mature peptide of the pre-protein of the sub-unit.

22. The process of claim 20, wherein the DNA fragment that codes for a heterologous peptide is introduced into the segment of the gene that codes for the region of the sub-unit defined by the amino acids located at positions −1 and +1 in FIG. 9 (SEQ ID NO:2).

23. The process of claim 20, wherein the DNA fragment that codes for a heterologous peptide is introduced into the segment of the gene that codes for a region of the sub-unit defined by the amino acids selected from the group consisting of amino acids located at positions 10 and 19 and located at positions 38 and 58 in FIG. 9 (SEQ ID NO:2).

24. The process of claim 20, wherein the DNA fragment that codes for a heterologous peptide is introduced into the segment of the gene that codes for the region of the sub-unit defined by the amino acids located at positions 151 and 160 in FIG. 9 (SEQ ID NO:2).

25. The process of claim 20, wherein the DNA fragment that codes for a heterologous peptide is introduced into the segment of the gene that codes for one of the region of the sub-unit selected from the regions consisting of defined by the amino acids located at positions 188 and 196, positions 211 and 219, positions 223 and 231, and positions 235 and 246 in FIG. 9 (SEQ ID NO:2).

26. The process of claim 20 wherein the DNA fragment that codes for a heterologous peptide is between 3 to 54 base pairs in length.

27. The process for obtaining the ClpG sub-unit of a CS31A protein of claim 20 wherein the introduction of at least one fragment of DNA that codes for the heterologous peptide into the region of the gene that codes for the permissive region of the ClpG subunit and expressing the encoded sub-unit does not affect biogenesis of the CS31A protein capsule.

28. The process of claim 27 wherein the introduction of the DNA fragment is by direct mutagenesis.

29. The process of claim 20 wherein after the introduction of the DNA fragment that codes for a heterologous peptide in the V2 region from amino acid at position +123 to the amino acid at position +150, in FIG. 9 (SEQ ID NO:2), no deletion is made of amino acids at position +131 to +141, whereby the biogenesis of the CS31A protein capsule is not affected.

* * * * *